United States Patent
Kim et al.

(10) Patent No.: US 12,139,455 B2
(45) Date of Patent: Nov. 12, 2024

(54) POLYETHYLENE GLYCOL DERIVATIVE AND USE THEREOF

(71) Applicant: HANMI PHARM. CO., LTD., Hwaseong-si (KR)

(72) Inventors: Dae Jin Kim, Hwaseong-si (KR); Jong Soo Lee, Hwaseong-si (KR); Sung Min Bae, Hwaseong-si (KR); Se Chang Kwon, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 18/085,341

(22) Filed: Dec. 20, 2022

(65) Prior Publication Data

US 2023/0212103 A1 Jul. 6, 2023

Related U.S. Application Data

(62) Division of application No. 16/082,737, filed as application No. PCT/KR2017/002469 on Mar. 7, 2017, now Pat. No. 11,603,346.

(30) Foreign Application Priority Data

Mar. 7, 2016 (KR) .................. 10-2016-0027317

(51) Int. Cl.
| | |
|---|---|
| *C07C 47/198* | (2006.01) |
| *A61K 38/18* | (2006.01) |
| *A61K 39/395* | (2006.01) |
| *A61K 47/50* | (2017.01) |
| *A61K 47/60* | (2017.01) |
| *C07C 233/05* | (2006.01) |
| *C07C 233/18* | (2006.01) |
| *C07C 237/04* | (2006.01) |
| *C07C 323/12* | (2006.01) |
| *C07C 323/22* | (2006.01) |
| *C07C 323/39* | (2006.01) |
| *C07D 213/71* | (2006.01) |

(52) U.S. Cl.
CPC ............ *C07C 47/198* (2013.01); *A61K 38/18* (2013.01); *A61K 39/395* (2013.01); *A61K 47/50* (2017.08); *A61K 47/60* (2017.08); *C07C 233/05* (2013.01); *C07C 233/18* (2013.01); *C07C 237/04* (2013.01); *C07C 323/12* (2013.01); *C07C 323/22* (2013.01); *C07C 323/39* (2013.01); *C07D 213/71* (2013.01)

(58) Field of Classification Search
CPC .................................................. C07C 47/198
See application file for complete search history.

(56) References Cited

U.S. PATENT DOCUMENTS

2015/0182593 A1  7/2015  Jung et al.

FOREIGN PATENT DOCUMENTS

| CN | 102892420 A | 1/2013 |
|---|---|---|
| KR | 10-2005-0025974 A | 3/2005 |
| KR | 10-2011-0047169 A | 5/2011 |
| KR | 10-2013-0040889 A | 4/2013 |
| KR | 10-2014-0018462 A | 2/2014 |
| WO | 96/032478 A1 | 10/1996 |
| WO | 97/034631 A1 | 9/1997 |
| WO | 01/002017 A2 | 1/2001 |
| WO | 2002087497 A2 | 11/2002 |
| WO | 2009/134976 A1 | 11/2009 |
| WO | 2010/021720 A1 | 2/2010 |
| WO | 2010/138343 A1 | 12/2010 |
| WO | 2011126974 A1 | 10/2011 |
| WO | 2015/173824 A1 | 11/2015 |
| WO | 2015/183054 A1 | 12/2015 |

OTHER PUBLICATIONS

Andre' M. Cantin, et al., "Polyethylene Glycol Conjugation at $Cys^{232}$ Prolongs the Half-Life of α1 Proteinase Inhibitor", American Journal of Respiratory Cell and Molecular Biology, 2002, pp. 659-665, vol. 27.
International Search Report for PCT/KR2017/002469 dated Jul. 13, 2017 [PCT/ISA/210].
Ohkawa H et al.: "Synthesis of Multiacyl Poly(Ethylene Glycol) for the Conjugation of Cytochrome C To Phospholipid Vesicle", Bioconjugate Chemistry, American Chemical Society, US, vol. 11, No. 6, Nov. 1, 2000, pp. 815-821, XP001015727.
Fan Chen et al., "Understanding chemical reactivity for homo- and heterobifunctional protein cross-linking agents", Journal of Mass Spectrometry, vol. 48, Issue 7, Jun. 18, 2013, 1 page, Abstract only.
Oba et al., "Cyclic RGD Peptide-Conjugated Polyplex Micelles as a Targetable Gene Delivery System Directed to Cells Possessing rv3 and rv5 Integrins", Bioconjugate Chem., 2007, vol. 18, pp. 1415-1423 (9 pages total).
STN on the Web Registry, Registry, Chemical Abstract RN, RN: 1294505-04-6, May 13, 2011 (1 page total).
Chattopadhyay et al., "Design and Characterization of HER-2-Targeted Gold Nanoparticles for Enhanced X-radiation Treatment of Locally Advanced Breast Cancer", Molecular Pharmaceutics, 2010, vol. 7, No. 6, pp. 2194-2206.
Noel et al., "Development of a Polyester Coating Combining Antithrombogenic and Cell Adhesive Properties: Influence of Sequence and Surface Density of Adhesion Peptides", Biomacromolecules, 2015, vol. 16, pp. 1682-1694.
Wang et al., "Synthesis of new dimeric-PEG-supported cinchona ammonium salts as chiral phase transfer catalysts for the alkylation of Schiff bases with water as the solvent", Asymmetry, 2007, vol. 18, pp. 108-114.

(Continued)

*Primary Examiner* — David K O'Dell
(74) *Attorney, Agent, or Firm* — Sughrue Mion, PLLC

(57) ABSTRACT

Polyethylene glycol derivatives of the following formula I and uses thereof are disclosed. A method for manufacturing the polyethylene glycol derivatives is also disclosed.

Formula I

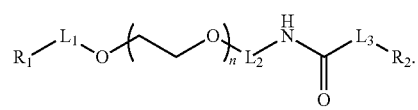

16 Claims, 22 Drawing Sheets

Specification includes a Sequence Listing.

(56) References Cited

OTHER PUBLICATIONS

Chemical Abstract Services 2002:849372 Document No. 137:358119 2002, 2 pages.
Allen "A new strategy for attachment of antibodies to sterically stabilized liposomes resulting in efficient targeting to cancer cells" Biochimica et Biophysica Acta 1237 (1995) 99-108.
PEG (Succinimidyl Carboxymethyl Ester)2 Online "https://www.jenkemusa.com/product/peg-di-succinimidyl-carboxymethyl-ester" accessed Jan. 4, 2020.
Vanderhooft Biomacromolecules (2007), 8(9), 2883-2889.
Brinkley "A Brief Survey of Methods for Preparing Protein Conjugates with Dyes, Haptens, and Cross-Linking Reagents." Bioconjugate Chemistry 1992, 3, 2-13.

[FIG. 1a]
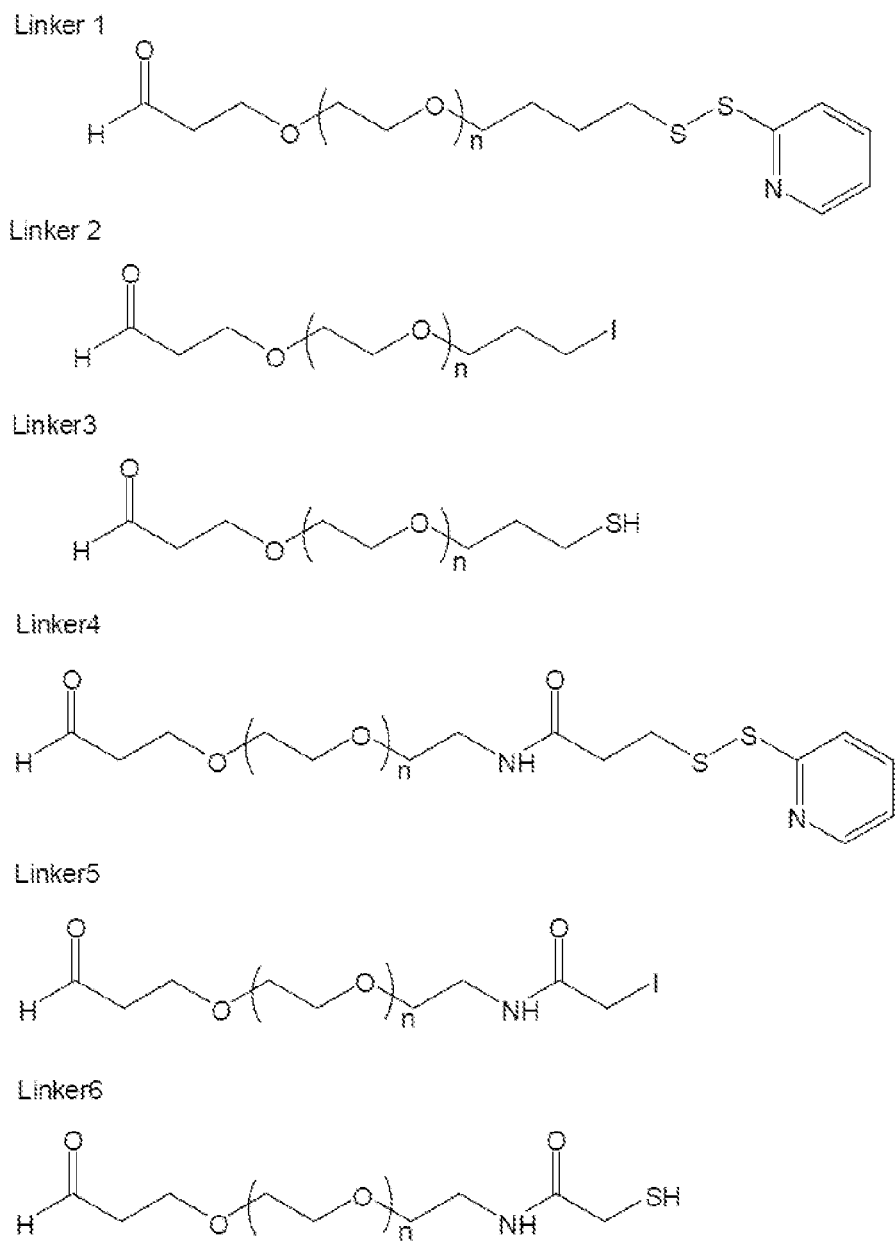

[FIG. 1b]
Linker7
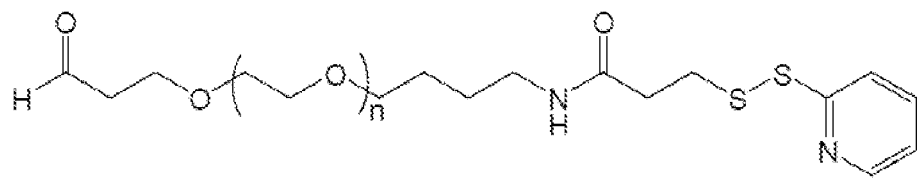
Linker8
Linker9
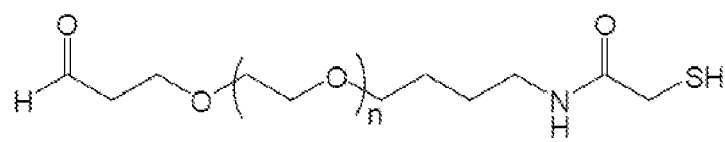
Linker 10
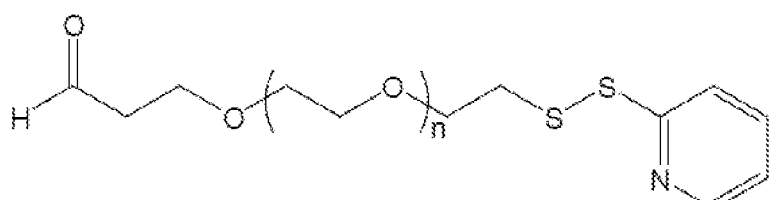
Linker 11
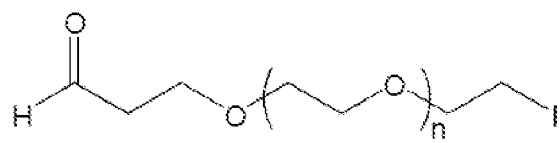
Linker 12
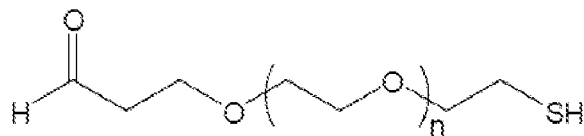

[FIG. 18]
Test of Reactivity Comparison of Thiol reactive group
| Linker No. | Thiol reactive group | Structure Presence of Amide (-CONH-) | Purity (RPC) | Reactivity (PEGylation @ General Condition *) |
|---|---|---|---|---|
| 3 | SH | x | 75.9% | 2.3% |
| 9 | SH | o | 75.9% | 14.5% |
| 11 | I | x | 88.7% | NA |
| 2 | I | x | 86.6% | NA |
| 2 | IA | o | 88.0% | 12.3% |
| 8 | IA | o | 78.2% | 39.2% |
*3mg/ml, 50mM HEPES (pH 7.5), 60% IPA, 2 hrs @ RT & Dark
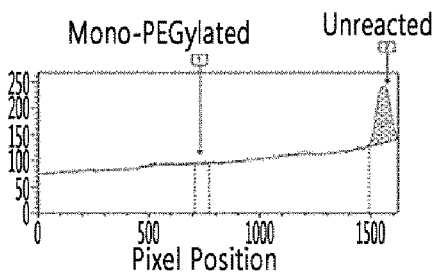
Linker 3 (2.3%)
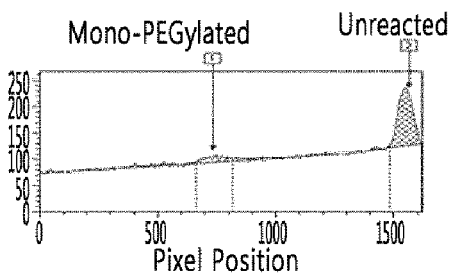
Linker 9 (14.5%)
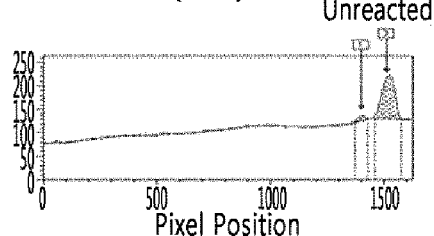
Linker 2 (N/A)
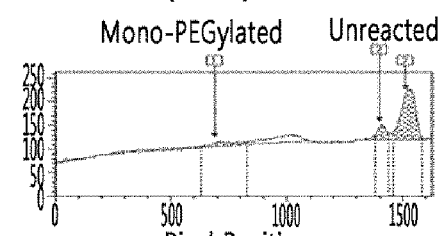
Linker 5 (12.3%)
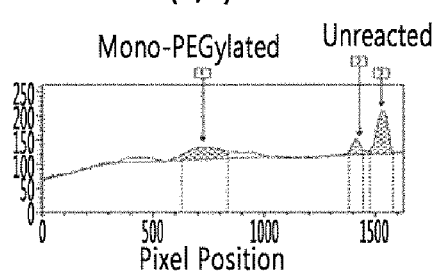
Linker 8 (39.2%)
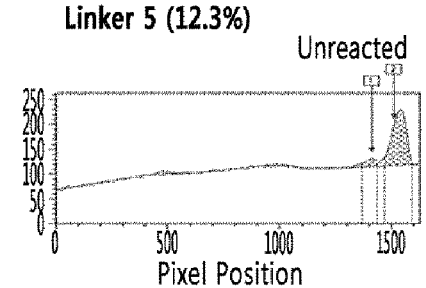
Linker 11 (N/A)

[FIG. 19]

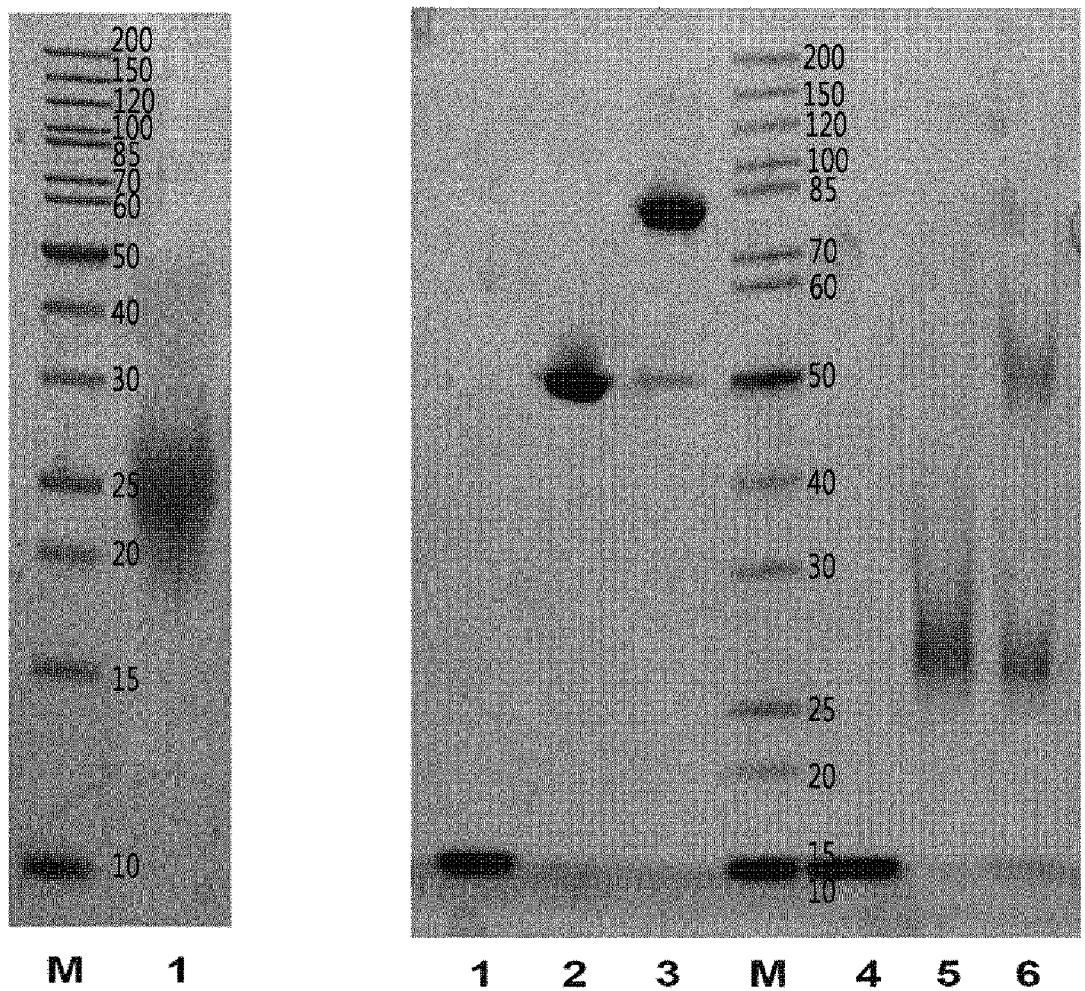

M: Marker
1: A conjugate where a linker #7 is linked to a triple agonist peptide (non-reducing)

1: Triple agonist peptides (non-reducing)
2: Immunoglobulin Fc (non-reducing)
3: A conjugate where a triple agonist peptide is linked with Immunoglobulin Fc by a linker #7 (non-reducing)
M: Marker
4: Triple agonist peptides (reducing)
5: Immunoglobulin Fc (reducing)
6: A conjugate where a triple agonist peptide is linked with Immunoglobulin Fc by a linker #7 (reducing)

[FIG. 20]

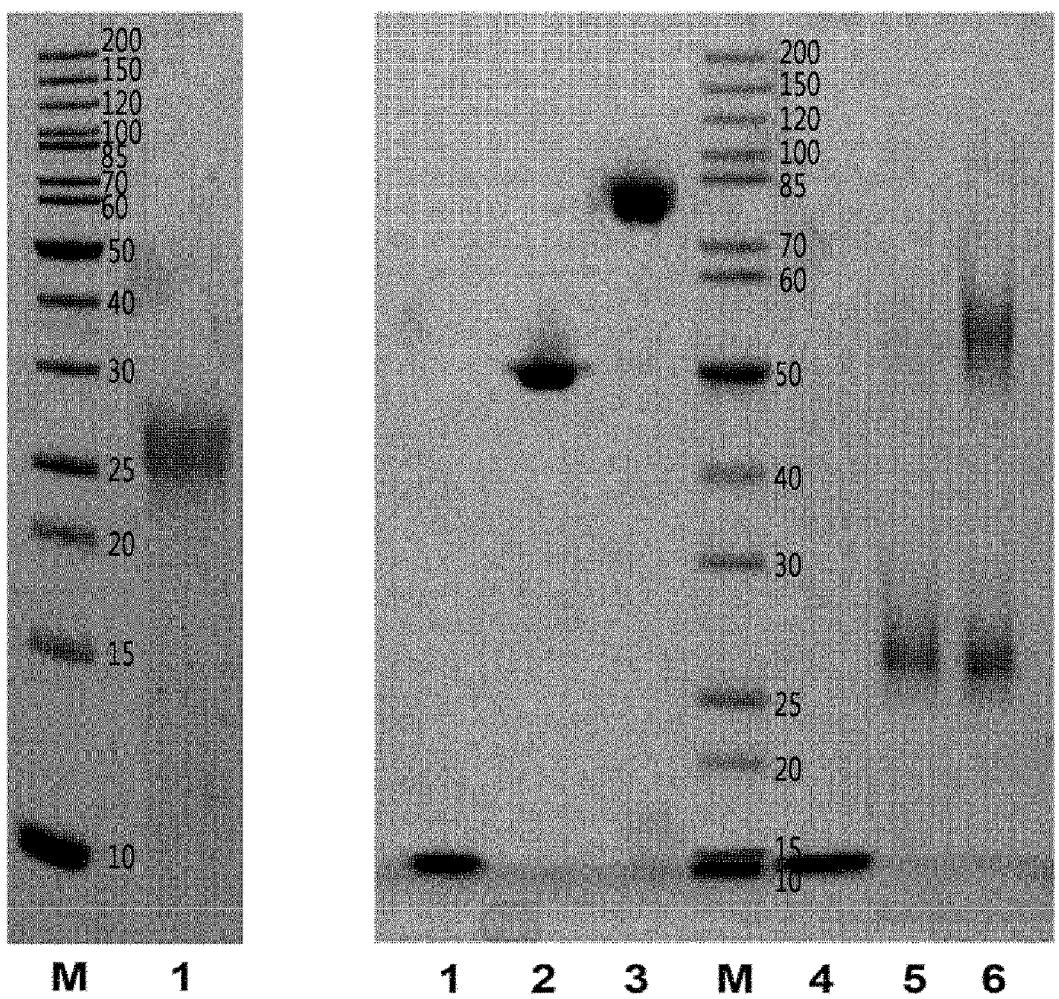

M: Marker
1: A conjugate where a linker #8 is linked to a triple agonist peptide (non-reducing)

1: Triple agonist peptides (non-reducing)
2: Immunoglobulin Fc (non-reducing)
3: A conjugate where a triple agonist peptide is linked with Immunoglobulin Fc by a linker #8 (non-reducing)
M: Marker
4: Triple agonist peptides (reducing)
5: Immunoglobulin Fc (reducing)
6: A conjugate where a triple agonist peptide is linked with Immunoglobulin Fc by a linker #8 (reducing)

[FIG. 21]

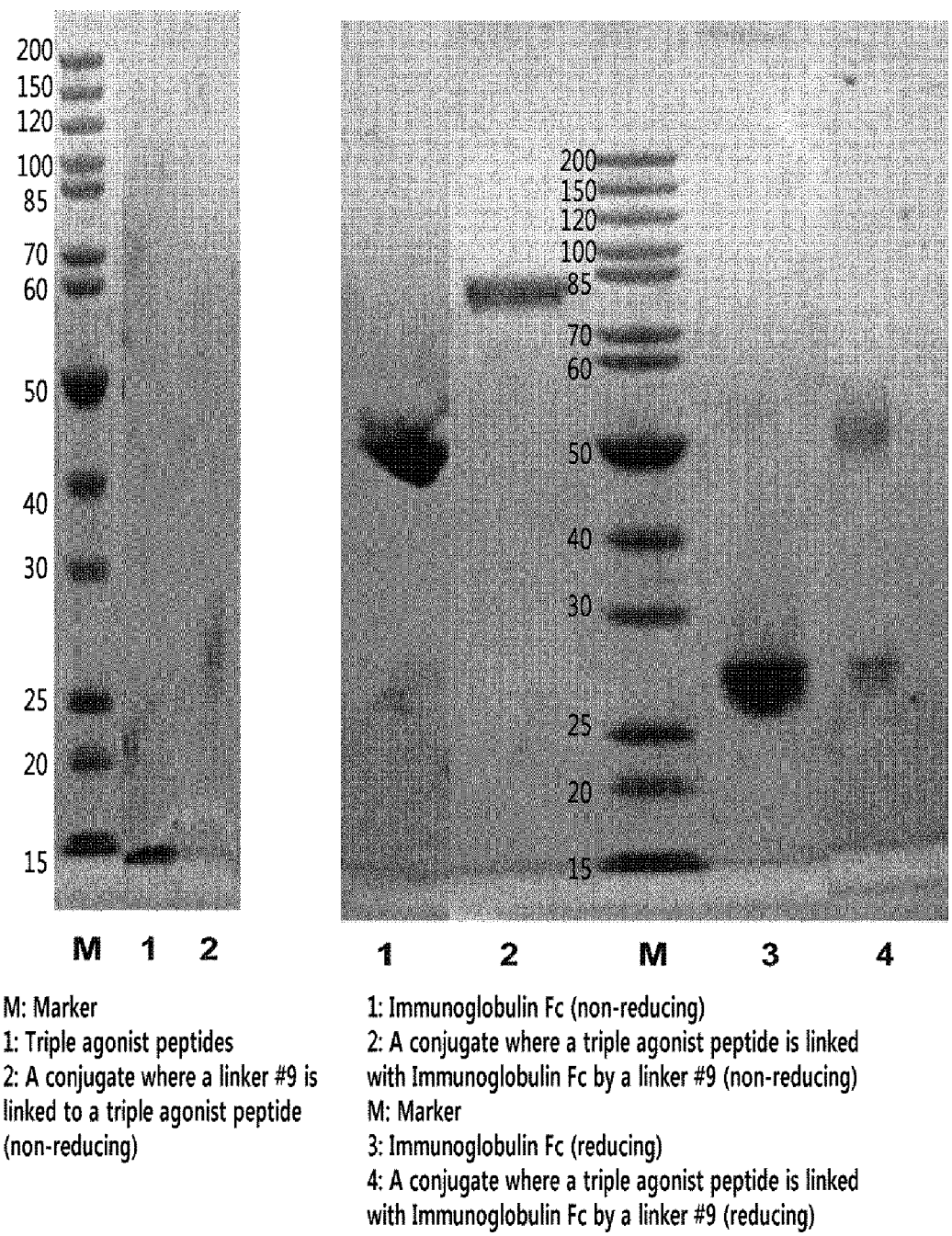

M: Marker
1: Triple agonist peptides
2: A conjugate where a linker #9 is linked to a triple agonist peptide (non-reducing)

1: Immunoglobulin Fc (non-reducing)
2: A conjugate where a triple agonist peptide is linked with Immunoglobulin Fc by a linker #9 (non-reducing)
M: Marker
3: Immunoglobulin Fc (reducing)
4: A conjugate where a triple agonist peptide is linked with Immunoglobulin Fc by a linker #9 (reducing)

POLYETHYLENE GLYCOL DERIVATIVE AND USE THEREOF

CROSS REFERENCE TO RELATED APPLICATIONS

This application is a Divisional of U.S. application Ser. No. 16/082,737 filed Sep. 6, 2018, which is National Stage of International Application No. PCT/KR2017/002469 filed Mar. 7, 2017, claiming priority based on Korean Patent Application No. 10-2016-0027317 filed Mar. 7, 2016.

INCORPORATION BY REFERENCE OF SEQUENCE LISTING

The content of the electronically submitted sequence listing, file name: Q282979_Sequence_Listing_As_Filed.xml; size: 217,594 bytes; and date of creation: Dec. 20, 2022, filed herewith, is incorporated herein by reference in its entirety.

TECHNICAL FIELD

The present invention relates to polyethylene glycol derivatives and uses thereof.

BACKGROUND ART

Polyethylene glycol (PEG) is a material which has a high in vivo half-life but does not have antigenicity. PEG is a representative biocompatible material which is widely used pharmaceutically when bound to various physiologically active materials such as lipids, proteins, etc., and studies on the pharmaceutical use of PEG itself are underway.

In particular, PEG is widely used from the aspect of protein therapeutics because PEG can bind to protein therapeutics and thereby increase their blood half-life while reducing their antigenicity. Additionally, it was reported that PEGylation, which refers to the covalent linking of PEG molecules to proteins, can improve the stability of protein therapeutics (Cantin et al., Am. J. 27: 659-665 (2002)).

Meanwhile, during the manufacturing process, improving the manufacturing yield of these medicaments while maintaining the activities of the medicament requires sophisticated manufacturing technology. Accordingly, continuous studies have been made to develop methods for manufacturing protein therapeutics including PEG and the PEG used therein.

In preparing a physiologically active polypeptide conjugate using PEG, the present inventors used PEG having at least two reactive groups as a linker (Korean Patent Application Publication No. 10-2014-0018462).

The conventional PEG compounds are known to have, as reactive groups, aldehyde, succinimidyl, maleimide, vinylsulfone, halogenated acetamide, or ortho-pyridyl disulfide (OPSS), etc.

However, the conventionally-used PEG compounds have an inconvenience in that although they have a reactive group at their ends, their reactivity varies due to the structures of the PEG compounds.

Accordingly, there has been a need for the development of a novel polyethylene glycol derivative which not only includes reactive groups capable of binding to target materials but also more easily reacts with these materials.

DISCLOSURE

Technical Problem

An object of the present invention is to provide a polyethylene glycol, a stereoisomer thereof, or a pharmaceutically acceptable salt thereof.

Another object of the present invention is to provide a method for preparing a physiologically active polypeptide to which a polyethylene glycol compound is attached, including reacting the polyethylene glycol compound with a physiologically active polypeptide.

Still another object of the present invention is to provide a method for preparing a conjugate in which a physiologically active polypeptide and a carrier protein are linked by a polyethylene glycol compound.

Still another object of the present invention is to provide a physiologically active polypeptide to which the polyethylene glycol compound is attached.

Still another object of the present invention is to provide a conjugate in which each of a physiologically active polypeptide and a carrier protein is independently attached to reactive groups at both ends of the polyethylene glycol compound.

Still another object of the present invention is to provide a method for preparing the polyethylene glycol compound.

Still another object of the present invention is to provide a use of the polyethylene glycol compound for linking a carrier, which is capable of increasing an in vivo half-life of a physiologically active polypeptide, to a physiologically active polypeptide.

Still another object of the present invention is to provide a composition containing the physiologically active polypeptide to which the polyethylene glycol compound is attached or the conjugate.

Still another object of the present invention is to provide a polyethylene glycol compound linker for linking a carrier, which is capable of increasing an in vivo half-life of a physiologically active polypeptide, to a physiologically active polypeptide.

Technical Solution

An aspect of the present invention provides a polyethylene glycol compound, a stereoisomer thereof, or a pharmaceutically acceptable salt thereof.

In a specific embodiment, the compound is a compound represented by Formula 1 below:

[Formula 1]

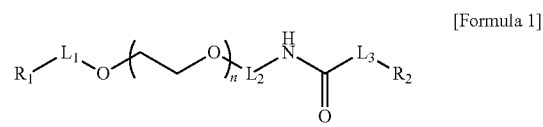

wherein, in Formula 1 above, $R_1$ is selected from the group consisting of 2,5-dioxopyrrolidinyl, 2,5-dioxopyrrolyl, aldehyde, maleimide, $C_{6-20}$ aryl disulfide, $C_{5-20}$ heteroaryl disulfide, vinyl sulfone, thiol, halogenated acetamide, succinimide, p-nitrophenyl carbonate, and derivatives thereof;

each of $L_1$ to $L_3$ is independently a linear or branched $C_{1-6}$ alkylene;

$R_2$ is ortho-pyridyl disulfide (OPSS), thiol, or halogen; and n is an integer of 10 to 2400.

In another specific embodiment, $R_2$ is ortho-pyridyl disulfide, thiol, or iodine.

In still another specific embodiment, $R_1$ is aldehyde.

In still another specific embodiment, $R_1$ and $R_2$ have mutually different functional groups.

In still another specific embodiment, the compound is represented by Formula 2 below:

CHO—(CH$_2$)$_j$—O—(CH$_2$CH$_2$O)$_n$—(CH$_2$)$_m$—NH(CO)—(CH$_2$)$_k$—R$_2$   [Formula 2]

wherein, in Formula 2 above;

n is an integer of 10 to 2400;

each of j, m, and k is independently an integer of 1 to 6; and $R_2$ is ortho-pyridyl disulfide (OPSS), thiol, or halogen.

In still another specific embodiment, the compound is selected from the group consisting of Formulas 3 to 11:

[Formula 3]
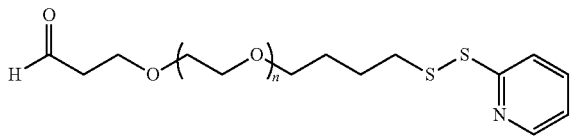

[Formula 4]
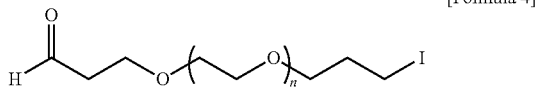

[Formula 5]
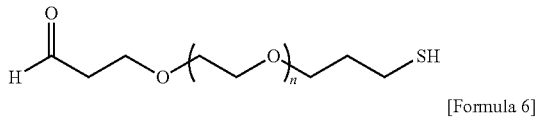

[Formula 6]
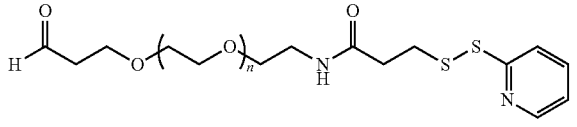

[Formula 7]
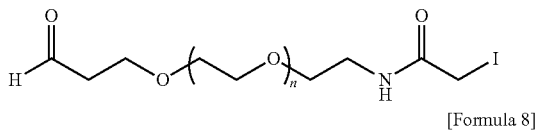

[Formula 8]
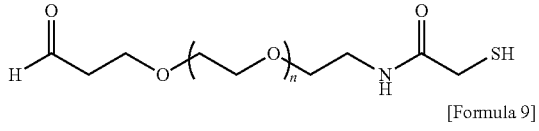

[Formula 9]
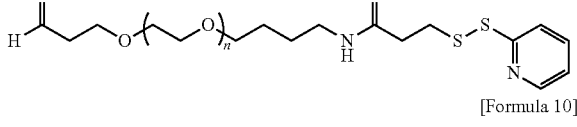

[Formula 10]
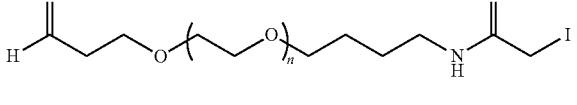

-continued

[Formula 11]
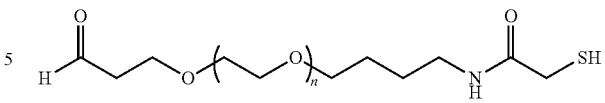

In Formulas 3 to 11, n is an integer of 10 to 2400.

Another aspect of the present invention provides a method for preparing a physiologically active polypeptide to which a polyethylene glycol compound is attached, which includes reacting a polyethylene glycol compound with a physiologically active polypeptide to prepare a physiologically active polypeptide to which a polyethylene glycol compound is attached.

In a specific embodiment of the method, ortho-pyridyl disulfide (OPSS), thiol, or halogen located at $R_2$ reacts with a thiol group located at the cysteine residue of the physiologically active polypeptide.

In another specific embodiment, the method further includes purifying the physiologically active polypeptide to which a polyethylene glycol compound is attached.

In still another specific embodiment, the physiologically active polypeptide is selected from the group consisting of hormones, cytokines, enzymes, antibodies, growth factors, transcription factors, blood factors, vaccines, insulinotropic peptides, neuropeptides, pituitary hormones, anti-obesity peptides, antiviral peptides, non-native peptide derivatives having a physiological activity, structural proteins, ligand proteins, and receptors.

In still another specific embodiment, the physiologically active polypeptide is selected from the group consisting of glucagon; insulin; somatostatin; peptide YY (PYY); neuropeptide Y (NPY); glucagon-like peptides including glucagon-like peptide-1 (GLP-1) and glucagon-like peptide-2 (GLP-2); exendin-3; exendin-4; oxyntomodulin; peptides having an activity on glucagon receptors, GLP-1 receptors, and GIP receptors; fibroblast growth factor; ghrelin; angiotensin; bradykinin; calcitonin; corticotropin; eledoisin; gastrin; leptin; oxytocin; vasopressin; luteinizing hormone; luteotropin; follicle-stimulating hormone; parathyroid hormone; secretin; sermorelin; human growth hormone (hGH); growth hormone-releasing peptides; granulocyte-colony-stimulating factors (GCSF); interferons (IFNs); interleukins; prolactin-releasing peptides; orexin; thyroid-releasing peptides; cholecystokinin; gastrin inhibitory peptides; calmodulin; gastric-releasing peptides; motilin; vasoactive intestinal peptides; atrial natriuretic peptides (ANPs); B-type natriuretic peptides (BNPs); C-type natriuretic peptides (CNPs); neurokinin A; neuromedin; renin; endothelin; sarafotoxin peptide; carsomorphin peptide; dermorphin; dynorphin; endorphin; enkepalin; T cell factors; tumor necrosis factor; tumor necrosis factor receptors; urokinase receptors; tumor inhibitory factors; collagenase inhibitors; thymopoietin; thymulin; thymopentin; thymosin; thymic humoral factor; adrenomedullin; allatostatin; amyloid β-protein fragments; antibacterial peptides; antioxidant peptides; bombesin; osteocalcin; CART peptides; E-selectin; ICAM-1; VCAM-1; leucokine; kringle-5; laminin; inhibin; galanin; fibronectin; pancreastatin; fuzeon; interferon receptors; G protein-coupled receptors; interleukin receptors; enzymes; interleukin-binding proteins; cytokine-binding proteins; macrophage-activating factors; macrophage peptides; B cell factor; protein A; allergy inhibitors; cell necrosis glycoprotein; immunotoxin; lymphotoxin; tumor inhibitory factors; metastasis growth factors; α-1-antitrypsin; albumin; α-lactalbumin; apolipoprotein-E; erythropoietin; highly glycosylated erythropoietin; angiopoietins; hemoglobin; thrombin; thrombin receptor-activating peptides; thrombomodulin; blood factors VII, VIIa, VIII, IX, and XIII; plasminogen-activating factors; fibrin-binding peptides; urokinase; streptokinase; hirudin; protein C; C-reactive protein; renin inhibitors; superoxide dismutase; platelet-derived growth factors; epidermal growth factors; epithelial cell growth factors; angiostatin; angiotensin; osteogenic growth factors; osteogenesis-promoting proteins; atriopeptin; cartilage-inducing factors; elcatonin; connective tissue-activating factors; tissue factor pathway inhibitors; luteinizing hormone-releasing hormone; nerve growth factors; relaxin; somatomedin; insulin-like growth factor; adrenocortical hormone; pancreatic polypeptides; gastrin-releasing peptides; corticotropin-releasing factor; thyroid-stimulating hormone; autotoxin; lactoferrin; myostatin; cell surface antigens; virus-derived vaccine antigens; monoclonal antibody; polyclonal antibody; antibody fragments; erythropoietic growth factors; leukopoietin; amylin; and analogs thereof.

Still another aspect of the present invention provides a method for preparing a conjugate, in which a physiologically active polypeptide and a carrier protein are linked by a polyethylene glycol compound.

In a specific embodiment, the method includes:

(a) reacting the polyethylene glycol compound with any one of a physiologically active polypeptide or carrier protein, thereby preparing a polyethylene glycol compound, wherein the physiologically active polypeptide or carrier protein is attached to one end of the polyethylene glycol compound and the other end of the polyethylene glycol compound has a reactive end group; and (b) reacting the polyethylene glycol compound prepared in step (a) above, wherein the physiologically active polypeptide or carrier protein is attached to one end of the polyethylene glycol compound and the other end of the polyethylene glycol compound has a reactive end group, with the other one between the physiologically active polypeptide or carrier protein, so as to link the carrier protein or physiologically active polypeptide to the reactive end group of the polyethylene glycol compound, thereby preparing a conjugate in which the physiologically active polypeptide and the carrier protein are linked by a polyethylene glycol compound.

In another specific embodiment, the method includes:

(a) reacting the polyethylene glycol compound with a physiologically active polypeptide, thereby preparing a polyethylene glycol compound, wherein the physiologically active polypeptide is attached to one end of the polyethylene glycol compound and the other end of the polyethylene glycol compound has a reactive end group; and (b) reacting the polyethylene glycol compound prepared in step (a) above, wherein the physiologically active polypeptide is attached to one end of the polyethylene glycol compound and the other end of the polyethylene glycol compound has a reactive end group, with a carrier protein, so as to link the carrier protein to the reactive end group of the polyethylene glycol compound.

In still another specific embodiment, the physiologically active polypeptide is selected from the group consisting of hormones, cytokines, enzymes, antibodies, growth factors, transcription factors, blood factors, vaccines, insulinotropic peptides, neuropeptides, pituitary hormones, anti-obesity peptides, antiviral peptides, non-native peptide derivatives having a physiological activity, structural proteins, ligand proteins, and receptors.

In still another specific embodiment, the polyethylene glycol compound in step (a) has the structure of Formula 1 above.

In still another specific embodiment, step (a) of the method is characterized in that $R_2$ of the polyethylene glycol compound having the structure of Formula 1 above is reacted with a thiol group located at the cysteine residue of the physiologically active polypeptide.

In still another specific embodiment, step (b) of the method is characterized in that an aldehyde end group of the polyethylene glycol compound is reacted with an amine group of an immunoglobulin Fc fragment.

In still another specific embodiment, the method further includes purifying the conjugate, wherein the physiologically active polypeptide and the carrier protein are linked by a polyethylene glycol compound.

In still another specific embodiment, the carrier protein is albumin and a fragment thereof, a polymer of a repeating unit of a particular amino acid sequence, antibody, an antibody fragment, an FcRn-binding material, fibronectin, transferrin, saccharide, or elastin.

In still another specific embodiment, the FcRn-binding material is an immunoglobulin Fc fragment.

Still another aspect of the present invention provides a physiologically active polypeptide to which the polyethylene glycol compound is attached.

In a specific embodiment, the physiologically active polypeptide, to which the above compound is attached, includes the structure represented by any one of Formulas 15 to 17 below:

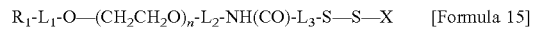  [Formula 15]

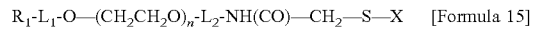  [Formula 15]

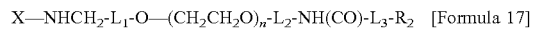  [Formula 17]

In Formulas 15 to 17 above, $R_1$ is selected from 2,5-dioxopyrrolidinyl, 2,5-dioxopyrrolyl, aldehyde, maleimide, $C_{6-20}$ aryl disulfide, $C_{5-20}$ heteroaryl disulfide, vinyl sulfone, thiol, halogenated acetamide, succinimide, p-nitrophenyl carbonate, and derivatives thereof;

each of $L_1$ to $L_3$ is independently a linear or branched $C_{1-6}$ alkylene;

n is an integer of 10 to 2400;

$R_2$ is ortho-pyridyl disulfide (OPSS), thiol, or halogen; and

X is a physiologically active polypeptide moiety.

Still another aspect of the present invention provides a conjugate, wherein each of a physiologically active polypeptide and a carrier protein is independently attached to reactive groups at both ends of the polyethylene glycol compound.

In a specific embodiment, the conjugate is a conjugate having the structure represented by Formula 18 or 19 below:

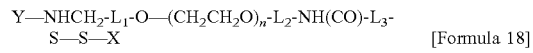  [Formula 18]

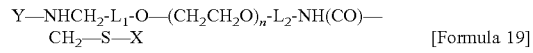  [Formula 19]

In Formulas 18 and 19 above, each of $L_1$ to $L_3$ is independently a linear or branched $C_{1-6}$ alkylene, n is an integer of 10 to 2400, X is a physiologically active polypeptide moiety; and Y is a carrier protein moiety.

In another specific embodiment, the carrier protein is albumin and a fragment thereof, a polymer of a repeating unit of a particular amino acid sequence, antibody, an antibody fragment, an FcRn-binding material, fibronectin, transferrin, saccharide, or elastin.

In still another specific embodiment, the FcRn-binding material is an immunoglobulin Fc fragment.

Still another aspect of the present invention provides a method for preparing the polyethylene glycol compound.

In a specific embodiment, the method includes:
(a) introducing $R_1$ selected from the group consisting of 2,5-dioxopyrrolidinyl, 2,5-dioxopyrrolyl, aldehyde, maleimide, $C_{6-20}$ aryl disulfide, $C_{5-20}$ heteroaryl disulfide, vinyl sulfone, thiol, halogenated acetamide, succinimide, p-nitrophenyl carbonate, and derivatives thereof, to one end of a polyethylene glycol; and
(b) introducing the structure of —NH(CO)$L_3$-$R_2$ to the other end of the polyethylene glycol, wherein $R_2$ is orthopyridyl disulfide (OPSS), thiol, or halogen.

In another specific embodiment, the method includes:
a first step for preparing a compound represented by Formula 21 below from a compound represented by Formula 20 below;
a second step for preparing a compound represented by Formula 22 below from a compound represented by Formula 21 below; and
a third step for converting the diethoxy methyl at an end of a compound represented by Formula 22 below into aldehyde by treating the compound represented by Formula 22 with an acid solution:

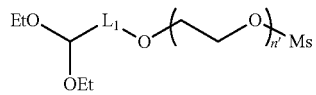
[Formula 20]

wherein, in Formula 20 above, n' is n or n+1; and

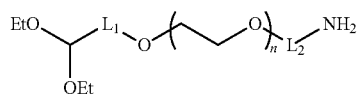
[Formula 21]

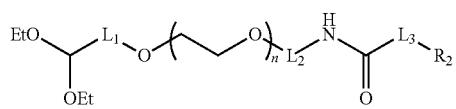
[Formula 22]

wherein $L_1$, $L_2$, $L_3$, n, and $R_2$ are the same as described above.

In still another specific embodiment, the compound represented by Formula 20 of the first step is prepared by reacting the compound represented by Formula 23 below with methanesulfonyl chloride:

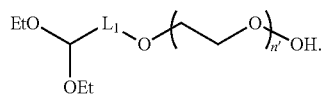
[Formula 23]

In still another specific embodiment, the first step is performed by reacting the compound represented by Formula 20 with an aqueous ammonia solution and ammonium chloride.

In still another specific embodiment, the first step includes:
step 1-1, which is to react a compound represented by Formula 20 with hydroxyalkyl tetrahydropyranyl ether, thereby preparing a compound represented by Formula 24;
step 1-2, which is to react a compound represented by Formula 24 with p-toluenesulfonic acid, thereby substituting the tetrahydropyranyloxy group at an end thereof with a hydroxy group;
step 1-3, which is to react the compound obtained in step 1-2 with methanesulfonyl chloride, thereby substituting the hydroxy group with a methanesulfonic acid group; and
step 1-4, which is to react the compound obtained in step 1-3 with an aqueous ammonia solution and ammonium chloride.

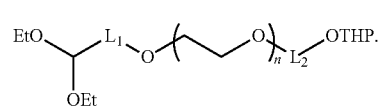
[Formula 24]

In still another specific embodiment, the second step is performed by reacting a compound represented by Formula 21 with a compound represented by Formula 25:

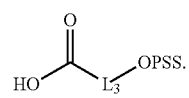
[Formula 25]

In still another specific embodiment, the second step includes: reacting a compound represented by Formula 21 with chloro($C_{2-7}$ alkanoyl) chloride, thereby synthesizing a compound comprising a chloro group at an end thereof, which is represented by Formula 26 below, as an intermediate product; and reacting the compound represented by Formula 26 with a halogen metal salt in the presence or absence of hydrogen sulfide, thereby converting the chloro group into thiol or halogen:

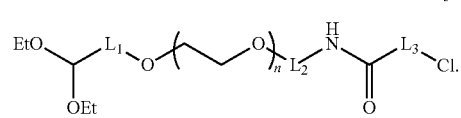
[Formula 26]

Still another aspect of the present invention provides a use of the polyethylene glycol compound for linking a carrier, which is capable of increasing an in vivo half-life of a physiologically active polypeptide, to a physiologically active polypeptide.

Still another aspect of the present invention provides a composition containing a physiologically active polypeptide to which the polyethylene glycol compound is attached or the conjugate.

Still another aspect of the present invention provides a linker for linking a carrier capable of increasing an in vivo half-life of a physiologically active polypeptide to a physiologically active polypeptide, wherein the linker includes a polyethylene glycol compound, a stereoisomer thereof, or a pharmaceutically acceptable salt thereof.

Advantageous Effects

The polyethylene glycol derivatives of the present invention have advantages in that they include desired reactive end groups at an end thereof, and at the same time, they can easily react with target materials (e.g., proteins) to be linked thereto. Accordingly, the polyethylene glycol derivatives of the present invention can be effectively used in the field of manufacturing medicaments with regard to conjugated drugs such as protein conjugates, etc.

BRIEF DESCRIPTION OF DRAWINGS

FIGS. 1a and 1b show exemplary embodiments of novel polyethylene glycol compounds of the present invention, illustrating the chemical structures of the compounds having an aldehyde group and an ortho-pyridyl disulfide group (linkers #1, #4, and #7), 2) the chemical structures of the compounds having an aldehyde group and an iodoacetamide group or iodine group (linkers #2, #5, and #8), and 3) the chemical structures of the compounds having an aldehyde group and a sulfhydryl group (linkers #3, #6, and #9). In FIG. 1b, linkers #10 to #12 correspond to comparative groups.

FIG. 18 shows the results of comparative experiments with regard to the reactivity of the thiol reactive groups of the polyethylene glycol compounds according to the present invention.

FIGS. 19 to 21 show the results of SDS-PAGE analyses with regard to the conjugates of triple agonist-PEG-Fc prepared using the polyethylene glycol compounds according to the present invention as a linker, in which FIG. 19 shows the result of SDS-PAGE analysis using linker #7 according to the present invention, FIG. 20 using linker #8, and FIG. 21 using linker #9, respectively.

DETAILED DESCRIPTION OF THE INVENTION

Figure 2:
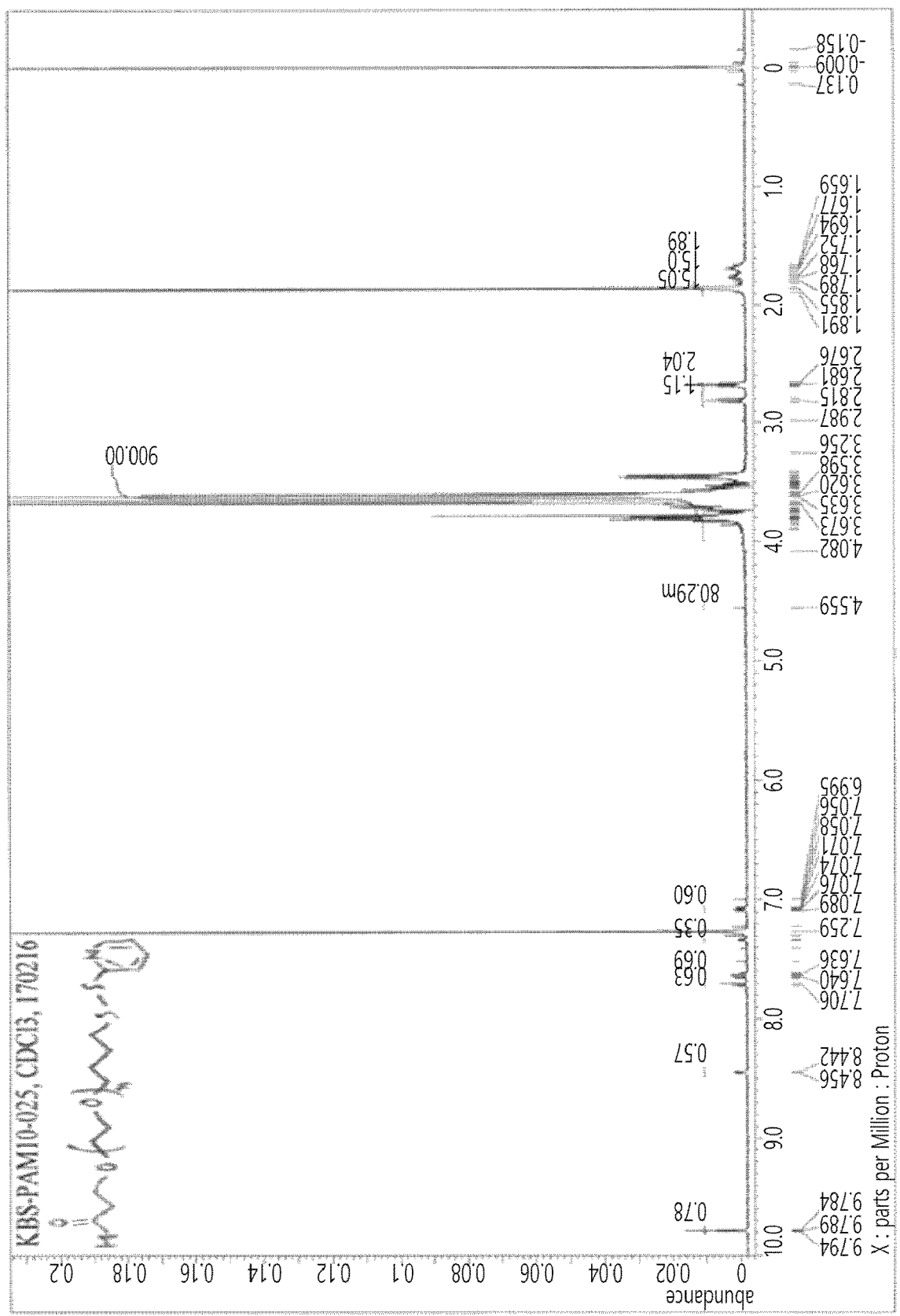
FIG. 2 shows the result of nuclear magnetic resonance (hereinafter, NMR) analysis confirming linker #1 after its preparation.
Figure 3:
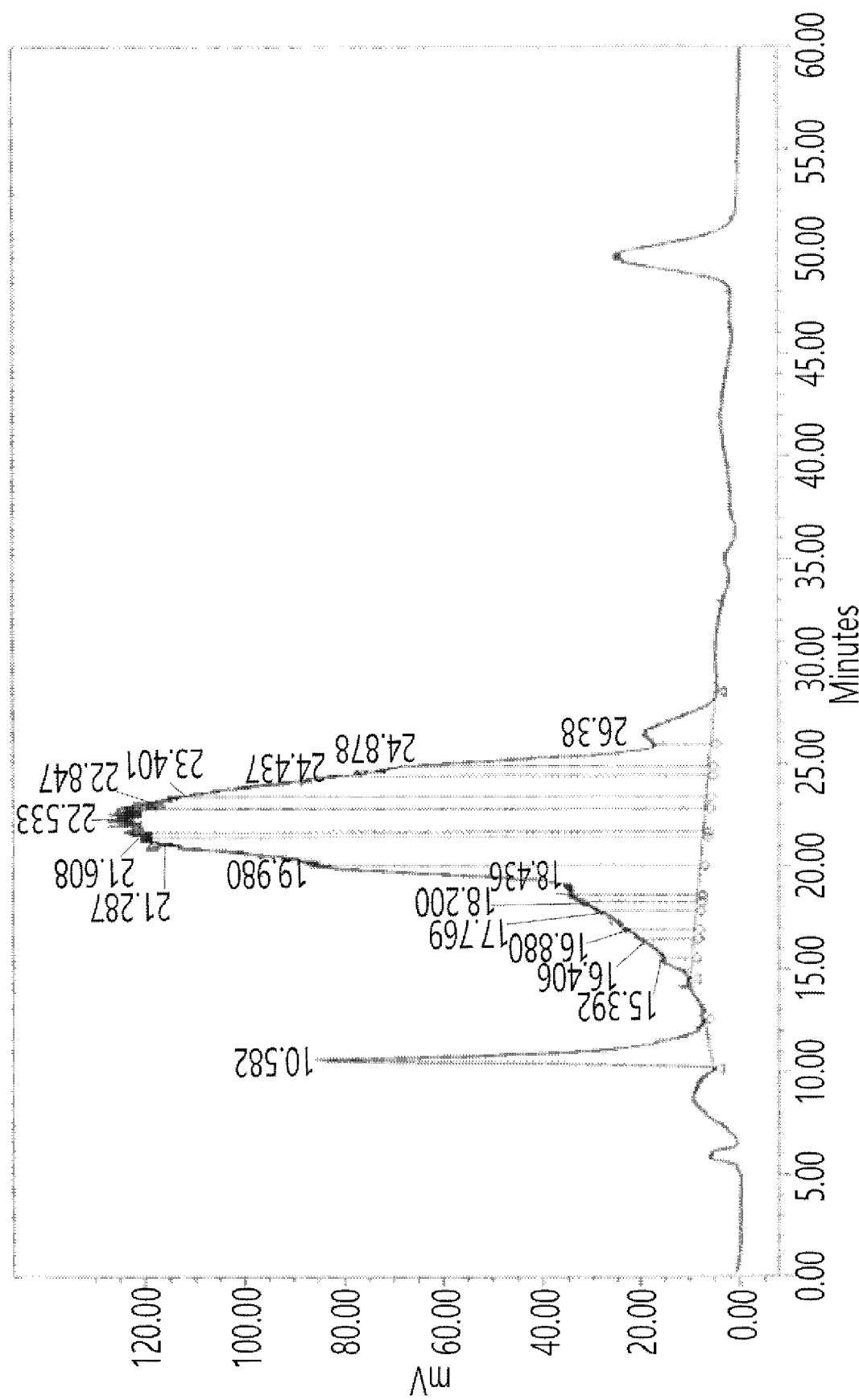
FIG. 3 shows the result of reversed phase chromatography (hereinafter, RPC) analysis of linker #1 after its preparation.
Figure 4:
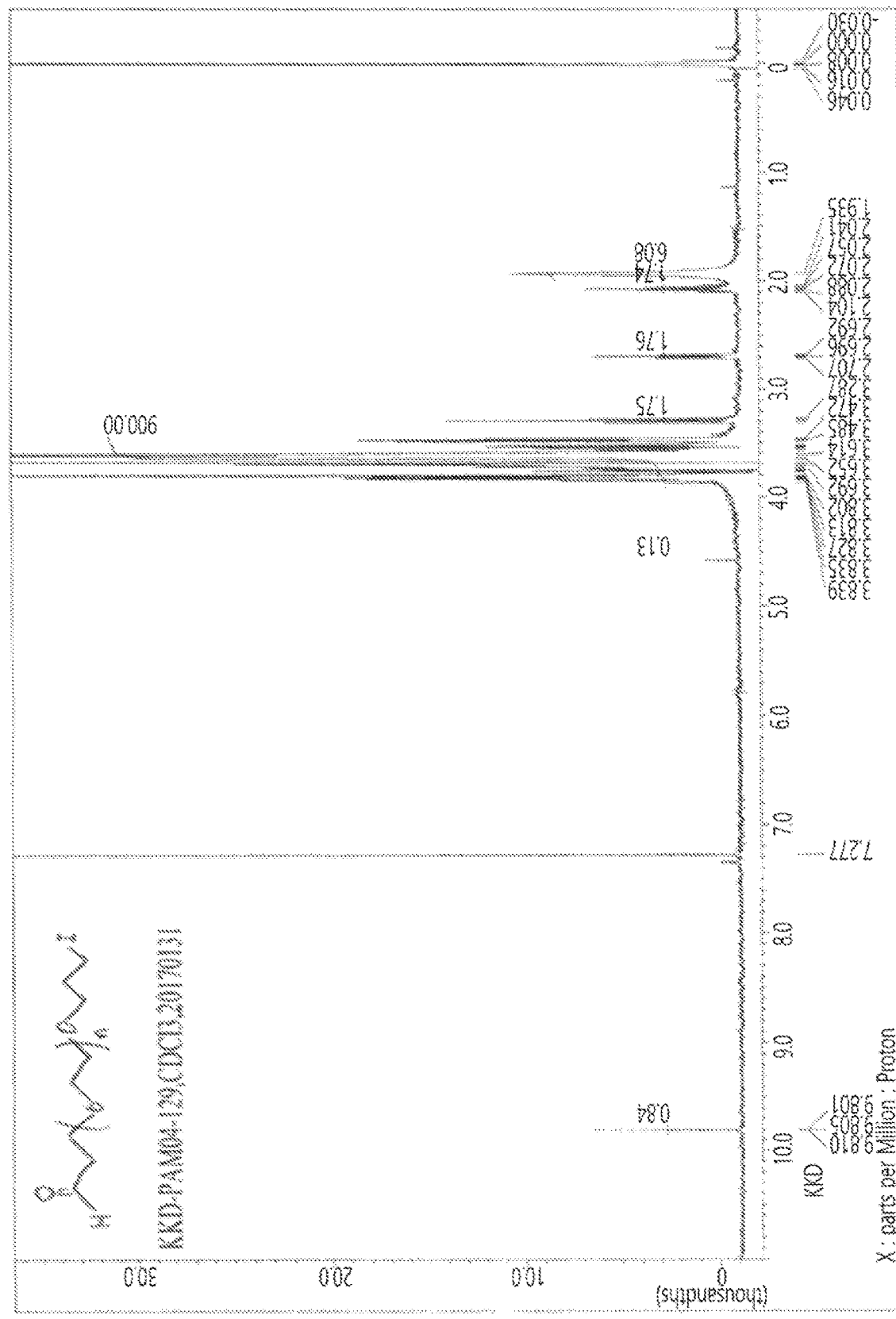
FIG. 4 shows the result of NMR analysis confirming linker #2 after its preparation.
Figure 5:
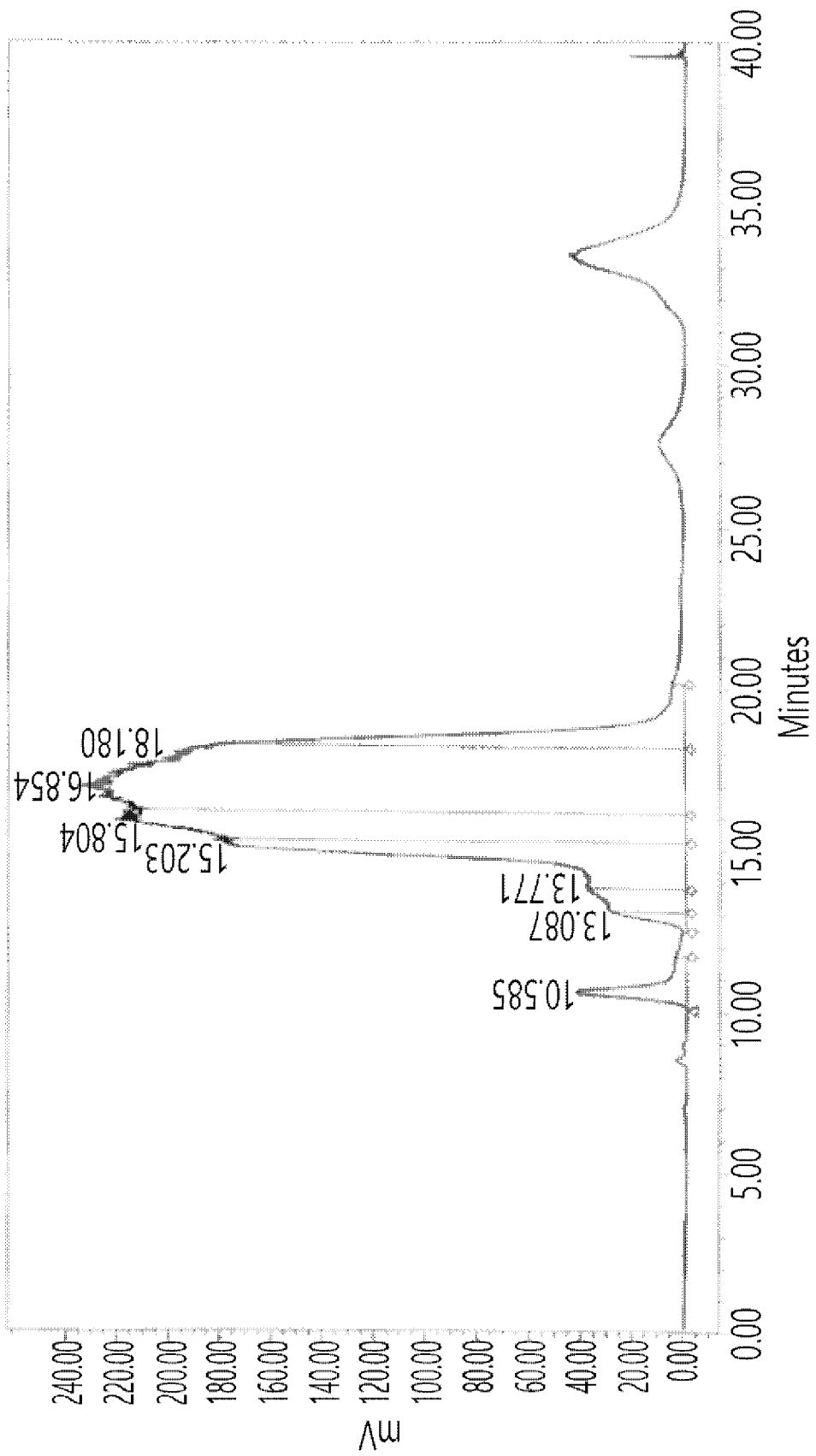
FIG. 5 shows the result of RPC analysis of linker #2 after its preparation.
Figure 6:
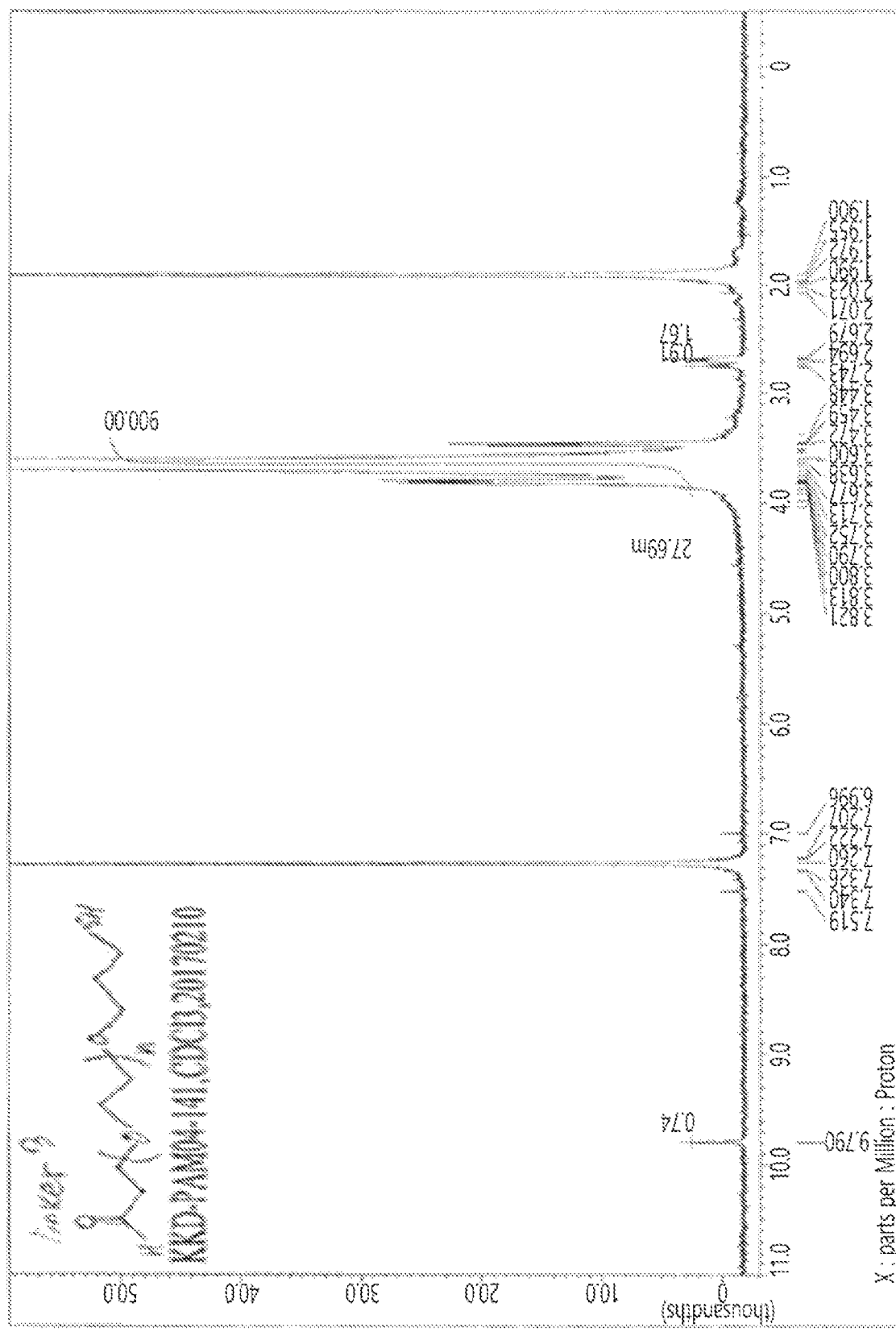
FIG. 6 shows the result of NMR analysis confirming linker #3 after its preparation.
Figure 7:
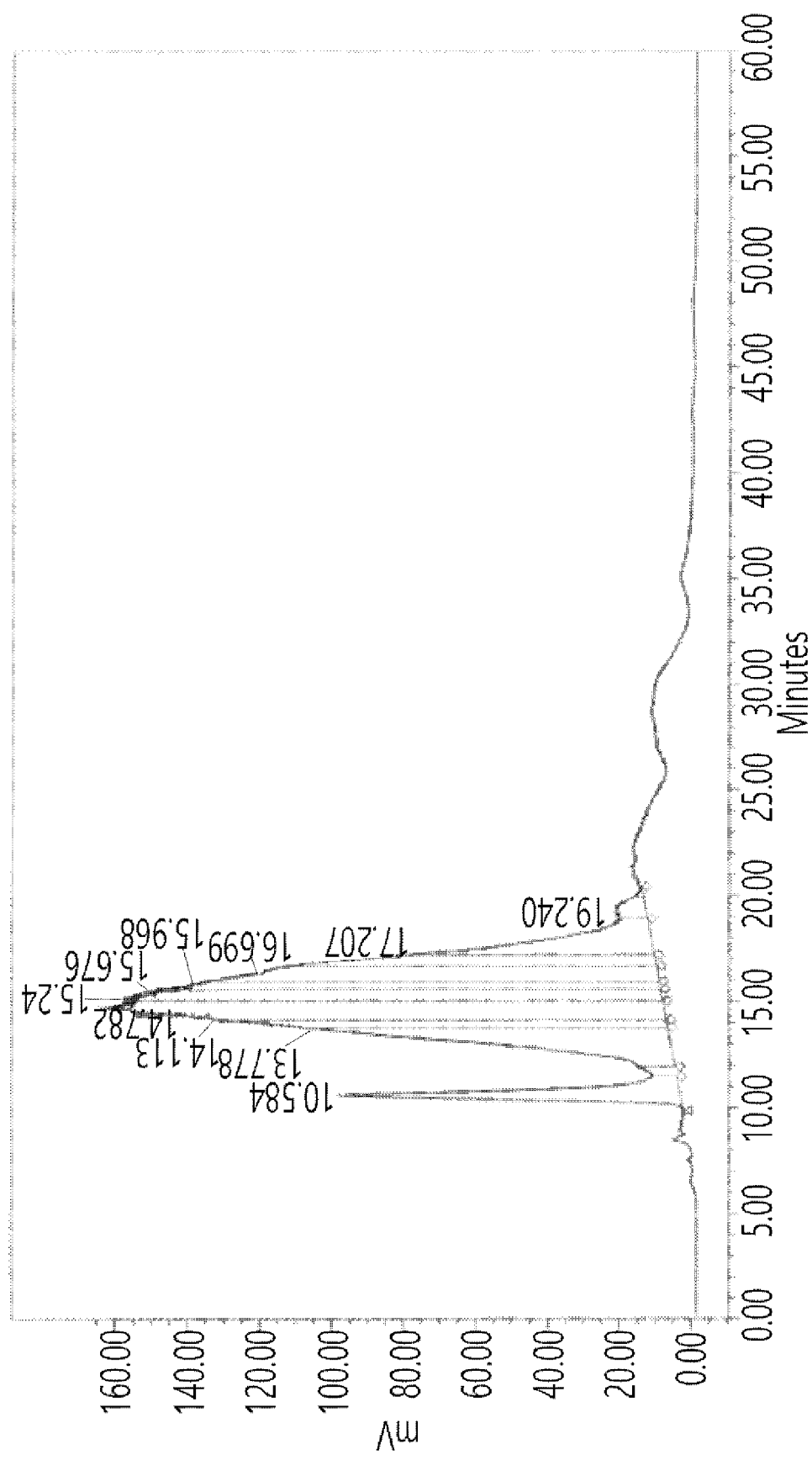
FIG. 7 shows the result of RPC analysis of linker #3 after its preparation.
Figure 8:
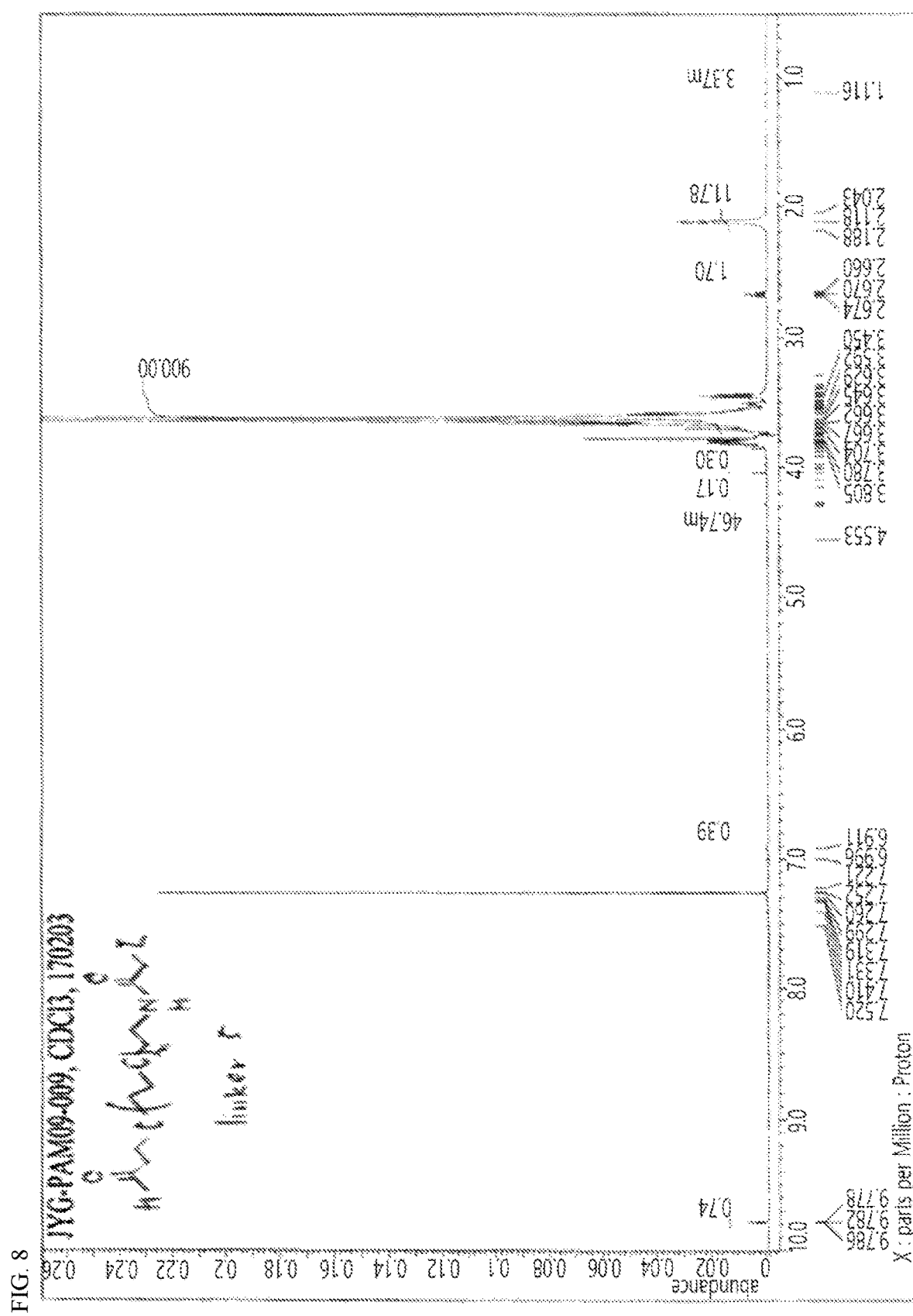
FIG. 8 shows the result of NMR analysis confirming linker #5 after its preparation.
Figure 9:
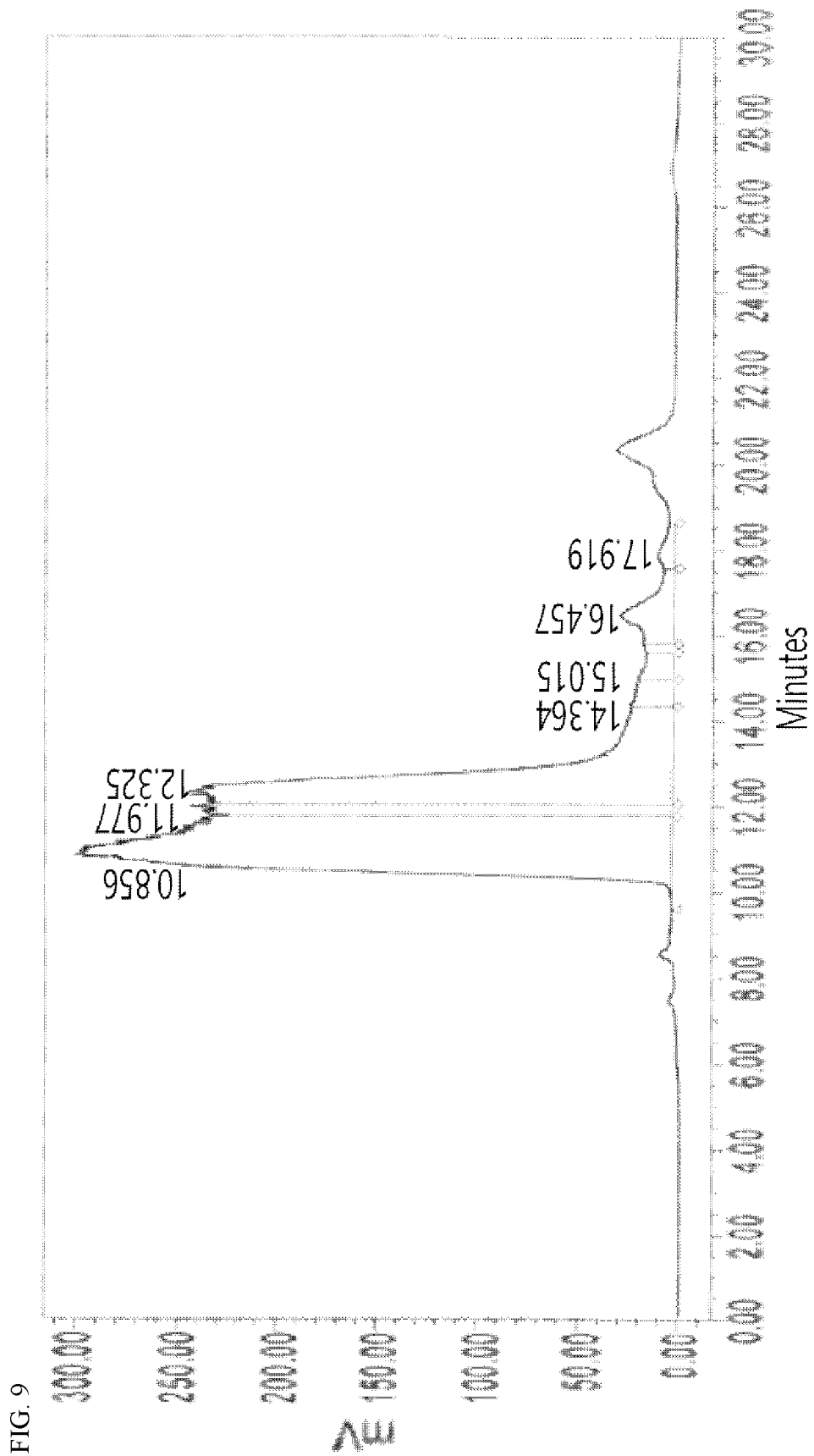
FIG. 9 shows the result of RPC analysis of linker #5 after its preparation.
Figure 10:
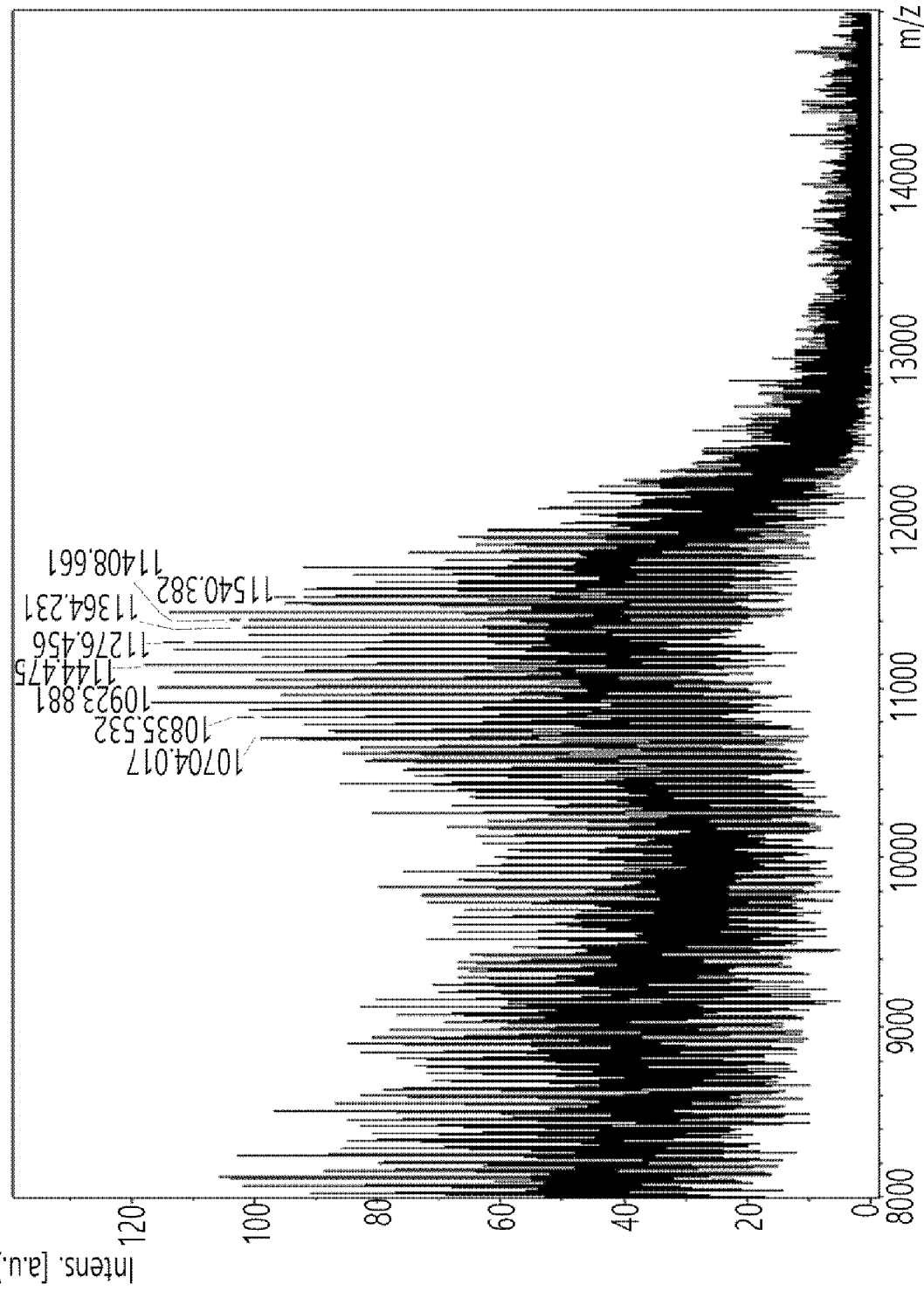
FIG. 10 shows the result of MALDI-TOF analysis of the molecular weight of linker #5 after its preparation.
Figure 11:
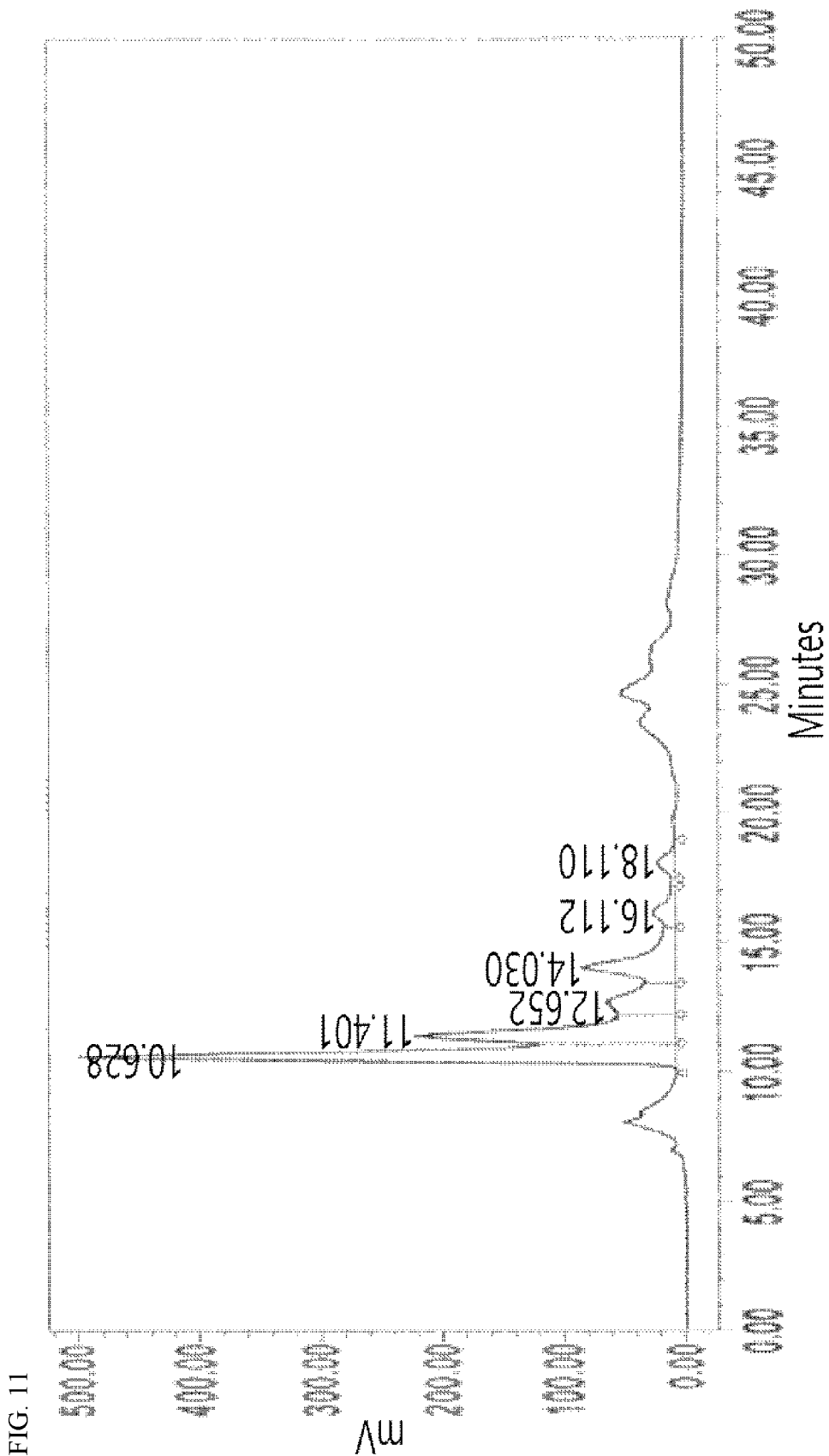
FIG. 11 shows the result of RPC analysis of linker #7 after its preparation.
Figure 12:
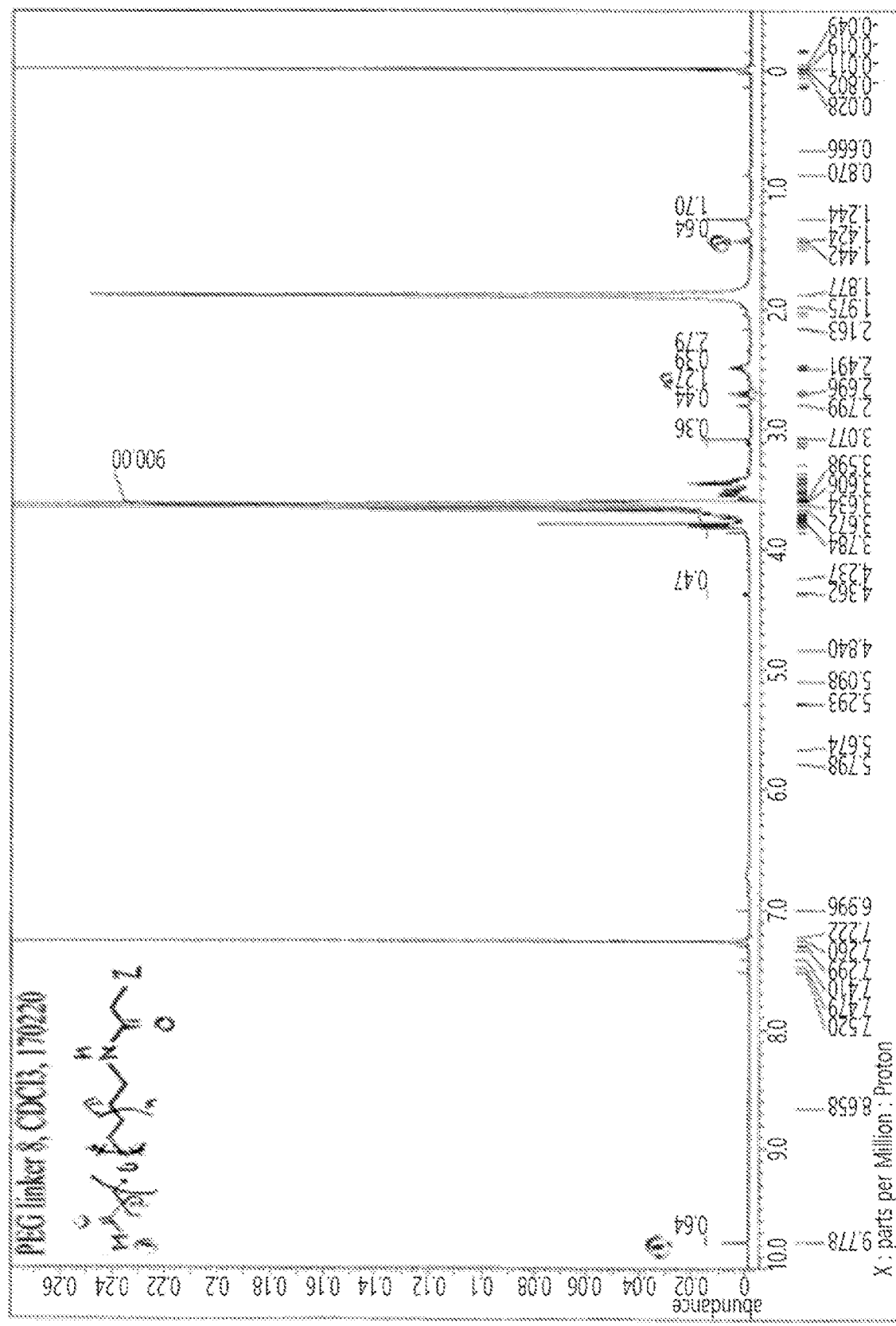
FIG. 12 shows the result of NMR analysis confirming linker #8 after its preparation.
Figure 13:
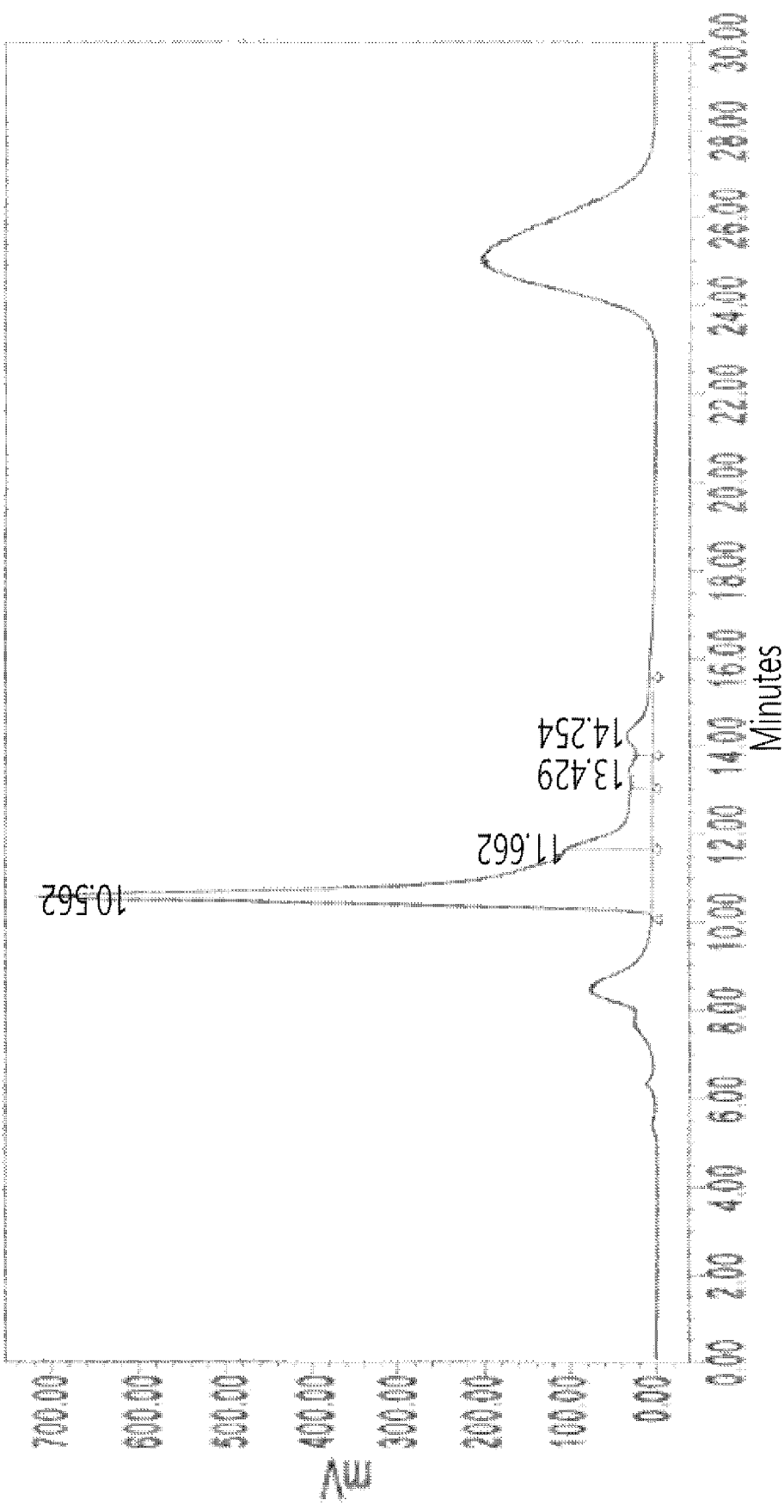
FIG. 13 shows the result of RPC analysis of linker #8 after its preparation.
Figure 14:
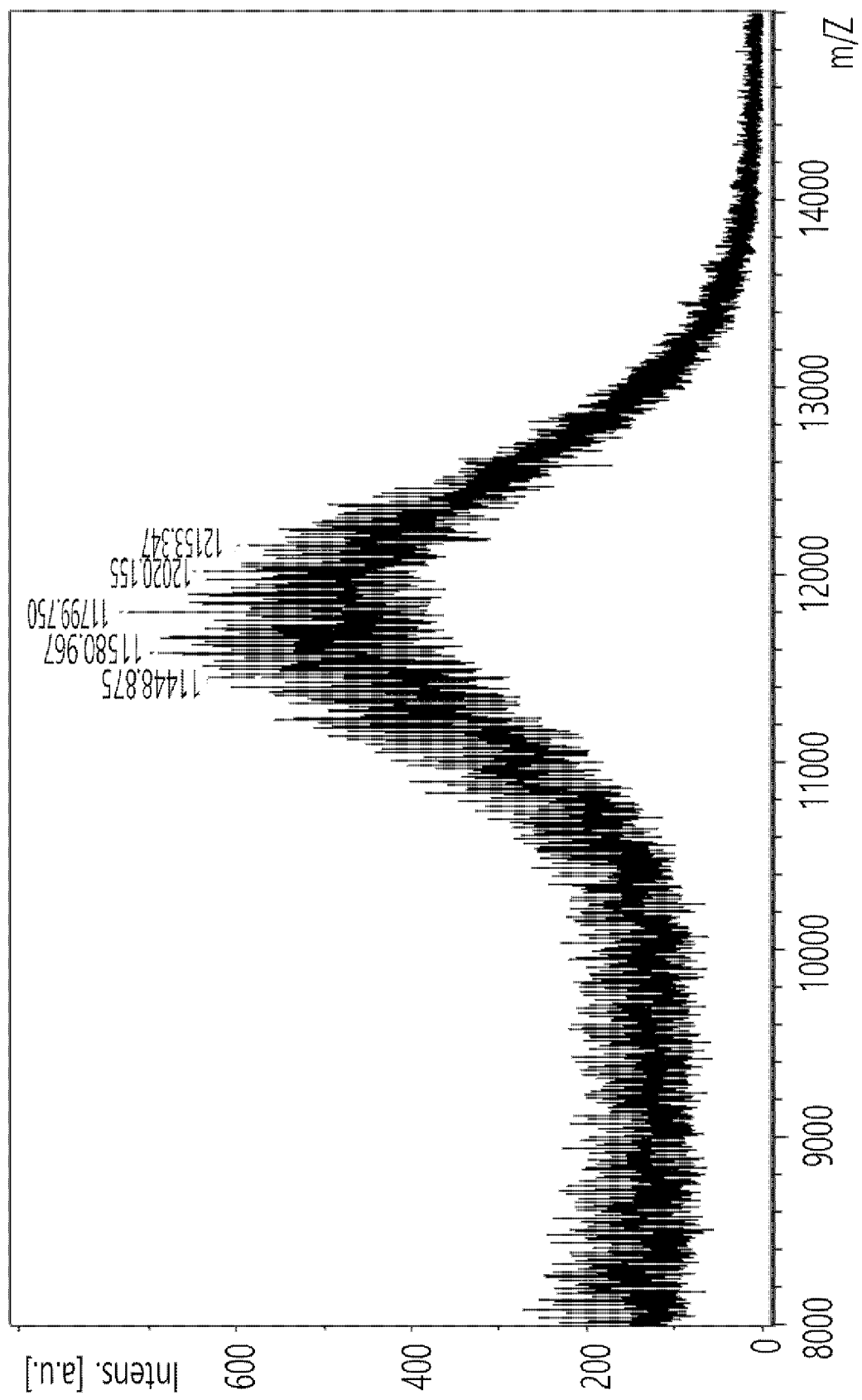
FIG. 14 shows the result of MALDI-TOF analysis of the molecular weight of linker #8 after its preparation.
Figure 15:
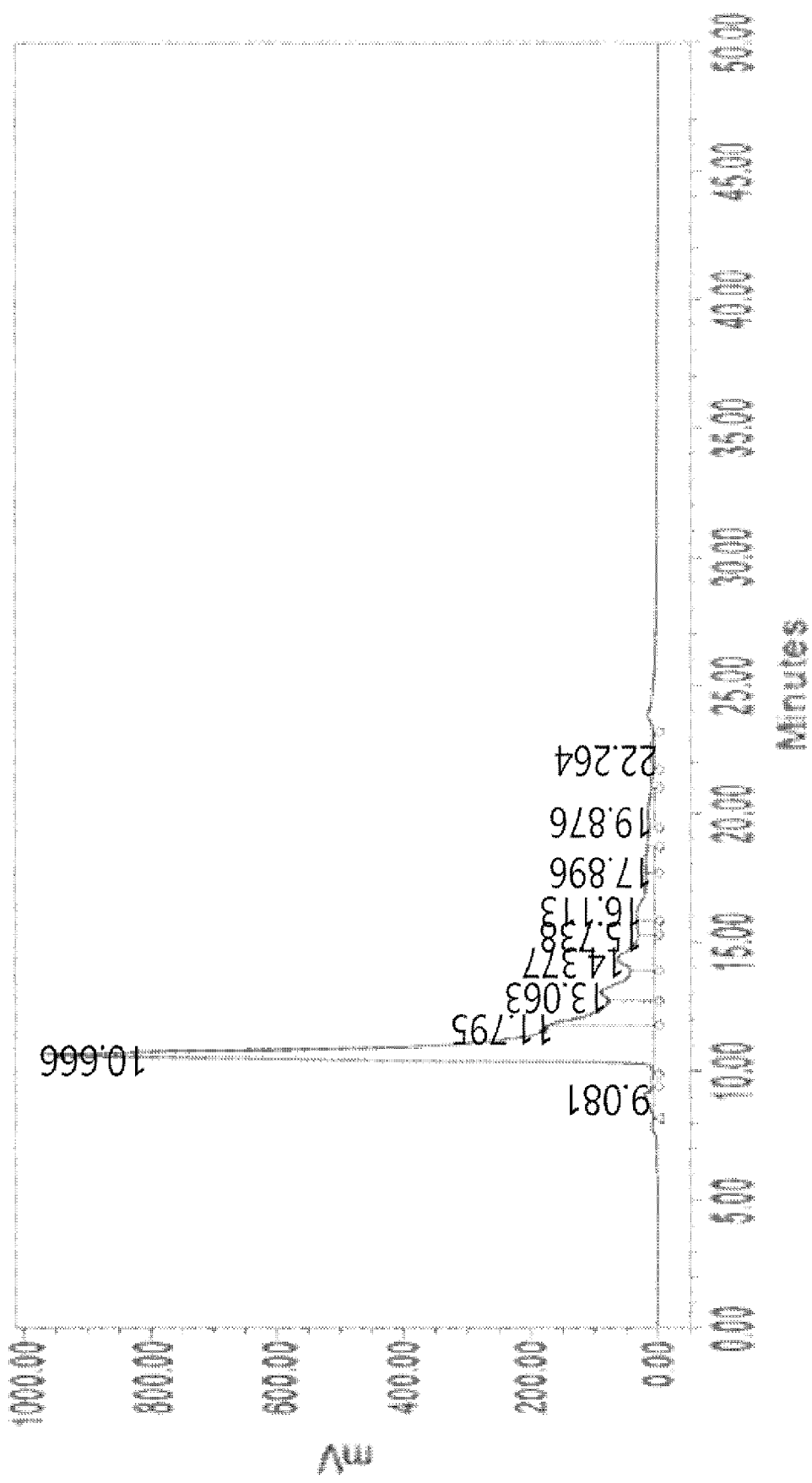
FIG. 15 shows the result of RPC analysis of linker #9 after its preparation.
Figure 16:
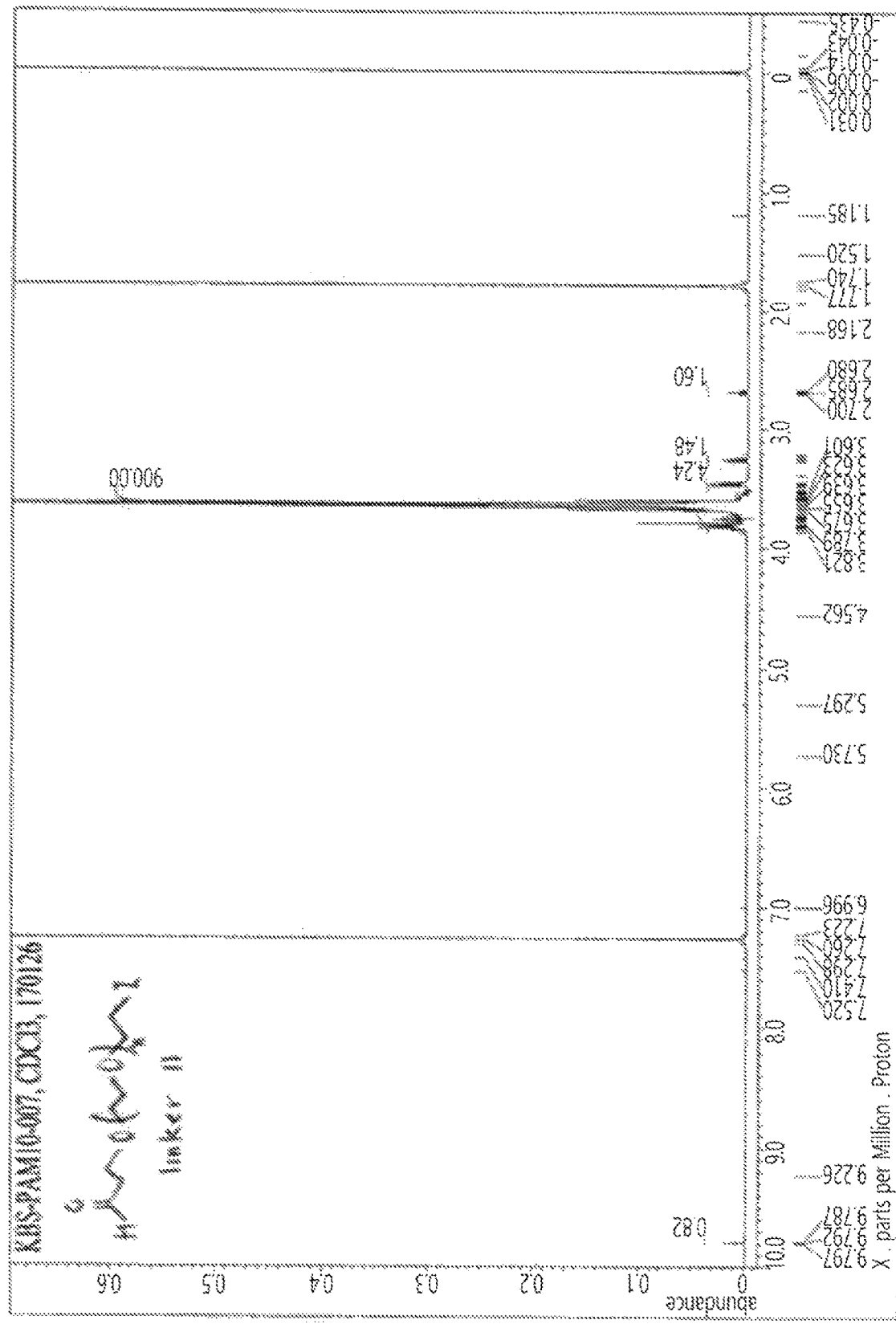
FIG. 16 shows the result of NMR analysis confirming linker #11 after its preparation.
Figure 17:
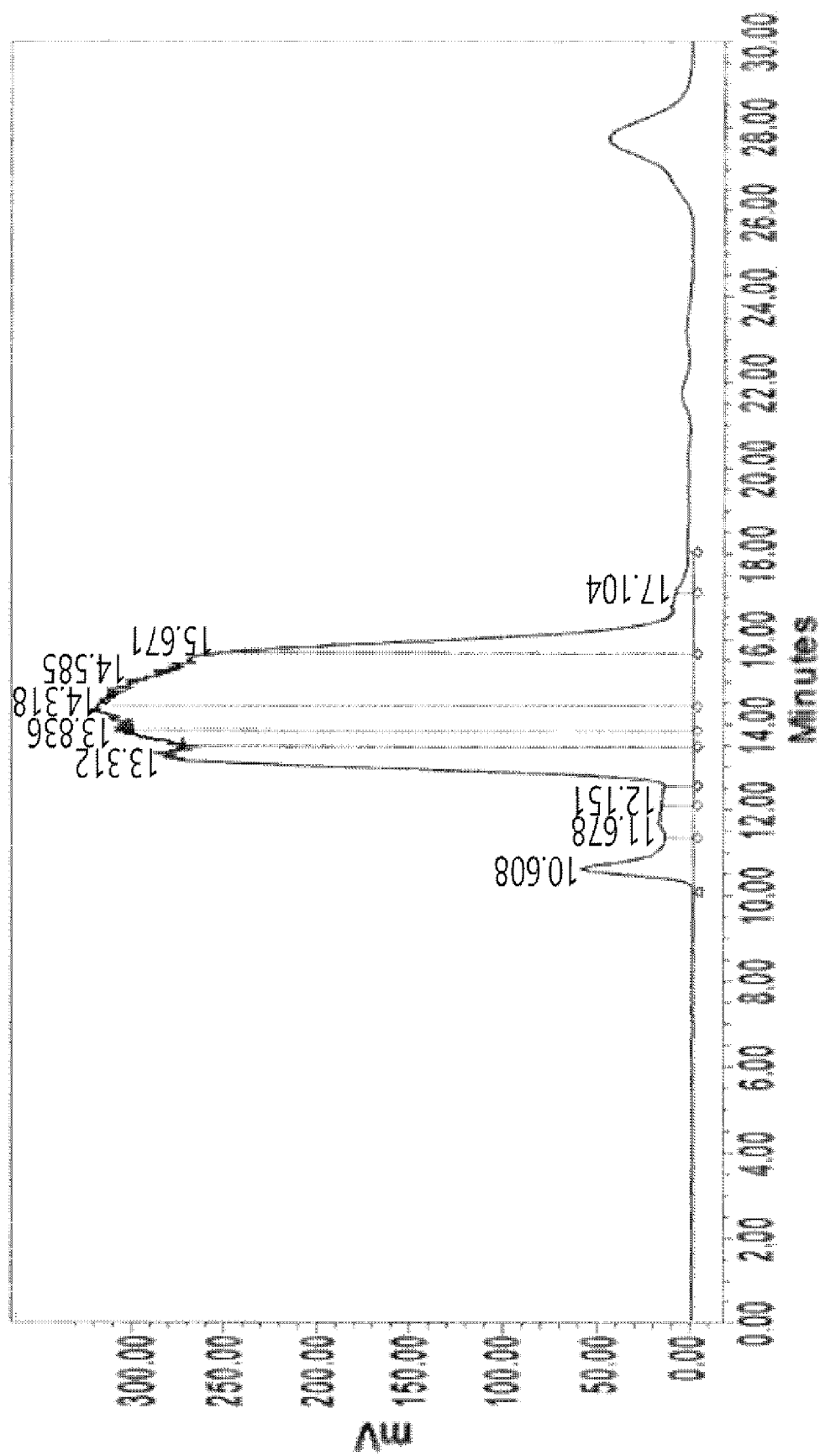
FIG. 17 shows the result of RPC analysis of linker #11 after its preparation.

An aspect of the present invention provides a polyethylene glycol compound, a stereoisomer thereof, or a pharmaceutically acceptable salt thereof.

Hereinafter, the present invention is described in detail. Meanwhile, each description and embodiment disclosed in the present invention may be applied herein to describe different descriptions and embodiments. In other words, all combinations of various components disclosed in the present invention are included within the scope of the present invention. Furthermore, the scope of the present invention should not be limited by the detailed description provided hereinbelow.

As used herein, the term "polyethylene glycol compound" refers to a compound including the structure of a polyethylene glycol, [—(OCH$_2$CH$_2$)$_n$—]. More specifically, in the present invention, the polyethylene glycol compound may include two reactive end groups.

In particular, the two or more reactive end groups present in the polyethylene glycol compound may be the same or different with each other. More specifically, the polyethylene glycol compound may be a heterofunctional linker that acts on mutually different reactive end groups. For example, one end of the compound may have a functionality on the amine group while the other end may have a functionality on the thiol group, but the polyethylene glycol compounds are not particularly limited thereto.

Additionally, the polyethylene glycol compound may be used as a linker for linking a carrier to a physiologically active polypeptide. Accordingly, one end of the polyethylene glycol compound, which has two or more reactive end groups, may be linked to a physiologically active polypeptide while the other end of the polyethylene glycol compound may be linked to a carrier.

Meanwhile, the polyethylene glycol compound and polyethylene glycol derivatives may be used interchangeably in the present invention.

In a specific embodiment, the polyethylene glycol compound according to the present invention may be one which includes the structure of —NHCO— between a thiol reactive group and the structure of a polyethylene glycol as shown below.

Specifically, the compound may be a compound represented by Formula 1 below:

[Formula 1]

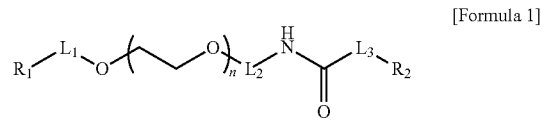

wherein, in Formula 1 above,

R$_1$ is selected from 2,5-dioxopyrrolidinyl, 2,5-dioxopyrrolyl, aldehyde, maleimide, C$_{6-20}$ aryl disulfide, C$_{5-20}$ heteroaryl disulfide, vinyl sulfone, thiol, halogenated acetamide, succinimide, p-nitrophenyl carbonate, and derivatives thereof, each of $L_1$ to $L_3$ is independently a linear or branched $C_{1-6}$ alkylene;

$R_2$ is ortho-pyridyl disulfide (OPSS), thiol, or halogen; and n is an integer of 10 to 2400.

In Formula 1 above, $R_2$ may be ortho-pyridyl disulfide, thiol, F, Br, Cl, or I, and more specifically, ortho-pyridyl disulfide or I, but is not particularly limited thereto.

In Formula 1 above, $R_1$ may be aldehyde, but is not particularly limited thereto.

In Formula 1 above, $R_1$ may be a succinimide derivative, and the kinds of the succinimide derivative may include succinimidyl propionate, hydroxy succinimidyl, succinimidyl carboxymethyl, and succinimidyl carbonate, but are not particularly limited thereto.

Additionally, the compound may be heterofunctional, acting on mutually different reactive end groups, and specifically, $R_1$ and $R_2$ may have mutually different functional groups, but the compound is not particularly limited thereto.

Specifically, $R_1$ may be aldehyde and $R_2$ may be ortho-pyridyl disulfide (OPSS), thiol, or halogen, but the compound is not particularly limited thereto.

In the above compound, each of $L_1$ to $L_3$ may be independently a linear or branched $C_{1-6}$ alkylene, and more specifically, $C_{1-4}$ alkylene, but is not particularly limited thereto.

For example, $L_1$ may be an integer of 1, 2, 3, 4, 5, or 6; $L_2$ may be an integer of 1, 2, 3, 4, 5, or 6; and $L_3$ may be an integer of 1, 2, 3, 4, 5, or 6.

In an embodiment, $L_2$ may be 2, 4, or 6, whereas $L_1$ and $L_3$ may be 1, 2, 3, 4, 5, or 6.

In the above compound, $R_1$-$L_1$- may be alkyl aldehyde, e.g., $C_{2-6}$ alkyl aldehyde, and specifically, propionaldehyde, butyraldehyde, etc., but is not particularly limited thereto.

Additionally, the polyethylene glycol compound of the present invention may have a molecular weight of about 100 dalton to about 110,000 dalton, specifically about 400 dalton to about 110,000 dalton, more specifically about 1,000 dalton to about 100,000 dalton, and even more specifically about 1,000 dalton to about 20,000 dalton, but is not particularly limited thereto.

In Formula 1 above, n may be an integer of 10 to 2400, and specifically an integer of 20 to 460, but is not particularly limited thereto.

Specifically, the compound may be a compound represented by Formula 2 below:

CHO—$(CH_2)_j$—O—$(CH_2CH_2O)_n$—$(CH_2)_m$—NH(CO)—$(CH_2)_k$—$R_2$     [Formula 2]

Wherein, in Formula 2 above, n is an integer of 10 to 2400, each of j, m, and k is independently an integer of 1 to 6, and $R_2$ is ortho-pyridyl disulfide, thiol, or halogen.

More specifically, in Formula 2 above, n may be an integer of 10 to 2400, and even more specifically an integer of 20 to 460, but is not particularly limited thereto.

In a specific embodiment, each of j, m, and k may be independently an integer of 1 to 6, and specifically an integer of 1 to 4.

For example, j may be an integer of 1, 2, 3, 4, 5, or 6; m may be an integer of 1, 2, 3, 4, 5, or 6; and k may be an integer of 1, 2, 3, 4, 5, or 6.

In an embodiment, j may be 2, 3, 4, 5, or 6; whereas m may be 2, 4, or 6; and k may be 1, 2, 3, 4, 5, or 6.

Additionally, $R_2$ may be ortho-pyridyl disulfide, thiol, or halogen; specifically ortho-pyridyl disulfide, thiol, or F, Br, Cl, or I; and more specifically ortho-pyridyl disulfide or I, but is not particularly limited thereto.

Specifically, the compound may be a compound selected from Formulas 6 to 11 below.

[Formula 6]

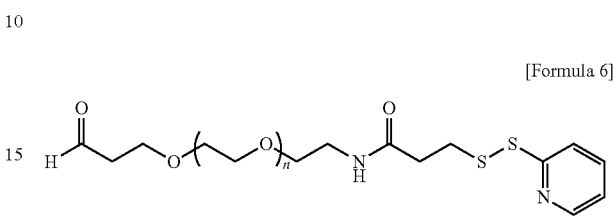

[Formula 7]

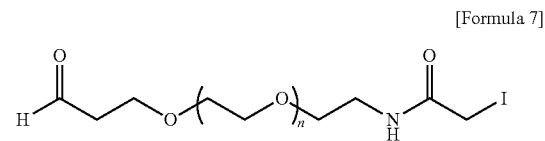

[Formula 8]

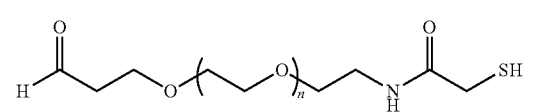

[Formula 9]

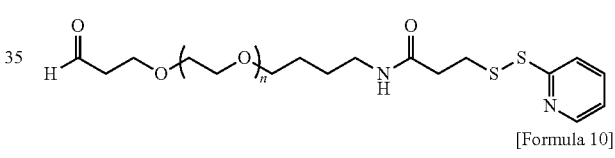

[Formula 10]

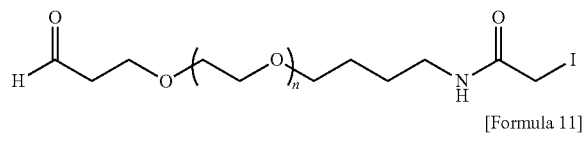

[Formula 11]

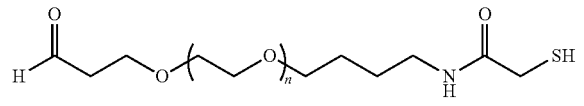

In Formulas 6 to 11, n is the same as defined above.

In Examples of the present invention, the compound represented by Formula 6 was named as linker #4; the compound represented by Formula 7 was named as linker #5; the compound represented by Formula 8 was named as linker #6; the compound represented by Formula 9 was named as linker #7; the compound represented by Formula 10 was named as linker #8; and the compound represented by Formula 11 was named as linker #9, respectively.

In an embodiment of the present invention, it was confirmed that the compounds belonging to Formula 1 above can exhibit a higher reactivity to a thiol group compared to the above compound which do not include —NHCO— structure. Therefore, the compounds belonging to Formula 1 above can be effectively used for attaching to materials including a thiol group.

Meanwhile, the compound may specifically have any one structure selected from Formulas 3 to 5 below:

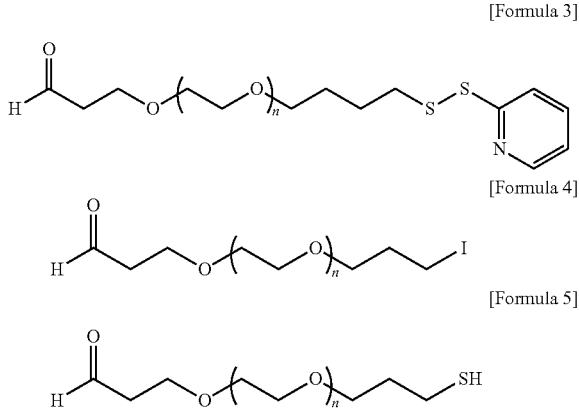

[Formula 3]

[Formula 4]

[Formula 5]

wherein n is the same as defined above.

Meanwhile, the compound may be present in the form of a pharmaceutically acceptable salt. As a salt, an acid addition salt formed by a pharmaceutically acceptable free acid is useful.

The kind of the salt is not particularly limited. However, the salt is preferably one that is safe and effective to a subject, e.g., a mammal, but is not particularly limited thereto.

The term "pharmaceutically acceptable" refers to a material which can be effectively used for the intended use within the scope of pharmaco-medical decision without inducing excessive toxicity, irritation, allergic responses, etc.

As used herein, the term "pharmaceutically acceptable salt" refers to a salt derived from pharmaceutically acceptable inorganic acids, organic acids, or bases. Examples of the suitable salts may include hydrochloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphthalene-2-sulfonic acid, benzenesulfonic acid, etc. Examples of the salts derived from suitable bases may include alkali metals such as sodium, potassium, etc.; alkali earth metals such as magnesium; ammonium, etc.

Acid addition salts may be prepared by a conventional method, for example, a method of dissolving a compound in an excess aqueous acid solution followed by precipitating the resulting salt using a water-miscible organic solvent (e.g., methanol, ethanol, acetone, or acetonitrile). An equimolar amount of the compound and the acid or alcohol in water (e.g., glycol monomethyl ether) may be heated, and subsequently, the mixture may be evaporated and dried or the educed salt may be subjected to suction filtration.

Additionally, a pharmaceutically acceptable metal salt may be prepared using a base. An alkali metal salt or alkali earth metal salt may be prepared, for example, by dissolving a compound in an excess amount of an alkali metal hydroxide or alkali earth metal hydroxide solution, filtering the non-dissolved compound salt, and evaporating the filtrate, followed by drying.

Additionally, the compound of the present invention and a pharmaceutically acceptable salt thereof is a concept which includes solvates that can be prepared therefrom.

As used herein, the term "solvate" refers to a complex which is formed between the compound according to the present invention or a salt thereof and a solvent molecule.

Furthermore, when the compound of the present invention has an asymmetric carbon center in its substituent, the compound may exist as an (R) or (S) isomer, a racemate, a mixture of a diastereomer, and an individual diastereomer, and all of these isomers and mixtures thereof belong to the scope of the present invention.

Still another aspect of the present invention provides a method for preparing a physiologically active polypeptide to which a polyethylene glycol compound is attached, which includes reacting a polyethylene glycol compound with a physiologically active polypeptide to prepare a physiologically active polypeptide to which a polyethylene glycol compound is attached.

The polyethylene glycol compounds are the same as explained above.

The above method may include linking any one of the reactive end groups, which are located at both ends of the polyethylene glycol compound, to a physiologically active polypeptide. More specifically, the reactive end group located at $R_1$ may be linked to the physiologically active polypeptide; or the reactive end group located at $R_2$ may be linked to the physiologically active polypeptide, but the method is not limited thereto.

More specifically, the method may include reacting orthopyridyl disulfide, thiol, or halogen, which are located at $R_2$, with a thiol group located at the cysteine residue of the physiologically active polypeptide, but the method is not limited thereto.

The reaction between the polyethylene glycol compound and physiologically active polypeptide may be appropriately determined by one of ordinary skill in the art, in consideration of the characteristics of the reactive end group of polyethylene glycol compound and the characteristics of the reactive groups of the physiologically active polypeptide, to which polyethylene glycol compound is to be linked.

For example, the reaction may be performed in the presence of a citrate buffer or HEPES buffer or an organic solvent such as $C_{1-6}$ alcohol, but is not particularly limited thereto.

Additionally, the method may further include purifying the physiologically active polypeptide to which a polyethylene glycol compound is attached.

For the purification, any known method in the art may be used without limitation, and specifically chromatography may be used, but the purification method is not particularly limited thereto.

As used herein, the term "physiologically active polypeptide" refers to a concept including peptides or proteins capable of exhibiting physiological activities, and preferably refers to materials whose physiological activities are to be exhibited in a subject.

The physiologically active polypeptide is to be selected from the group consisting of hormones, cytokines, enzymes, antibodies, growth factors, transcription factors, blood factors, vaccines, insulinotropic peptides, neuropeptides, pituitary hormones, anti-obesity peptides, antiviral peptides, non-native peptide derivatives having a physiological activity, structural proteins, ligand proteins, and receptors.

Examples of the physiologically active polypeptide may include GLP-1 receptor agonist, leptin receptor agonist, DPP-IV inhibitor, Y5 receptor antagonist, melanin-concentrating hormone (MCH) receptor antagonist, Y2/3 receptor agonist, MC3/4 receptor agonist, gastric/pancreatic lipase inhibitor, 5HT2c agonist, β3A receptor agonist, amylin receptor agonist, ghrelin antagonist, ghrelin receptor antagonist, etc., but are not particularly limited thereto.

Additionally, the physiologically active polypeptide may be a peptide which includes the amino acid sequence represented by the sequences below, or essentially consists of the sequences thereof, or consists of the sequences thereof. The peptide may have an activity on glucagon receptors, GLP-1 receptors, and GIP receptors, and these peptides are named as triple agonists.

(SEQ ID NO: 103)
Xaa1-Xaa2-Xaa3-Gly-Thr-Phe-Xaa7-Ser-Asp-Xaa10-Ser-

Xaa12-Xaa13-Xaa14-Xaa15-Xaa16-Xaa17-Xaa18-Xaa19-

Xaa20-Xaa21-Phe-Xaa23-Xaa24-Trp-Leu-Xaa27-Xaa28-

Xaa29-Xaa30-$R_1$

In the Formula above,
Xaa1 is histidine, 4-imidazoacetyl, or tyrosine,
Xaa2 is glycine, α-methyl-glutamic acid, or Aib,
Xaa3 is glutamic acid or glutamine,
Xaa7 is threonine or isoleucine,
Xaa10 is leucine, tyrosine, lysine, cysteine, or valine,
Xaa12 is lysine, serine, or isoleucine,
Xaa13 is glutamine, tyrosine, alanine, or cysteine,
Xaa14 is leucine, methionine, or tyrosine,
Xaa15 is cysteine, aspartic acid, glutamic acid, or leucine,
Xaa16 is glycine, glutamic acid, or serine,
Xaa17 is glutamine, arginine, isoleucine, glutamic acid, cysteine, or lysine,
Xaa18 is alanine, glutamine, arginine, or histidine,
Xaa19 is alanine, glutamine, cysteine, or valine,
Xaa20 is lysine, glutamine, or arginine,
Xaa21 is glutamic acid, glutamine, leucine, cysteine, or aspartic acid,
Xaa23 is isoleucine or valine,
Xaa24 is alanine, glutamine, cysteine, asparagine, aspartic acid, or glutamic acid,
Xaa27 is valine, leucine, lysine, or methionine,
Xaa28 is cysteine, lysine, alanine, asparagine, or aspartic acid,
Xaa29 is cysteine, glycine, glutamine, threonine, glutamic acid, or histidine,
Xaa30 is cysteine, glycine, lysine, or histidine, or is absent, and
$R_1$ is cysteine, GKKNDWKHNIT (SEQ ID NO: 104), m-SSGAPPPS-n (SEQ ID NO: 105), or m-SSGQPPPS-n (SEQ ID NO: 106), or is absent,
wherein:
m is -Cys-, -Pro-, or -Gly-Pro-, and
n is -Cys-, -Gly-, -Ser-, or -His-Gly-, or is absent.

Examples of the triple agonists may include a peptide including the amino acid sequence selected from SEQ ID NOS: 1 to 102, but are not particularly limited thereto.

Additionally, the physiologically active polypeptide may be selected from selected from the group consisting of glucagon; insulin; somatostatin; peptide YY (PYY); neuropeptide Y (NPY); glucagon-like peptides including glucagon-like peptide-1 (GLP-1) and glucagon-like peptide-2 (GLP-2); exendin-3; exendin-4; oxyntomodulin; peptides having an activity on glucagon receptors, GLP-1 receptors, and GIP receptors; fibroblast growth factor; ghrelin; angiotensin; bradykinin; calcitonin; corticotropin; eledoisin; gastrin; leptin; oxytocin; vasopressin; luteinizing hormone; luteotropin; follicle-stimulating hormone; parathyroid hormone; secretin; sermorelin; human growth hormone (hGH); growth hormone-releasing peptides; granulocyte-colony-stimulating factors (GCSF); interferons (IFNs); interleukins; prolactin-releasing peptides; orexin; thyroid-releasing peptides; cholecystokinin; gastrin inhibitory peptides; calmodulin; gastric-releasing peptides; motilin; vasoactive intestinal peptides; atrial natriuretic peptides (ANPs); B-type natriuretic peptides (BNPs); C-type natriuretic peptides (CNPs); neurokinin A; neuromedin; renin; endothelin; sarafotoxin peptide; carsomorphin peptide; dermorphin; dynorphin; endorphin; enkepalin; T cell factors; tumor necrosis factor; tumor necrosis factor receptors; urokinase receptors; tumor inhibitory factors; collagenase inhibitors; thymopoietin; thymulin; thymopentin; thymosin; thymic humoral factor; adrenomedullin; allatostatin; amyloid β-protein fragments; antibacterial peptides; antioxidant peptides; bombesin; osteocalcin; CART peptides; E-selectin; ICAM-1; VCAM-1; leucokine; kringle-5; laminin; inhibin; galanin; fibronectin; pancreastatin; fuzeon; interferon receptors; G protein-coupled receptors; interleukin receptors; enzymes; interleukin-binding proteins; cytokine-binding proteins; macrophage-activating factors; macrophage peptides; B cell factor; protein A; allergy inhibitors; cell necrosis glycoprotein; immunotoxin; lymphotoxin; tumor inhibitory factors; metastasis growth factors; α-1-antitrypsin; albumin; α-lactalbumin; apolipoprotein-E; erythropoietin; highly glycosylated erythropoietin; angiopoietins; hemoglobin; thrombin; thrombin receptor-activating peptides; thrombomodulin; blood factors VII, VIIa, VIII, IX, and XIII; plasminogen-activating factors; fibrin-binding peptides; urokinase; streptokinase; hirudin; protein C; C-reactive protein; renin inhibitors; superoxide dismutase; platelet-derived growth factors; epidermal growth factors; epithelial cell growth factors; angiostatin; angiotensin; osteogenic growth factors; osteogenesis-promoting proteins; atriopeptin; cartilage-inducing factors; elcatonin; connective tissue-activating factors; tissue factor pathway inhibitors; luteinizing hormone-releasing hormone; nerve growth factors; relaxin; somatomedin; insulin-like growth factor; adrenocortical hormone; pancreatic polypeptides; gastrin-releasing peptides; corticotropin-releasing factor; thyroid-stimulating hormone; autotoxin; lactoferrin; myostatin; cell surface antigens; virus-derived vaccine antigens; monoclonal antibody; polyclonal antibody; antibody fragments; erythropoietic growth factors; leukopoietin; amylin; and analogs thereof, but is not particularly limited thereto.

Still another aspect of the present invention provides a method for preparing a conjugate, in which a physiologically active polypeptide and a carrier protein are linked by a polyethylene glycol compound.

The physiologically active polypeptide and polyethylene glycol compound are the same as explained above.

Specifically, the method may include:
(a) reacting the polyethylene glycol compound with any one of a physiologically active polypeptide or carrier protein, thereby preparing a polyethylene glycol compound, wherein the physiologically active polypeptide or carrier protein is attached to one end of the polyethylene glycol compound and the other end of the polyethylene glycol compound has a reactive end group; and
(b) reacting the polyethylene glycol compound prepared in step (a) above, wherein the physiologically active polypeptide or carrier protein is attached to one end of the polyethylene glycol compound and the other end of the polyethylene glycol compound has a reactive end group, with the other one of the physiologically active polypeptide or carrier protein, so as to link the carrier protein or physiologically active polypeptide to the reactive end group of the polyethylene glycol compound, thereby preparing a conjugate in which the physiologically active polypeptide and the carrier protein are linked by a polyethylene glycol compound.

More specifically, the method may include:

(a) reacting the polyethylene glycol compound with a physiologically active polypeptide, thereby preparing a polyethylene glycol compound, wherein the physiologically active polypeptide is attached to one end of the polyethylene glycol compound and the other end of the polyethylene glycol compound has a reactive end group; and (b) reacting the polyethylene glycol compound prepared in step (a) above, wherein the physiologically active polypeptide is attached to one end of the polyethylene glycol compound and the other end of the polyethylene glycol compound has a reactive end group, with a carrier protein, so as to link the carrier protein to the reactive end group of the polyethylene glycol compound.

Specifically, the polyethylene glycol compound in step (a) may have a structure of Formula 1 below.

[Formula 1]

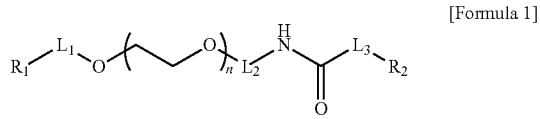

In Formula 1 above, $R_1$ is aldehyde;

each of $L_1$ to $L_3$ is independently a linear or branched $C_{1-6}$ alkylene;

$R_2$ is ortho-pyridyl disulfide (OPSS), thiol, or halogen; and n is an integer of 10 to 2400.

In the above method, the reaction between the polyethylene glycol compound and the physiologically active polypeptide may include a reaction between the $R_2$ of the polyethylene glycol compound with the thiol group located at the cysteine residue of the physiologically active polypeptide, and the reaction between the polyethylene glycol compound and the carrier protein may include a reaction between the aldehyde end group of the polyethylene glycol compound and the amine group of the carrier protein, although the reactions are not particularly limited thereto.

Specifically, in the above method, step (a) may be reacting $R_2$ of the polyethylene glycol compound having the structure of Formula 1 above with the thiol group located at the cysteine residue of the physiologically active polypeptide, whereas step (b) may be reacting the aldehyde end group of the polyethylene glycol compound with the amine group of the carrier protein.

The reaction between the polyethylene glycol compound and the physiologically active polypeptide or the carrier protein may be appropriately determined by one of ordinary skill in the art, in consideration of the characteristics of the reactive groups of the polyethylene glycol compound and the characteristics of the reactive groups of the physiologically active polypeptide or the carrier protein, to which the polyethylene glycol compound is to be linked.

For example, the PEGylation reaction may be performed in the presence of an appropriate buffer such as citrate buffer or HEPES or an organic solvent such as $C_{1-6}$ alcohol, but the buffer and the solvent are not particularly limited thereto.

Additionally, the aldehyde reactive group selectively reacts with the amino terminal in a low pH condition, and may form a covalent bond with a lysine residue in a high pH condition, (e.g., pH 9.0).

Meanwhile, the carrier protein may be a material which is linked to the physiologically active polypeptide by the polyethylene glycol compound for the purpose of increasing the in vivo half-life of the physiologically active polypeptide.

The carrier protein may be albumin and a fragment thereof, a polymer of a repeating unit of a particular amino acid sequence, antibody, an antibody fragment, an FcRn-binding material, fibronectin, transferrin, saccharide, or elastin, and the FcRn-binding material may be an immunoglobulin Fc fragment, but is not particularly limited thereto.

In a specific embodiment, the end aldehyde group of the polyethylene glycol compound may be one which reacts with the amine group of an immunoglobulin Fc fragment, and specifically the amine group of the N-terminus, but is not particularly limited thereto.

In the present invention, "immunoglobulin Fc region" refers to a region including the heavy chain constant region 2 (CH2) and/or the heavy chain constant region 3 (CH3), excluding the heavy chain and light chain variable regions of an immunoglobulin. The immunoglobulin Fc region may be one constitution that establishes a moiety of a protein conjugate of the present invention.

The immunoglobulin Fc region may include a hinge region in the heavy chain constant region, but is not limited thereto. Additionally, the immunoglobulin Fc region of the present invention may be an extended Fc region including a part or the entirety of the heavy chain constant region 1 (CH1) and/or the light chain constant region 1 (CL1), excluding the heavy chain and the light chain variable regions of the immunoglobulin, as long as the immunoglobulin Fc region has an effect substantially the same as or improved compared to the native type. Additionally, the immunoglobulin Fc region of the present invention may be a region in which a fairly long part of the amino acid sequence corresponding to CH2 and/or CH3 is removed.

For example, the immunoglobulin Fc region of the present invention may be 1) a CH1 domain, a CH2 domain, a CH3 domain, and a CH4 domain; 2) a CH1 domain and a CH2 domain; 3) a CH1 domain and a CH3 domain; 4) a CH2 domain and a CH3 domain; 5) a combination between one or two or more domains among a CH1 domain, a CH2 domain, a CH3 domain, and a CH4 domain and an immunoglobulin hinge region (or a part of the hinge region); and 6) a dimer between each domain of the heavy chain constant region and the light chain constant region, but is not limited thereto.

Additionally, in a specific embodiment, the immunoglobulin Fc region may be in a dimeric form and one molecule of X may be covalently linked to one Fc region in a dimer form, where the immunoglobulin Fc and X may be linked to each other by a polyethylene glycol compound. Meanwhile, it is also possible that two molecules of X are symmetrically linked to one Fc region in a dimeric form, where the immunoglobulin Fc and X may be linked to each other by a polyethylene glycol compound. However, the linkage is not limited thereto.

Additionally, the immunoglobulin Fc region of the present invention not only includes a native amino acid sequence but also a sequence derivative thereof. An amino acid sequence derivative refers to an amino acid sequence which has a difference in at least one amino acid residue due to deletion, insertion, non-conservative or conservative substitution, or a combination thereof.

For example, the amino acid residues at positions 214 to 238, 297 to 299, 318 to 322, or 327 to 331, which are known to be important in the conjugation of an immunoglobulin Fc, may be used as suitable sites for modification.

Additionally, other various derivatives are possible, including one that has a deletion of a region capable of forming a disulfide bond, or a deletion of some amino acid residues at the N-terminus of native Fc or an addition of a methionine residue at the N-terminus of native Fc, etc. Furthermore, to remove effector functions, a deletion may occur in a complement-binding site, such as a C1q-binding site and an antibody dependent cell mediated cytotoxicity (ADCC) site. Techniques of preparing such sequence derivatives of the immunoglobulin Fc region are disclosed in International Patent Publication Nos. WO 97/34631, WO 96/32478, etc.

Amino acid exchanges in proteins and peptides, which do not entirely alter the activities of molecules, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly. Depending on the cases, the Fc region may be modified by phosphorylation, sulfation, acrylation, glycosylation, methylation, farnesylation, acetylation, amidation, etc.

The above-described Fc derivatives show a biological activity identical to that of the Fc region of the present invention and they may have improved structural stability against heat, pH, etc.

Further, the immunoglobulin Fc region may be obtained from native forms isolated in vivo from humans or animals such as cows, goats, pigs, mice, rabbits, hamsters, rats, guinea pigs, etc., or may be recombinants or derivatives thereof obtained from transformed animal cells or microorganisms. Herein, the Fc region may be obtained from a native immunoglobulin by isolating a whole immunoglobulin from a living human or animal body and treating the isolated immunoglobulin with protease. When the whole immunoglobulin is treated with papain, it is cleaved into Fab and Fc regions, whereas when the whole immunoglobulin is treated with pepsin, it is cleaved into pF'c and F(ab)$_2$ fragments. Fc or pF'c can be isolated using size-exclusion chromatography, etc. In a more specific embodiment, a human-derived Fc region is a recombinant immunoglobulin Fc region obtained from a microorganism.

Additionally, the immunoglobulin Fc region may be in the form of a natural glycan, increased or decreased glycan compared to the natural type, or in a deglycosylated form. The increase, decrease, or removal of the immunoglobulin Fc glycan may be achieved by conventional methods such as a chemical method, enzymatic method, and genetic engineering method using a microorganism. The immunoglobulin Fc region obtained by removal of a glycan from the Fc region shows a significant decrease in binding affinity to the C1q part and a decrease or loss in antibody-dependent cytotoxicity or complement-dependent cytotoxicity, and thus it does not induce unnecessary immune responses in vivo. In this regard, an immunoglobulin Fc region in a deglycosylated or aglycosylated immunoglobulin Fc region may be a more suitable form to meet the original object of the present invention as a drug carrier.

As used herein, the term "deglycosylation" refers to enzymatically removing sugar moieties from an Fc region, and the term "aglycosylation" refers to an unglycosylated Fc region produced in prokaryotes, in a more specific embodiment, E. coli.

Meanwhile, the immunoglobulin Fc region may be derived from humans or other animals including cows, goats, pigs, mice, rabbits, hamsters, rats, and guinea pigs. In a more specific embodiment, it is of human origin.

Additionally, the immunoglobulin (Ig) Fc region may be derived from IgG, IgA, IgD, IgE, IgM, or a combination or hybrid thereof. In a more specific embodiment, it is derived from IgG or IgM, which are among the most abundant proteins in human blood, and in an even more specific embodiment, it is derived from IgG, which is known to enhance the half-lives of ligand-binding proteins. In a yet even more specific embodiment, the immunoglobulin Fc region is an IgG4 Fc region, and in the most specific embodiment, the IgG4 Fc region is an aglycosylated Fc region derived from human IgG4, but is not limited thereto.

In particular, as used herein, the term "combination" means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

Additionally, the above method may further include purifying a conjugate, in which a physiologically active polypeptide and a carrier protein are linked by a polyethylene glycol compound.

For the purification, any known method in the art may be used without limitation, and specifically chromatography may be used, but the purification method is not particularly limited thereto.

Still another aspect of the present invention provides a physiologically active polypeptide, to which the polyethylene glycol compound is attached.

The polyethylene glycol compound and physiologically active polypeptide are the same as explained above.

In a specific embodiment, the physiologically active polypeptide may be one which includes the structure represented by any of Formulas 15 to 17:

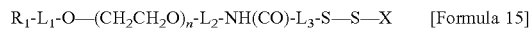
$$R_1\text{-}L_1\text{-}O\text{---}(CH_2CH_2O)_n\text{-}L_2\text{-}NH(CO)\text{-}L_3\text{-}S\text{---}S\text{---}X \quad \text{[Formula 15]}$$

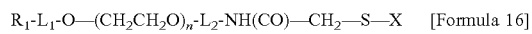
$$R_1\text{-}L_1\text{-}O\text{---}(CH_2CH_2O)_n\text{-}L_2\text{-}NH(CO)\text{---}CH_2\text{---}S\text{---}X \quad \text{[Formula 16]}$$

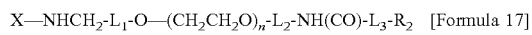
$$X\text{---}NHCH_2\text{-}L_1\text{-}O\text{---}(CH_2CH_2O)_n\text{-}L_2\text{-}NH(CO)\text{-}L_3\text{-}R_2 \quad \text{[Formula 17]}$$

wherein, in Formulas 15 to 17, $R_1$ is selected from 2,5-dioxopyrrolidinyl, 2,5-dioxopyrrolyl, aldehyde, maleimide, $C_{6\text{-}20}$ aryl disulfide, $C_{5\text{-}20}$ heteroaryl disulfide, vinyl sulfone, thiol, halogenated acetamide, succinimide, p-nitrophenyl carbonate, and derivatives thereof, each of $L_1$ to $L_3$ is independently a linear or branched $C_{1\text{-}6}$ alkylene;

n is an integer of 10 to 2400;

$R_2$ is ortho-pyridyl disulfide (OPSS), thiol, or halogen; and

X corresponds to a physiologically active polypeptide moiety.

All of the explanations provided previously will apply to the specific features and combinations of the variables described above.

The "—S—S—X" in Formula 15 above may be a structure formed by the reaction between the thiol group located at X and the ortho-pyridyl disulfide or thiol group; and the "—CH$_2$—S—X" in Formula 16 may be a structure formed by the reaction between the thiol group located at X and a halogen, and specifically iodoacetamide (IA); and the "X—NHCH$_2$—" in Formula 16 may be a structure formed by the reaction between the amine group located at X and an aldehyde group through reductive alkylation, but the structures are not particularly limited thereto.

Still another aspect of the present invention provides a conjugate, in which each of a physiologically active polypeptide and a carrier protein is independently attached to reactive groups at both ends of the polyethylene glycol compound.

The polyethylene glycol compound, physiologically active polypeptide, and carrier protein are the same as explained above.

In a specific embodiment, the conjugate has a structure represented by Formula 18 or 19 below:

Y—NHCH$_2$-L$_1$-O—(CH$_2$CH$_2$O)$_n$-L$_2$-NH(CO)-L$_3$-S—S—X  [Formula 18]

Y—NHCH$_2$-L$_1$-O—(CH$_2$CH$_2$O)$_n$-L$_2$-NH(CO)—CH$_2$—S—X  [Formula 19]

wherein, in Formulas 18 and 19 above,
each of L$_1$ to L$_3$ is independently a linear or branched C$_{1-6}$ alkylene;
n is an integer of 10 to 2400;
X is a physiologically active polypeptide moiety; and
Y is a carrier protein moiety.

Still another aspect of the present invention provides a method for preparing the polyethylene glycol compound.

The polyethylene glycol compound is the same as explained above.

Specifically, the method may include:

(a) introducing R$_1$ selected from the group consisting of 2,5-dioxopyrrolidinyl, 2,5-dioxopyrrolyl, aldehyde, maleimide, C$_{6-20}$ aryl disulfide, C$_{5-20}$ heteroaryl disulfide, vinyl sulfone, thiol, halogenated acetamide, succinimide, p-nitrophenyl carbonate, and derivatives thereof, to one end of a polyethylene glycol; and (b) introducing the structure of —NH(CO)L$_3$-R$_2$ to the other end of the polyethylene glycol, wherein R$_2$ is orthopyridyl disulfide (OPSS), thiol, or halogen.

As a non-limiting method, the method may include:
a first step for preparing a compound represented by Formula 21 below from a compound represented by Formula 20 below;
a second step for preparing a compound represented by Formula 22 below from a compound represented by Formula 21 below; and
a third step for converting the diethoxy methyl at an end of a compound represented by Formula 22 below into aldehyde by treating the compound represented by Formula 22 with an acid solution:

[Formula 20]

wherein, in Formula 20 above, n' is n or n+1; and

[Formula 21]

[Formula 22]

wherein L$_1$, L$_2$, L$_3$, n, and R$_2$ are the same as described above.

In a case where a polyethylene glycol compound, where L$_2$ is 2 as in linker #5 (Formula 7), n' may be n+1.

In the above method, the compound represented by Formula 20 of the first step may be one which is prepared by reacting the compound represented by Formula 23 with methanesulfonyl chloride:

[Formula 23]

In a case where a polyethylene glycol compound, where L$_2$ is 2 as in linker #5 (Formula 7), the first step may be performed by reacting the compound represented by Formula 20 with an aqueous ammonia solution and ammonium chloride.

Meanwhile, in cases where a polyethylene glycol compound, where L$_2$ is 3 or higher as in linkers #7 to #9 (Formulas 9 to 11), etc., the method may include:

step 1-1, which is to react a compound represented by Formula 20 with hydroxyalkyl tetrahydropyranyl ether, thereby preparing a compound represented by Formula 24;

step 1-2, which is to react a compound represented by Formula 24 with p-toluenesulfonic acid, thereby substituting the tetrahydropyranyloxy group at an end thereof with a hydroxy group;

step 1-3, which is to react the compound obtained in step 1-2 with methanesulfonyl chloride, thereby substituting the hydroxy group with a methanesulfonic acid group; and step 1-4, which is to react the compound obtained in step 1-3 with an aqueous ammonia solution and ammonium chloride:

[Formula 24]

wherein step 1-1 may be performed in the presence of potassium t-pentoxide.

Additionally, in a case where OPSS is introduced as a reactive end group, the second step may be performed by reacting a compound represented by Formula 21 with a compound represented by Formula 25.

[Formula 25]

Meanwhile, in a case where —I or —SH is introduced as a reactive end group, the second step may be performed by reacting a compound represented by Formula 21 with chloro (C$_2$ to C$_7$ alkanoyl) chloride, thereby synthesizing a compound comprising a chloro group at an end thereof, which is represented by Formula 26 below, as an intermediate product; and reacting the compound represented by Formula 26 with a halogen metal salt in the presence or absence of hydrogen sulfide, thereby converting the chloro group into thiol or halogen.

[Formula 26]

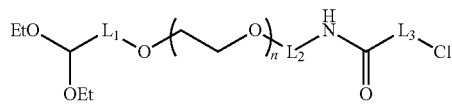

Still another aspect of the present invention provides a use of the polyethylene glycol compound for linking a carrier, which is capable of increasing an in vivo half-life of a physiologically active polypeptide, to a physiologically active polypeptide.

The physiologically active polypeptide, carrier, and polyethylene glycol compound are the same as explained above.

Still another aspect of the present invention provides a composition containing a physiologically active polypeptide to which the polyethylene glycol compound is attached or the conjugate.

The physiologically active polypeptide, conjugate, and polyethylene glycol compound are the same as explained above.

The composition may be a pharmaceutically acceptable composition and may contain a pharmaceutically acceptable carrier. The pharmaceutically acceptable carrier may include, for oral administration, a binder, a lubricant, a disintegrant, an excipient, a solubilizing agent, a dispersant, a stabilizing agent, a suspending agent, a coloring agent, a flavoring agent, etc.; for injections, a buffering agent, a preserving agent, an analgesic, a solubilizing agent, an isotonic agent, a stabilizing agent, etc., which may be combined for use; and for topical administrations, a base, an excipient, a lubricant, a preserving agent, etc. The formulation type of the pharmaceutical composition of the present invention may be prepared variously by combining with a pharmaceutically acceptable carrier described above. For example, for oral administration, the composition may be formulated into tablets, troches, capsules, elixirs, suspensions, syrups, wafers, etc. For injections, the composition may be formulated into unit-dose ampoules or multi-dose forms. The composition may also be formulated into solutions, suspensions, tablets, pills, capsules, sustained-release formulations, etc.

Meanwhile, examples of suitable carriers, excipients, and diluents may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. Additionally, the composition may further contain a filler, an anti-coagulant, a lubricant, a humectant, a flavoring agent, a preserving agent, etc.

Still another aspect of the present invention provides a polyethylene glycol compound linker for linking a carrier, which is capable of increasing an in vivo half-life of a physiologically active polypeptide, to a physiologically active polypeptide.

The physiologically active polypeptide, carrier, and polyethylene glycol compound are the same as explained above.

The compounds of the present invention may be synthesized by a series of reactions represented by Reaction Scheme below. However, the Formulas below are merely illustrative examples of the methods for preparing the compounds of the present invention, and thus the compounds of the present invention should not be limited by these methods and the preparation of these compounds may be prepared by a method known in the art or may be performed after an appropriate modification thereof.

[Reaction Scheme]

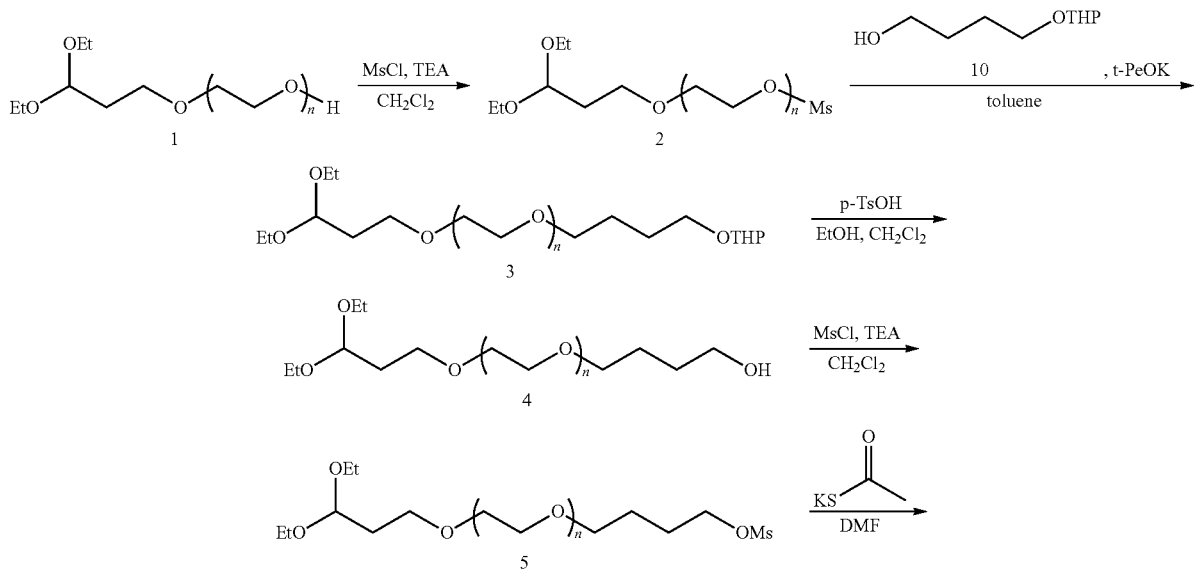

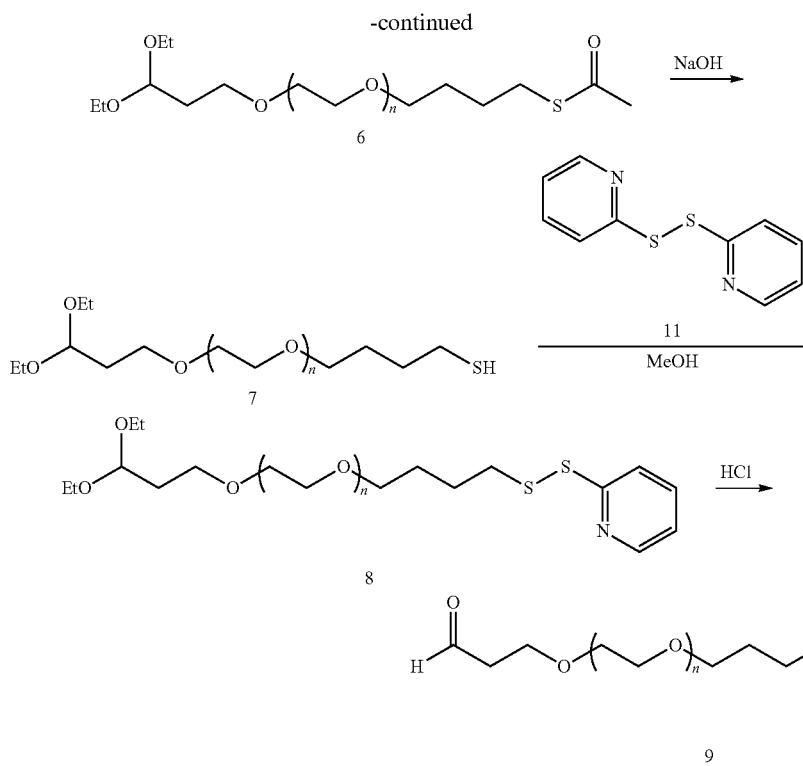

<Reaction Example 1> Preparation of Compound No. 2

Compound No. 1 and dichloromethane are added into a reaction container. While maintaining the reaction temperature at 10° C. or below, triethylamine and methanesulfonyl chloride are added thereto and stirred at room temperature for 3 hours. Upon completion of the reaction, water and dichloromethane are added thereto and stirred for 5 minutes. After extracting the resulting organic layer, dichloromethane is again added to the resulting aqueous layer and the extraction is performed once more. The organic layers are combined, washed with distilled water, dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 2.

<Reaction Example 2> Preparation of Compound No. 3

Toluene and Compound No. 10 are added into a reaction container. After adding potassium t-pentoxide thereto, the mixture is heated to about 50° C. and stirred at 50° C. for 1 hour (an activation solution). Compound No. 2 and toluene are added into another container. The activation solution is cooled to room temperature and added dropwise to the mixed solution at 30° C. for 1 hour. After stirring at 30° C. for 3 hours, water is added to the reaction solution and the extraction is performed. After separation of layers, dichloromethane is added to the resulting aqueous layer and the mixture is extracted. Dichloromethane is again added to the aqueous layer and the mixture is extracted once more. The resulting organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 3.

<Reaction Example 3> Preparation of Compound No. 4

Compound No. 3, ethanol, and dichloromethane are added into a reaction container. p-Toluene sulfonic acid (p-TsOH) is added thereto and stirred at room temperature for 20 hours. Sodium hydroxide is added thereto and the solvent is concentrated under reduced pressure. Dichloromethane and water are added thereto and stirred for 5 minutes. The organic layer is extracted therefrom and washed with water. The organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 4.

<Reaction Example 4> Preparation of Compound No. 5

Compound No. 4 and dichloromethane are added into a reaction container. While maintaining the reaction temperature at 10° C. or below, triethylamine and methanesulfonyl chloride are added thereto and stirred at room temperature for 3 hours. Upon completion of the reaction, water and dichloromethane are added thereto and stirred for 5 minutes. After extracting the organic layer, dichloromethane is again added to the resulting aqueous layer and extracted once more. The organic layers are combined, washed with distilled water (60 mL), dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 5.

<Reaction Example 5> Preparation of Compound No. 6

Dimethylformamide and Compound No. 5 are added into a reaction container. After heating the mixture to about 30° C., potassium thioacetate is added thereto and stirred at 30° C. for 5 hours. After cooling the mixture to room temperature, dichloromethane and water are added thereto and extracted. After separation of layers, the resulting aqueous layer is re-extracted with dichloromethane. The organic layers extracted after the separation of layers are combined and washed with a 20% sodium chloride aqueous solution. After the separation of layers, sodium sulfate is added to the organic layer and stirred for 30 minutes. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 6.

<Reaction Example 6> Preparation of Compound No. 7

Water and Compound No. 6 are added into a container. The reaction solution is adjusted to pH 14 by adding a 0.1 M sodium hydroxide solution dropwise thereto. After stirring the mixture at room temperature for 12 hours, the mixture is adjusted to pH 6 to 7 using a 1 N HCl solution. After neutralization, dichloromethane is added thereto and the mixture is extracted. After separation of layers, the resulting aqueous layer is re-extracted with dichloromethane. The organic layers extracted after the separation of layers are combined and sodium sulfate is added thereto and stirred for 30 minutes. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 7.

<Reaction Example 7> Preparation of Compound No. 8

Compound No. 7 and methanol are added into a reaction container. Compound No. 11 is added dropwise thereto and stirred at room temperature for 3 days. The reaction solvent is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 8.

<Reaction Example 8> Preparation of Compound No. 9 [Linker #1]

Compound No. 8 and distilled water are added into a reaction container. The reaction solution is adjusted to pH 1 using a 1 N HCl solution and stirred at room temperature for 1 hour. Upon completion of the reaction, water and dichloromethane are added thereto and stirred for 5 minutes. The mixture is adjusted to pH 6 using 5% sodium bicarbonate. Dichloromethane is added thereto and extraction is performed. Sodium sulfate is added to the resulting organic layer and stirred for 30 minutes. The mixed solution is filtered and the filtrate is concentrated under reduced pressure. The concentrate is dissolved by adding dichloromethane (1 mL) thereto and methyl t-butyl ether is added dropwise thereto for 20 minutes. The thus-produced crystals are filtered, washed with methyl t-butyl ether, and dried under nitrogen at room temperature to obtain the target compound, Compound No. 9.

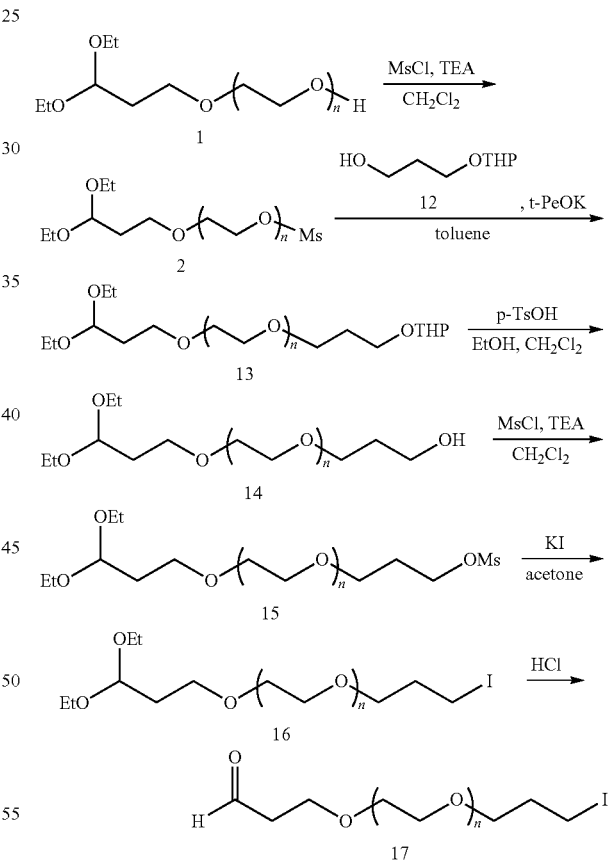

<Reaction Example 9> Preparation of Compound No. 13

Toluene and Compound No. 12 are added into a reaction container. After adding potassium t-pentoxide thereto, the mixture is heated to about 50° C. and stirred at 50° C. for 1 hour (an activation solution). Compound No. 2 and toluene are added into another container. The activation solution is cooled to room temperature and added dropwise to the mixed solution at 30° C. for 1 hour. After stirring the mixture at 30° C. for 3 hours, water is added to the reaction solution and extraction is performed. After separation of layers, dichloromethane is added to the aqueous layer and extracted. Dichloromethane is again added to the aqueous layer and the mixture is extracted once more. The resulting organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 13.

<Reaction Example 10> Preparation of Compound No. 14

Compound No. 13, ethanol, and dichloromethane are added into a reaction container. p-Toluene sulfonic acid (p-TsOH) is added thereto and stirred at room temperature for 20 hours. Sodium hydroxide is added thereto and the solvent is concentrated under reduced pressure. Dichloromethane and water are added thereto and stirred for 5 minutes. The organic layer is extracted therefrom and washed with water. The organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 14.

<Reaction Example 11> Preparation of Compound No. 15

Compound No. 14 and dichloromethane are added into a reaction container. While maintaining the reaction temperature at 10° C. or below, triethylamine and methanesulfonyl chloride are added thereto and stirred at room temperature for 3 hours. Upon completion of the reaction, water and dichloromethane are added thereto and stirred for 5 minutes. After extracting the organic layer, dichloromethane is again added to the resulting aqueous layer and the extraction is performed once more. The organic layers are combined, washed with distilled water, dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 15.

<Reaction Example 12> Preparation of Compound No. 16

Acetone and Compound No. 15 are added into a reaction container. After heating the mixture to 30° C., potassium iodide is added thereto, and heated to about 50° C. and stirred at 50° C. for 15 hours. The reaction solution is concentrated under reduced pressure and washed with dichloromethane and water. After separation of layers, the resulting organic layer is washed again with water. After the separation of layers, sodium sulfate is added to the organic layer and stirred for 30 minutes. The mixed solution is filtered and the filtrate is concentrated under reduced pressure. The concentrate is dissolved by adding dichloromethane thereto and methyl t-butyl ether (30 mL) is added dropwise thereto for 5 minutes. The thus-produced crystals are filtered, washed with methyl t-butyl ether, and dried under nitrogen at room temperature to obtain the target compound, Compound No. 16.

<Reaction Example 13> Preparation of Compound No. 17 [Linker #2]

Compound No. 16 and water are added into a container. The reaction solution is adjusted to pH 1.0 by adding a 1 N HCl solution dropwise thereto. After stirring at room temperature for 1 hour, the reaction solution is adjusted to pH 6 to 7 using a 5% sodium bicarbonate solution. After neutralization, dichloromethane is added thereto and the extraction is performed. After separation of layers, the aqueous layer is re-extracted with dichloromethane. The organic layers extracted after the separation of layers are combined and sodium sulfate is added thereto and stirred for 30 minutes. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 17.

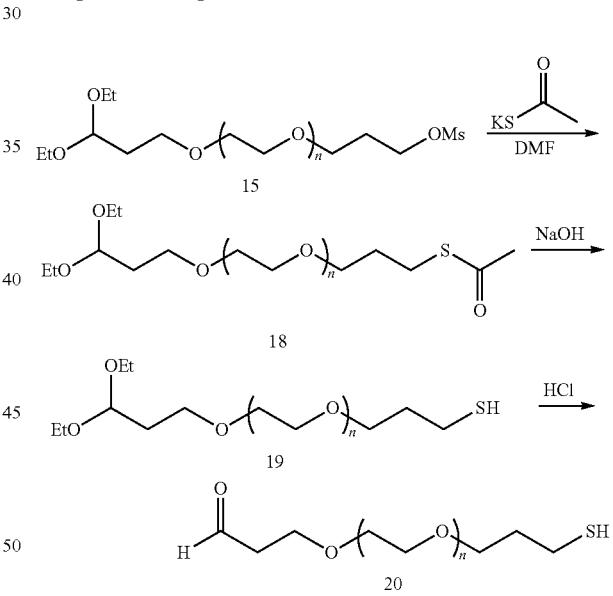

<Reaction Example 14> Preparation of Compound No. 18

Dimethylformamide and Compound No. 15 are added into a container. After heating the mixture to about 30° C., potassium thioacetate is added thereto and stirred at 30° C. for 5 hours. After cooling the mixture to room temperature, dichloromethane and water are added thereto and the extraction is performed. After separation of layers, the resulting aqueous layer is re-extracted with dichloromethane. The organic layers extracted after the separation of layers are combined and washed with a 20% sodium chloride aqueous solution. After the separation of layers, sodium sulfate is added to the organic layer and stirred for 30 minutes. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 18.

<Reaction Example 15> Preparation of Compound No. 19

Compound No. 18 and water are added into a reaction container. The reaction solution is adjusted to pH 14 by adding a 0.1 M NaOH solution dropwise thereto. After stirring at room temperature for 12 hours, the reaction solution is adjusted to pH 6 to 7 using a 1 N HCl solution. After neutralization, dichloromethane is added thereto and the extraction is performed. After separation of layers, the aqueous layer is re-extracted with dichloromethane. The organic layers extracted after the separation of layers are combined and sodium sulfate is added thereto and stirred for 30 minutes. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 19.

<Reaction Example 16> Preparation of Compound No. 20 [Linker #3]

Compound No. 19 and water are added into a reaction container. The reaction solution is adjusted to pH 1.0 by adding a 1 N HCl solution dropwise thereto. After stirring at room temperature for 1 hour, the reaction solution is adjusted to pH 6 to 7 using a 5% sodium bicarbonate solution. After neutralization, dichloromethane is added thereto and the extraction is performed. After separation of layers, the aqueous layer is re-extracted with dichloromethane (5 mL). The organic layers extracted after the separation of layers are combined and sodium sulfate is added thereto and stirred for 30 minutes. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 20.

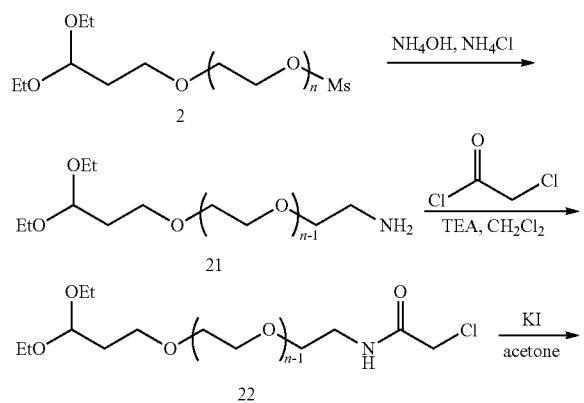

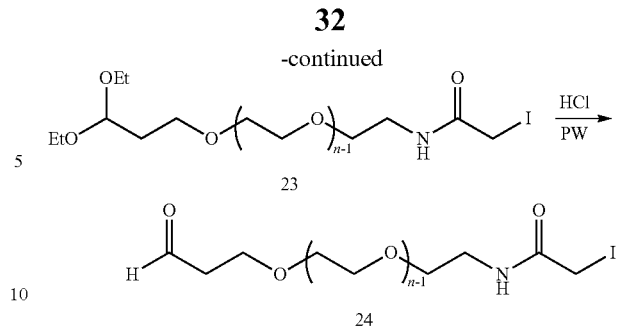

<Reaction Example 17> Preparation of Compound No. 21

An aqueous ammonia solution and ammonium chloride are added into a reaction container. Compound No. 5 is added thereto and stirred at room temperature for 4 days. Dichloromethane is added thereto and stirred for 5 minutes. After extracting an organic layer, dichloromethane is again added to the resulting aqueous layer and the extraction is performed once more. The organic layers are combined, washed with distilled water, dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 21.

<Reaction Example 18> Preparation of Compound No. 22

Compound No. 21 and dichloromethane are added into a reaction container. Triethylamine and chloroacetyl chloride are added dropwise thereto and stirred at room temperature for 16 hours. Upon completion of the reaction, the reaction solution is washed with water, dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 22.

<Reaction Example 19> Preparation of Compound No. 23

Compound No. 22 and acetone are added into a reaction container. KI is added thereto and stirred at 55° C. for 6 hours. After cooling the reaction solution to room temperature, the reaction solvent is concentrated under reduced pressure. Then, dichloromethane and water are added thereto and stirred for 5 minutes. After extracting the organic layer, dichloromethane is again added to the resulting aqueous layer and the extraction is performed once more. The organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 23.

<Reaction Example 20> Preparation of Compound No. 24 [Linker #5]

Compound No. 23 and distilled water are added into a reaction container. The reaction solution is adjusted to pH 1.0 using a 1 N HCl solution and stirred at room temperature for 1 hour. Upon completion of the reaction, water and dichloromethane are added thereto and stirred for 5 minutes. The resultant is adjusted to pH 6 using 5% sodium bicarbonate. The resultant is extracted by adding dichloromethane thereto, and sodium sulfate is added to the resulting organic layer and stirred for 30 minutes. The mixed solution is filtered and the filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 24.

<Reaction Example 21> Preparation of Compound No. 25

Compound No. 5 and acetone are added into a reaction container. KI is added thereto and stirred at 55° C. for 20 hours. After cooling the reaction solution to room temperature, the reaction solvent is concentrated under reduced pressure. Then, dichloromethane and water are added thereto and stirred for 5 minutes. After extracting the organic layer, dichloromethane is again added to the resulting aqueous layer and extracted once more. The organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 25.

<Reaction Example 22> Preparation of Compound No. 26 [Linker #11]

Compound No. 25 and distilled water are added into a reaction container. The reaction solution is adjusted to pH 1.0 using a 1 N HCl solution and stirred at room temperature for 1 hour. Upon completion of the reaction, water and dichloromethane are added thereto and stirred for 5 minutes. The resultant is adjusted to pH 6 using 5% sodium bicarbonate. The resultant is extracted by adding dichloromethane thereto, and sodium sulfate is added to the resulting organic layer and stirred for 30 minutes. The mixed solution is filtered and the filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 26.

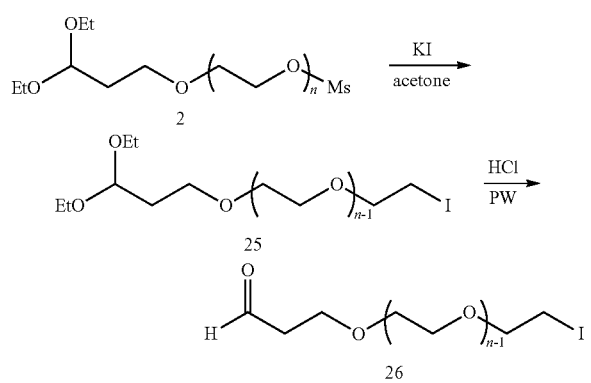

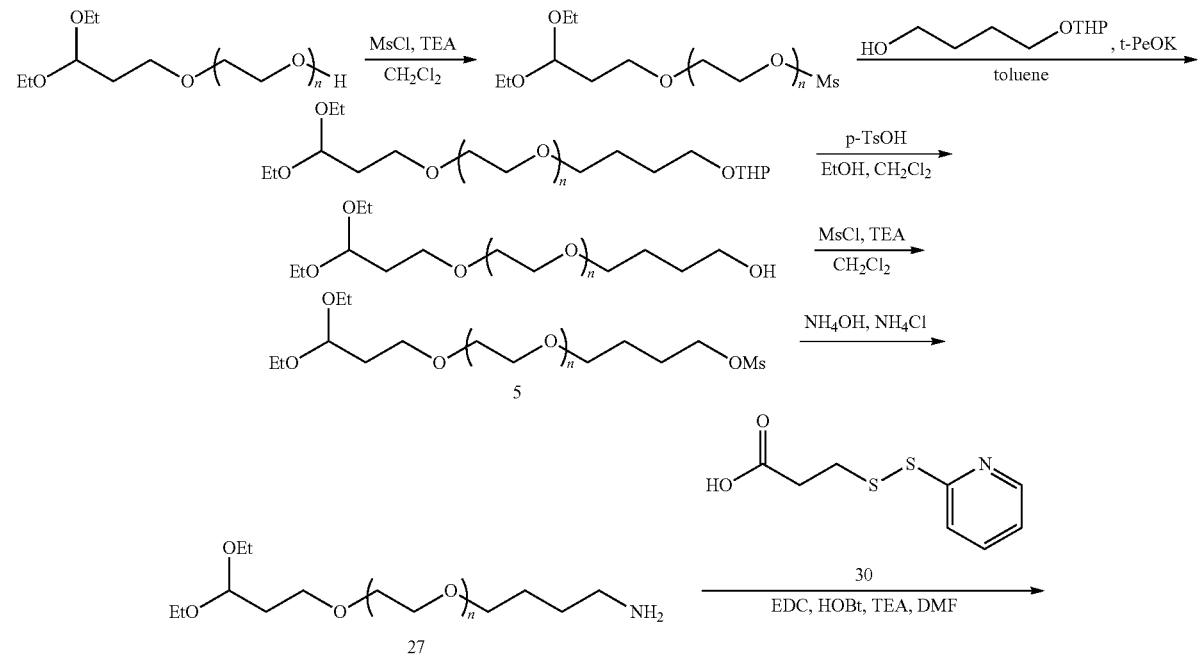

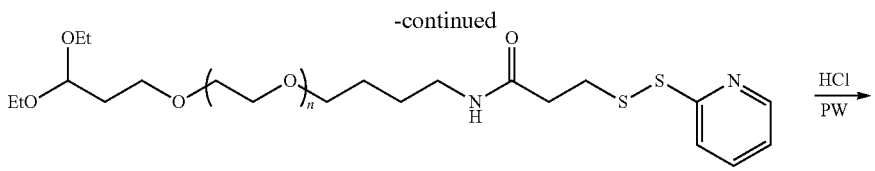

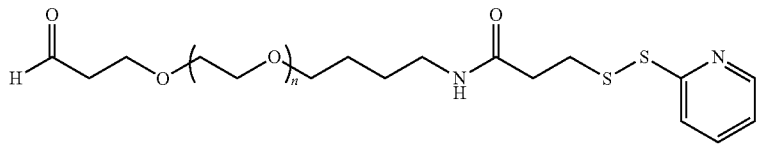

<Reaction Example 23> Preparation of Compound No. 27

An aqueous ammonia solution and ammonium chloride are added into a reaction container. Compound No. 5 is added thereto and stirred at room temperature for 4 days. Dichloromethane is added thereto and the organic layer is extracted therefrom and dichloromethane is again added and the extraction is performed once more. The organic layers are combined, washed with distilled water, dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 27.

<Reaction Example 24> Preparation of Compound No. 28

Compound No. 27, Compound No. 30, 1-ethyl-3-(3-dimethylaminopropyl)carbodiimide (EDC), hydroxybenzotriazole (HOBt), triethylamine, and dimethylformamide are added into a reaction container, and stirred at room temperature for 16 hours. Dichloromethane and water are added thereto and the extraction is performed. After separation of layers, the resulting aqueous layer is re-extracted with dichloromethane. The organic layers extracted after the separation of layers are combined and washed with a 20% sodium chloride aqueous solution. After the separation of layers, sodium sulfate is added to the organic layer and stirred. The mixed solution is filtered and the filtrate is concentrated under reduced pressure. The concentrate is dissolved by adding dichloromethane thereto and methyl t-butyl ether is added dropwise thereto for 5 minutes. The thus-produced crystals are filtered, washed with methyl t-butyl ether, and dried under nitrogen at room temperature to obtain the target compound, Compound No. 28.

<Reaction Example 25> Preparation of Compound No. 29 [Linker #7]

Compound No. 28 and distilled water are added into a reaction container. The reaction solution is adjusted to pH 1.0 using a 1 N HCl solution and stirred at room temperature for 1 hour. Upon completion of the reaction, water and dichloromethane are added thereto and stirred. The resultant is adjusted to pH 6 using 5% sodium bicarbonate. The resultant is extracted by adding dichloromethane thereto and sodium sulfate is added to the resulting organic layer. The mixed solution is filtered and the filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 29.

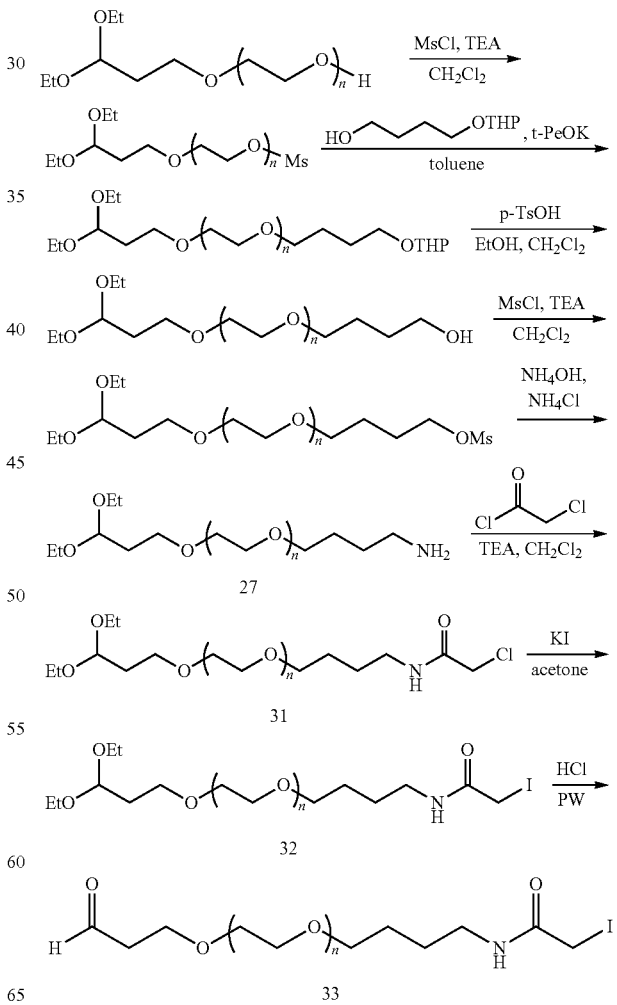

\<Reaction Example 26\> Preparation of Compound No. 31

Compound No. 27 and dichloromethane are added into a reaction container. Triethylamine and chloroacetyl chloride are added dropwise thereto and stirred at room temperature for 16 hours. Upon completion of the reaction, the reaction solution is washed with water, dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 31.

\<Reaction Example 27\> Preparation of Compound No. 32

Compound No. 31 and acetone are added into a reaction container. KI is added thereto and stirred at 55° C. for 6 hours. After cooling the reaction solution to room temperature, the reaction solvent is concentrated under reduced pressure. Then, dichloromethane and water are added thereto. After extracting the organic layer, dichloromethane is again added to the resulting aqueous layer and the extraction is performed once more. The organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 32.

\<Reaction Example 28\> Preparation of Compound No. 33 [Linker #8]

Compound No. 32 and distilled water are added into a reaction container. The reaction solution is adjusted to pH 1 using a 1 N HCl solution and stirred at room temperature for 1 hour. Upon completion of the reaction, water and dichloromethane are added thereto and stirred for 5 minutes. The resultant is adjusted to pH 6 using 5% sodium bicarbonate. The resultant is extracted by adding dichloromethane thereto, and sodium sulfate is added to the resulting organic layer. The mixed solution is filtered and the filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 33.

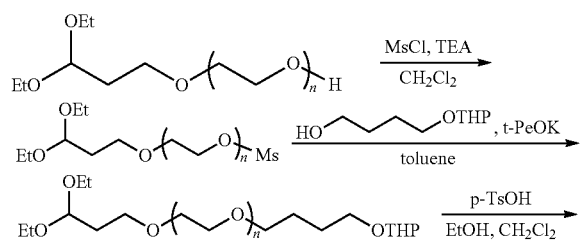

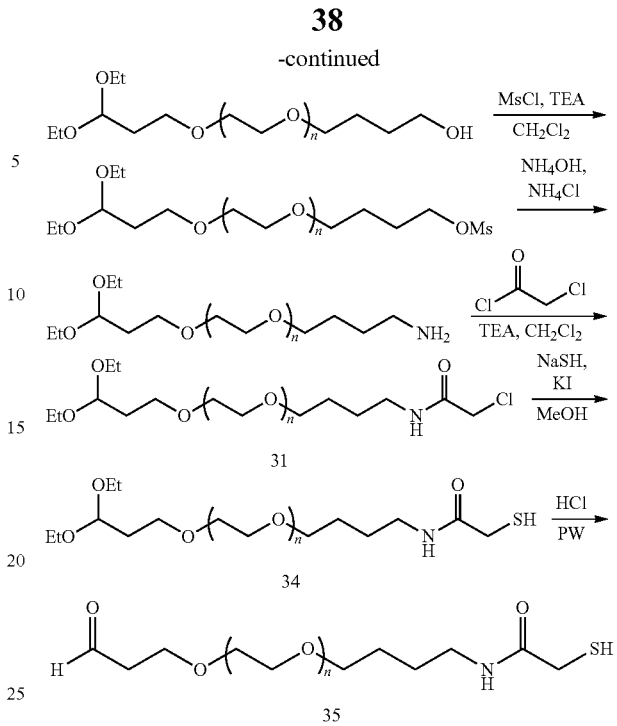

\<Reaction Example 29\> Preparation of Compound No. 34

Compound No. 31 and methanol are added into a reaction container. KI and NaSH are added thereto and stirred at room temperature for 6 hours. After cooling the reaction solution to room temperature, the reaction solvent is concentrated under reduced pressure. Then, dichloromethane and water are added thereto. After extracting an organic layer, dichloromethane is again added to the resulting aqueous layer and the extraction is performed once more. The organic layer is dried over magnesium sulfate, filtered, and the resulting filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 34.

\<Reaction Example 30\> Preparation of Compound No. 35 [Linker #9]

Compound No. 34 and distilled water are added into a reaction container. The reaction solution is adjusted to pH 1 using a 1 N HCl solution and stirred at room temperature for 1 hour. Upon completion of the reaction, water and dichloromethane are added thereto and stirred for 5 minutes. The resultant is adjusted to pH 6 using 5% sodium bicarbonate. The resultant is extracted by adding dichloromethane thereto, and sodium sulfate is added to the resulting organic layer. The mixed solution is filtered and the filtrate is concentrated under reduced pressure. The concentrate is dissolved by adding dichloromethane thereto and methyl t-butyl ether is added dropwise thereto for 20 minutes. The thus-produced crystals are filtered, washed with methyl t-butyl ether, and dried under nitrogen at room temperature to obtain the target compound, Compound No. 35.

Hereinafter, the present invention will be described in more detail with reference to the following embodiments, etc., to aid in the understanding of the present invention. However, these embodiments can be modified in various other forms and the scope of the present invention should not be interpreted to be limited by these embodiments. The embodiments are provided to more fully illustrate the present invention to those who have an average knowledge in the art.

Example 1: Preparation of polyethylene glycol derivatives

The present inventors have prepared polyethylene glycol derivatives in which desired reactive groups are introduced at both ends thereof. The methods for preparing the derivatives are described in Reaction Examples 1 to 25.

Representatively, heterofunctional PEG compounds, in which a propionaldehyde group is added to one end of the polyethylene glycol backbone while ortho-pyridyl disulfide (OPSS), iodoacetamide (IA), an iodine group, or sulfhydryl group (SH—) is added to the other end, were prepared [FIG. 1].

The purity of each of the thus-prepared PEG compounds was analyzed by NMR and reversed phase chromatography (RPC), respectively.

The details of the representative polyethylene glycol derivatives are as follows.

(1) Linker #1: pALD-PEG-ortho-pyridyl disulfide

[Formula 3]

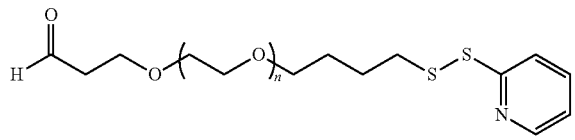

Here, n is an integer of 200 to 300.

The molecular weight of the thus-prepared polyethylene glycol linker was about 10 kDa, and its structure was confirmed by NMR analysis. The purity was confirmed to be about 80% by RPC analysis.

$^1$H-NMR (CDCl$_3$, 400 MHz): δ 9.79 (t, 1H, J=2.0 Hz), 8.50 (d, 1H, J=5.6 Hz), 7.71-7.64 (m, 2H), 7.09-6.70 (m, 1H), 3.87-3.40 (m, 908H), 2.82 (t, 2H, J=5.6 Hz), 2.68 (t, 2H, J=2.0 Hz), 1.86-1.66 (m, 4H)

(2) Linker #2: pALD-PEG-iodide

[Formula 4]

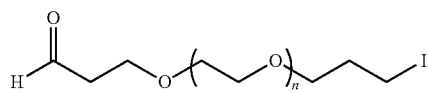

Here, n is an integer of 200 to 300.

The molecular weight of the thus-prepared polyethylene glycol linker was about 10 kDa, and its structure was confirmed by NMR analysis. The purity was confirmed to be about 87% by RPC analysis.

$^1$H-NMR (CDCl$_3$, 400 MHz): δ 9.81 (s, 1H), 3.84-3.47 (m, 910H), 3.29 (t, 2H, J=6.8 Hz), 2.71-2.69 (m, 2H), 2.10-2.06 (m, 2H)

(3) Linker #3: pALD-PEG-sulfhydryl group

[Formula 5]

Here, n is an integer of 200 to 300.

The molecular weight of the thus-prepared polyethylene glycol linker was about 10 kDa, and its structure was confirmed by NMR analysis. The purity was confirmed to be about 76% by RPC analysis.

$^1$H-NMR (CDCl$_3$, 400 MHz): δ 9.79 (s, 1H), 3.82-3.45 (m, 910H), 2.74 (t, 2H, J=6.8 Hz), 2.69-2.67 (m, 2H), 1.99-1.95 (m, 2H)

(4) Linker #5: pALD-PEG-iodide

[Formula 7]

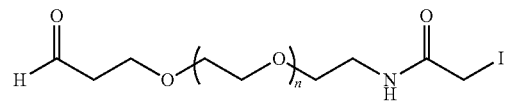

Here, n is an integer of 200 to 300.

The molecular weight of the thus-prepared polyethylene glycol linker was about 10 kDa, and its structure was confirmed by NMR analysis. The purity was confirmed to be about 88% by RPC analysis.

$^1$H-NMR (CDCl$_3$, 400 MHz): δ 9.78 (t, 1H, J=1.6 Hz), 3.82-3.41 (m, 912H), 2.67 (t, 2H, J=2.0 Hz)

(5) Linker #7: pALD-PEG-ortho-pyridyl disulfide

[Formula 9]

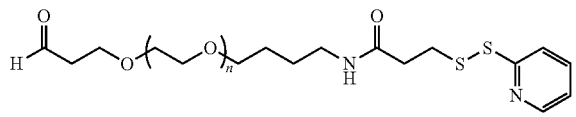

Here, n is an integer of 200 to 300.

The molecular weight of the thus-prepared polyethylene glycol linker was about 10 kDa, and the purity was confirmed to be about 81% by RPC analysis.

(6) Linker #8: pALD-PEG-iodide

[Formula 10]

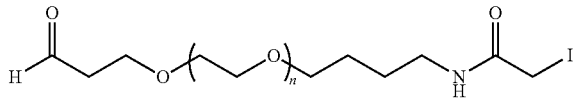

Here, n is an integer of 200 to 300.

The molecular weight of the thus-prepared polyethylene glycol linker was about 10 kDa, and its structure was confirmed by NMR analysis. The purity was confirmed to be about 78% by RPC analysis.

$^1$H-NMR (CDCl$_3$, 400 MHz): δ 9.78 (s, 1H), 3.82-3.41 (m, 912H), 2.70 (t, 2H, J=2.0 Hz), 1.44-1.24 (m, 4H)

(7) Linker #9: pALD-PEG-sulfhydryl group

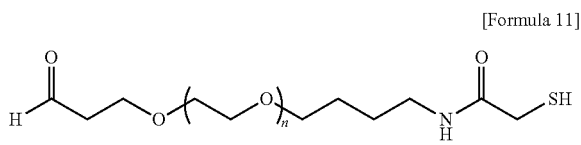

[Formula 11]

Here, n is an integer of 200 to 300.

The molecular weight of the thus-prepared polyethylene glycol linker was about 10 kDa, and the purity was confirmed to be about 76% by RPC analysis.

(8) Linker #11: pALD-PEG-iodide (Comparative Example)

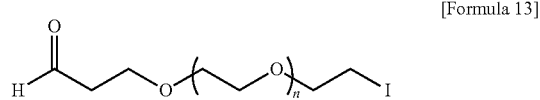

[Formula 13]

Here, n is an integer of 200 to 300.

The molecular weight of the thus-prepared polyethylene glycol linker was about 10 kDa, and its structure was confirmed by NMR analysis. The purity was confirmed to be about 89% RPC analysis.

$^1$H-NMR (CDCl$_3$, 400 MHz): δ 9.79 (t, 1H, J=2.0 Hz), 3.82-3.41 (m, 908H), 3.29-3.22 (m, 2H), 2.69 (t, 2H, J=2.0 Hz)

Example 2: Comparison of Reactivity Between Novel Polyethylene Glycol Derivatives In order to prepare a physiologically active polypeptide conjugate using the polyethylene glycol derivatives prepared in Example 1, a conjugate was prepared using a triple agonist peptide, GLP-1/Glucagon/GIP, as a representative physiologically active peptide. The triple agonist peptide consists of 30 amino acids and it corresponds to a peptide including a cysteine residue. Accordingly, the triple agonist peptide was used for the comparison of reactivity of the thiol reactive group of the polyethylene glycol derivatives according to the present invention.

Additionally, linkers #2, #3, #5, #8, #9, and #11 having a molecular weight of about 10K (10,000 Da) were used as polyethylene glycol derivatives. In particular, although linkers #3 and #9 correspond to 10K pALD-PEG-SH (PEG which has a propionaldehyde group and a sulfhydryl group at each end), linker #9 is characterized in that it has an amide structure in front of a thiol reactive group, unlike linker #3. Additionally, linkers #2, #5, #8, and #11 correspond to 10K pALD-PEG-I (PEG which has a propionaldehyde group and an iodine group at each end), linkers #5 and #8 are characterized in that they have an amide structure in front of a thiol reactive group, unlike linkers #2 and #11.

After dissolving peptide powder in 10 mM HCl, for the PEGylation of 10K pALD-PEG-I and 10K pALD-PEG-SH to the cysteine residue of the peptide, the peptide and PEG were reacted at a molar ratio of 1:3 to 1:5 with a reaction concentration of 3 mg/mL at room temperature for about 2 hours. In particular, the reaction was performed in the presence of 50 mM sodium citrate (pH 5.0) or 50 mM HEPES (pH 7.5) and 60% isopropanol (IPA). Upon completion of SDS-PAGE analysis, the reactivity of each thiol reactive group was compared by a band integration method (FIG. 18). Upon confirmation of the reactivity, it was confirmed that the PEG which is characterized by having an amide structure in front of the thiol group has superior reactivity to the PEG which does not have an amide structure in front of the thiol group.

Example 3: Preparation of a Conjugate Between a Physiologically Active Polypeptide and an Immunoglobulin Fc Using a Novel Polyethylene Glycol Derivative In order to prepare a conjugate between a physiologically active polypeptide and an immunoglobulin Fc using the polyethylene glycol derivatives prepared in Example 1, a conjugate was prepared using the peptide mentioned in Example 2.

First, linker #7 having a molecular weight of about 10K (10,000 Da) was used as the polyethylene glycol derivative. In particular, linker #7 corresponds to pALD-PEG-OPSS with a molecular weight of about 10K (PEG which has a propionaldehyde group and ortho-pyridyl disulfide group at each end). After dissolving peptide powder in 10 mM HCl, for the PEGylation of 10K pALD-PEG-OPSS to the cysteine residue of the peptide, the peptide and PEG were reacted at a molar ratio of 1:1 to 1:3 with a reaction concentration of 1 mg/mL or 3 mg/mL at room temperature for about 2 hours. In particular, the reaction was performed in the presence of 50 mM sodium citrate (pH 3.0 to pH 5.0) or 50 mM Tris (pH 8.0) and 60% isopropanol.

Additionally, linkers #8, and #9 having a molecular weight of about 10K (10,000 Da) were used as polyethylene glycol derivatives. In particular, linker #8 corresponds to 10K pALD-PEG-IA with a molecular weight of about 10K (PEG which has a propionaldehyde group and iodoacetamide (IA) at each end) and linker #9 corresponds to 10K pALD-PEG-SH with a molecular weight of about 10K (PEG which has a propionaldehyde group and a sulfhydryl group at each end).

For the preparation of a conjugate using the pALD-PEG-IA and pALD-PEG-SH as linkers, the PEGylation reaction was performed in the same condition as in Example 2 and the reaction solution was purified using the SP—HP (GE Healthcare, USA) column which utilized a buffer containing sodium citrate (pH 3.0) and a 45% EtOH and KCl concentration gradient.

Then, after being conjugated to each reactive group, the purified mono-PEGylated peptide and immunoglobulin Fc were reacted at a molar ratio of 1:5 with the total protein concentration of 20 mg/mL at 4° C. for 15 hours. In particular, 20% isopropanol and 20 mM sodium cyanoborohydride, as a reducing agent, were added to 100 mM potassium phosphate buffer as the reaction solution.

Upon completion of the reaction, the reaction solution was applied to a Source 15Q (GE Healthcare, USA) column using a NaCl concentration gradient in a Bis-Tris (pH 6.5) buffer and then applied to a Source ISO (GE Healthcare, USA) column using a concentration gradient of (NH$_4$)$_2$SO$_4$ and Tris (pH 7.5) buffer, and thereby the triple agonist-10K PEG-IgFc conjugate was purified. The purity of the thus-prepared conjugate sample was confirmed by SDS-PAGE analysis, and the molecular weight of the conjugate of the triple agonist and PEG was confirmed. Then, the molecular weight of the triple agonist-10K PEG-IgFc conjugate, in which an IgFc was linked to the PEG conjugated to the triple agonist, was confirmed in a non-reducing condition. The experimental results thereof are shown in FIGS. 19 to 21.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

```
                         SEQUENCE LISTING

Sequence total quantity: 106
SEQ ID NO: 1             moltype = AA  length = 30
FEATURE                  Location/Qualifiers
REGION                   1..30
                         note = Trigonal agonist
MOD_RES                  2
                         note = Xaa is aminoisobutyric acid (Aib)
source                   1..30
                         mol_type = protein
                         organism = synthetic construct
SEQUENCE: 1
HXQGTFTSDV SSYLDGQAAK EFIAWLVKGC                                      30

SEQ ID NO: 2             moltype = AA  length = 30
FEATURE                  Location/Qualifiers
REGION                   1..30
                         note = Trigonal agonist
MOD_RES                  2
                         note = Xaa is aminoisobutyric acid (Aib)
source                   1..30
                         mol_type = protein
                         organism = synthetic construct
SEQUENCE: 2
HXQGTFTSDV SSYLDGQAQK EFIAWLVKGC                                      30

SEQ ID NO: 3             moltype = AA  length = 41
FEATURE                  Location/Qualifiers
REGION                   1..41
                         note = Trigonal agonist
MOD_RES                  2
                         note = Xaa is aminoisobutyric acid (Aib)
source                   1..41
                         mol_type = protein
                         organism = synthetic construct
SEQUENCE: 3
HXQGTFTSDV SSYLLGQAAK QFIAWLVKGG GPSSGAPPPS C                         41

SEQ ID NO: 4             moltype = AA  length = 30
FEATURE                  Location/Qualifiers
REGION                   1..30
                         note = Trigonal agonist
MOD_RES                  2
                         note = Xaa is aminoisobutyric acid (Aib)
source                   1..30
                         mol_type = protein
                         organism = synthetic construct
SEQUENCE: 4
HXQGTFTSDV SSYLLGQQQK EFIAWLVKGC                                      30

SEQ ID NO: 5             moltype = AA  length = 41
FEATURE                  Location/Qualifiers
REGION                   1..41
                         note = Trigonal agonist
MOD_RES                  2
                         note = Xaa is aminoisobutyric acid (Aib)
source                   1..41
                         mol_type = protein
                         organism = synthetic construct
SEQUENCE: 5
HXQGTFTSDV SSYLLGQQQK EFIAWLVKGG GPSSGAPPPS C                         41

SEQ ID NO: 6             moltype = AA  length = 30
FEATURE                  Location/Qualifiers
REGION                   1..30
                         note = Trigonal agonist
MOD_RES                  2
                         note = Xaa is aminoisobutyric acid (Aib)
```

```
source                   1..30
                         mol_type = protein
                         organism = synthetic construct
SEQUENCE: 6
HXQGTFTSDV SSYLDGQAAK EFVAWLLKGC                                                30

SEQ ID NO: 7             moltype = AA  length = 30
FEATURE                  Location/Qualifiers
REGION                   1..30
                         note = Trigonal agonist
MOD_RES                  2
                         note = Xaa is aminoisobutyric acid (Aib)
source                   1..30
                         mol_type = protein
                         organism = synthetic construct
SEQUENCE: 7
HXQGTFTSDV SKYLDGQAAK EFVAWLLKGC                                                30

SEQ ID NO: 8             moltype = AA  length = 30
FEATURE                  Location/Qualifiers
REGION                   1..30
                         note = Trigonal agonist
MOD_RES                  2
                         note = Xaa is aminoisobutyric acid (Aib)
source                   1..30
                         mol_type = protein
                         organism = synthetic construct
SEQUENCE: 8
HXQGTFTSDV SKYLDGQAAQ EFVAWLLKGC                                                30

SEQ ID NO: 9             moltype = AA  length = 30
FEATURE                  Location/Qualifiers
REGION                   1..30
                         note = Trigonal agonist
MOD_RES                  2
                         note = Xaa is aminoisobutyric acid (Aib)
source                   1..30
                         mol_type = protein
                         organism = synthetic construct
SEQUENCE: 9
HXQGTFTSDV SKYLDGQAAQ EFVAWLLAGC                                                30

SEQ ID NO: 10            moltype = AA  length = 41
FEATURE                  Location/Qualifiers
REGION                   1..41
                         note = Trigonal agonist
MOD_RES                  2
                         note = Xaa is aminoisobutyric acid (Aib)
source                   1..41
                         mol_type = protein
                         organism = synthetic construct
SEQUENCE: 10
HXQGTFTSDV SKYLDGQAAQ EFVAWLLAGG GPSSGAPPPS C                                   41

SEQ ID NO: 11            moltype = AA  length = 41
FEATURE                  Location/Qualifiers
REGION                   1..41
                         note = Trigonal agonist
SITE                     1
                         note = Xaa is 4-imidazoacetyl (CA)
source                   1..41
                         mol_type = protein
                         organism = synthetic construct
SEQUENCE: 11
XGEGTFTSDL SKYLDSRRQQ LFVQWLKAGG PSSGAPPPSH G                                   41

SEQ ID NO: 12            moltype = AA  length = 41
FEATURE                  Location/Qualifiers
REGION                   1..41
                         note = Trigonal agonist
SITE                     1
                         note = Xaa is 4-imidazoacetyl (CA)
source                   1..41
                         mol_type = protein
                         organism = synthetic construct
SEQUENCE: 12
XGEGTFISDL SKYMDEQAVQ LFVEWLMAGG PSSGAPPPSH G                                   41
```

```
SEQ ID NO: 13           moltype = AA  length = 41
FEATURE                 Location/Qualifiers
REGION                  1..41
                        note = Trigonal agonist
SITE                    1
                        note = Xaa is 4-imidazoacetyl (CA)
source                  1..41
                        mol_type = protein
                        organism = synthetic construct
SEQUENCE: 13
XGEGTFISDY SIQLDEIAVQ DFVEWLLAQK PSSGAPPPSH G                           41

SEQ ID NO: 14           moltype = AA  length = 41
FEATURE                 Location/Qualifiers
REGION                  1..41
                        note = Trigonal agonist
SITE                    1
                        note = Xaa is 4-imidazoacetyl (CA)
source                  1..41
                        mol_type = protein
                        organism = synthetic construct
SEQUENCE: 14
XGQGTFTSDY SIQLDEIAVR DFVEWLKNGG PSSGAPPPSH G                           41

SEQ ID NO: 15           moltype = AA  length = 41
FEATURE                 Location/Qualifiers
REGION                  1..41
                        note = Trigonal agonist
SITE                    1
                        note = Xaa is 4-imidazoacetyl (CA)
source                  1..41
                        mol_type = protein
                        organism = synthetic construct
SEQUENCE: 15
XGQGTFTSDL SKQMDEEAVR LFIEWLKNGG PSSGAPPPSH G                           41

SEQ ID NO: 16           moltype = AA  length = 41
FEATURE                 Location/Qualifiers
REGION                  1..41
                        note = Trigonal agonist
SITE                    1
                        note = Xaa is 4-imidazoacetyl (CA)
source                  1..41
                        mol_type = protein
                        organism = synthetic construct
SEQUENCE: 16
XGQGTFTSDL SKQMDSEAQQ LFIEWLKNGG PSSGAPPPSH G                           41

SEQ ID NO: 17           moltype = AA  length = 41
FEATURE                 Location/Qualifiers
REGION                  1..41
                        note = Trigonal agonist
SITE                    1
                        note = Xaa is 4-imidazoacetyl (CA)
source                  1..41
                        mol_type = protein
                        organism = synthetic construct
SEQUENCE: 17
XGQGTFTSDL SKQMDEERAR EFIEWLLAQK PSSGAPPPSH G                           41

SEQ ID NO: 18           moltype = AA  length = 41
FEATURE                 Location/Qualifiers
REGION                  1..41
                        note = Trigonal agonist
SITE                    1
                        note = Xaa is 4-imidazoacetyl (CA)
source                  1..41
                        mol_type = protein
                        organism = synthetic construct
SEQUENCE: 18
XGQGTFTSDL SKQMDSERAR EFIEWLKNTG PSSGAPPPSH G                           41

SEQ ID NO: 19           moltype = AA  length = 41
FEATURE                 Location/Qualifiers
REGION                  1..41
                        note = Trigonal agonist
SITE                    1
                        note = Xaa is 4-imidazoacetyl (CA)
```

```
                        source           1..41
                                         mol_type = protein
                                         organism = synthetic construct
SEQUENCE: 19
XGQGTFTSDL SIQYDSEHQR DFIEWLKDTG PSSGAPPPSH G                        41

SEQ ID NO: 20           moltype = AA  length = 41
FEATURE                 Location/Qualifiers
REGION                  1..41
                        note = Trigonal agonist
SITE                    1
                        note = Xaa is 4-imidazoacetyl (CA)
source                  1..41
                        mol_type = protein
                        organism = synthetic construct
SEQUENCE: 20
XGQGTFTSDL SIQYEEEAQQ DFVEWLKDTG PSSGAPPPSH G                        41

SEQ ID NO: 21           moltype = AA  length = 39
FEATURE                 Location/Qualifiers
REGION                  1..39
                        note = Trigonal agonist
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 21
YXQGTFTSDY SKYLDECRAK EFVQWLLDHH PSSGQPPPS                           39

SEQ ID NO: 22           moltype = AA  length = 39
FEATURE                 Location/Qualifiers
REGION                  1..39
                        note = Trigonal agonist
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 22
YXQGTFTSDY SKCLDEKRAK EFVQWLLDHH PSSGQPPPS                           39

SEQ ID NO: 23           moltype = AA  length = 41
FEATURE                 Location/Qualifiers
REGION                  1..41
                        note = Trigonal agonist
MOD_RES                 2
                        note = Xaa is aminoisobutyric acid (Aib)
SITE                    16..20
                        note = amino acids at positions 16 and 20 form a ring
source                  1..41
                        mol_type = protein
                        organism = synthetic construct
SEQUENCE: 23
YXQGTFTSDY SKYLDECRAK EFVQWLLAQK GKKNDWKHNI T                        41

SEQ ID NO: 24           moltype = AA  length = 39
FEATURE                 Location/Qualifiers
REGION                  1..39
                        note = Trigonal agonist
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 24
YXQGTFTSDY SKYLDECRAK EFVQWLKNGG PSSGAPPPS                           39

SEQ ID NO: 25           moltype = AA  length = 39
FEATURE                 Location/Qualifiers
REGION                  1..39
                        note = Trigonal agonist
```

```
MOD_RES              2
                     note = Xaa is aminoisobutyric acid (Aib)
source               1..39
                     mol_type = protein
                     organism = synthetic construct
SEQUENCE: 25
HXQGTFTSDC SKYLDERAAQ DFVQWLLDGG PSSGAPPPS                          39

SEQ ID NO: 26        moltype = AA  length = 39
FEATURE              Location/Qualifiers
REGION               1..39
                     note = Trigonal agonist
MOD_RES              2
                     note = Xaa is aminoisobutyric acid (Aib)
source               1..39
                     mol_type = protein
                     organism = synthetic construct
SEQUENCE: 26
HXQGTFTSDC SKYLDSRAAQ DFVQWLLDGG PSSGAPPPS                          39

SEQ ID NO: 27        moltype = AA  length = 40
FEATURE              Location/Qualifiers
REGION               1..40
                     note = Trigonal agonist
MOD_RES              2
                     note = Xaa is aminoisobutyric acid (Aib)
source               1..40
                     mol_type = protein
                     organism = synthetic construct
SEQUENCE: 27
HXQGTFTSDY SKYLDERACQ DFVQWLLDQG GPSSGAPPPS                         40

SEQ ID NO: 28        moltype = AA  length = 41
FEATURE              Location/Qualifiers
REGION               1..41
                     note = Trigonal agonist
MOD_RES              2
                     note = Xaa is aminoisobutyric acid (Aib)
source               1..41
                     mol_type = protein
                     organism = synthetic construct
SEQUENCE: 28
HXQGTFTSDY SKYLDEKRAQ EFVCWLLAQK GKKNDWKHNI T                       41

SEQ ID NO: 29        moltype = AA  length = 30
FEATURE              Location/Qualifiers
REGION               1..30
                     note = Trigonal agonist
MOD_RES              2
                     note = Xaa is aminoisobutyric acid (Aib)
SITE                 16..20
                     note = amino acids at positions 16 and 20 form a ring
source               1..30
                     mol_type = protein
                     organism = synthetic construct
SEQUENCE: 29
HXQGTFTSDY SKYLDEKAAK EFVQWLLNTC                                    30

SEQ ID NO: 30        moltype = AA  length = 30
FEATURE              Location/Qualifiers
REGION               1..30
                     note = Trigonal agonist
MOD_RES              2
                     note = Xaa is aminoisobutyric acid (Aib)
SITE                 16..20
                     note = amino acids at positions 16 and 20 form a ring
source               1..30
                     mol_type = protein
                     organism = synthetic construct
SEQUENCE: 30
HXQGTFTSDY SKYLDEKAQK EFVQWLLDTC                                    30

SEQ ID NO: 31        moltype = AA  length = 29
FEATURE              Location/Qualifiers
REGION               1..29
                     note = Trigonal agonist
MOD_RES              2
                     note = Xaa is aminoisobutyric acid (Aib)
```

```
SITE                    16..20
                        note = amino acids at positions 16 and 20 form a ring
source                  1..29
                        mol_type = protein
                        organism = synthetic construct
SEQUENCE: 31
HXQGTFTSDY SKYLDEKACK EFVQWLLAQ                                          29

SEQ ID NO: 32           moltype = AA  length = 39
FEATURE                 Location/Qualifiers
REGION                  1..39
                        note = Trigonal agonist
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 32
HXQGTFTSDY SKYLDEKACK DFVQWLLDGG PSSGAPPPS                               39

SEQ ID NO: 33           moltype = AA  length = 31
FEATURE                 Location/Qualifiers
REGION                  1..31
                        note = Trigonal agonist
MOD_RES                 2
                        note = Xaa is aminoisobutyric acid (Aib)
SITE                    16..20
                        note = amino acids at positions 16 and 20 form a ring
source                  1..31
                        mol_type = protein
                        organism = synthetic construct
SEQUENCE: 33
HXQGTFTSDY SIAMDEIHQK DFVNWLLAQK C                                       31

SEQ ID NO: 34           moltype = AA  length = 31
FEATURE                 Location/Qualifiers
REGION                  1..31
                        note = Trigonal agonist
MOD_RES                 2
                        note = Xaa is aminoisobutyric acid (Aib)
SITE                    16..20
                        note = amino acids at positions 16 and 20 form a ring
source                  1..31
                        mol_type = protein
                        organism = synthetic construct
SEQUENCE: 34
HXQGTFTSDY SKYLDEKRQK EFVNWLLAQK C                                       31

SEQ ID NO: 35           moltype = AA  length = 31
FEATURE                 Location/Qualifiers
REGION                  1..31
                        note = Trigonal agonist
MOD_RES                 2
                        note = Xaa is aminoisobutyric acid (Aib)
SITE                    16..20
                        note = amino acids at positions 16 and 20 form a ring
source                  1..31
                        mol_type = protein
                        organism = synthetic construct
SEQUENCE: 35
HXQGTFTSDY SIAMDEIHQK DFVNWLLNTK C                                       31

SEQ ID NO: 36           moltype = AA  length = 40
FEATURE                 Location/Qualifiers
REGION                  1..40
                        note = Trigonal agonist
MOD_RES                 2
                        note = Xaa is aminoisobutyric acid (Aib)
SITE                    16..20
                        note = amino acids at positions 16 and 20 form a ring
source                  1..40
                        mol_type = protein
                        organism = synthetic construct
SEQUENCE: 36
HXQGTFTSDY SKYLCEKRQK EFVQWLLNGG PSSGAPPPSG                              40
```

```
SEQ ID NO: 37          moltype = AA  length = 40
FEATURE                Location/Qualifiers
REGION                 1..40
                       note = Trigonal agonist
MOD_RES                2
                       note = Xaa is aminoisobutyric acid (Aib)
SITE                   16..20
                       note = amino acids at positions 16 and 20 form a ring
source                 1..40
                       mol_type = protein
                       organism = synthetic construct
SEQUENCE: 37
HXQGTFTSDY SKYLDECRQK EFVQWLLNGG PSSGAPPPSG                              40

SEQ ID NO: 38          moltype = AA  length = 40
FEATURE                Location/Qualifiers
REGION                 1..40
                       note = Trigonal agonist
SITE                   1
                       note = Xaa is 4-imidazoacetyl (CA)
MOD_RES                2
                       note = Xaa is aminoisobutyric acid (Aib)
source                 1..40
                       mol_type = protein
                       organism = synthetic construct
SEQUENCE: 38
XXQGTFTSDK SSYLDERAAQ DFVQWLLDGG PSSGAPPPSS                              40

SEQ ID NO: 39          moltype = AA  length = 40
FEATURE                Location/Qualifiers
REGION                 1..40
                       note = Trigonal agonist
MOD_RES                2
                       note = Xaa is aminoisobutyric acid (Aib)
source                 1..40
                       mol_type = protein
                       organism = synthetic construct
SEQUENCE: 39
HXQGTFTSDY SKYLDGQHAQ CFVAWLLAGG GPSSGAPPPS                              40

SEQ ID NO: 40          moltype = AA  length = 39
FEATURE                Location/Qualifiers
REGION                 1..39
                       note = Trigonal agonist
MOD_RES                2
                       note = Xaa is aminoisobutyric acid (Aib)
source                 1..39
                       mol_type = protein
                       organism = synthetic construct
SEQUENCE: 40
HXQGTFTSDK SKYLDERACQ DFVQWLLDGG PSSGAPPPS                               39

SEQ ID NO: 41          moltype = AA  length = 39
FEATURE                Location/Qualifiers
REGION                 1..39
                       note = Trigonal agonist
MOD_RES                2
                       note = Xaa is aminoisobutyric acid (Aib)
source                 1..39
                       mol_type = protein
                       organism = synthetic construct
SEQUENCE: 41
HXQGTFTSDK SKYLDECAAQ DFVQWLLDGG PSSGAPPPS                               39

SEQ ID NO: 42          moltype = AA  length = 40
FEATURE                Location/Qualifiers
REGION                 1..40
                       note = Trigonal agonist
MOD_RES                2
                       note = Xaa is aminoisobutyric acid (Aib)
SITE                   16..20
                       note = amino acids at positions 16 and 20 form a ring
source                 1..40
                       mol_type = protein
                       organism = synthetic construct
SEQUENCE: 42
YXQGTFTSDY SKYLDEKRAK EFVQWLLDHH PSSGQPPPSC                              40
```

```
SEQ ID NO: 43               moltype = AA   length = 39
FEATURE                     Location/Qualifiers
REGION                      1..39
                            note = Trigonal agonist
MOD_RES                     2
                            note = Xaa is aminoisobutyric acid (Aib)
SITE                        16..20
                            note = amino acids at positions 16 and 20 form a ring
source                      1..39
                            mol_type = protein
                            organism = synthetic construct
SEQUENCE: 43
YXQGTFTSDY SKYLDEKRAK EFVQWLLDHH CSSGQPPPS                                   39

SEQ ID NO: 44               moltype = AA   length = 39
FEATURE                     Location/Qualifiers
REGION                      1..39
                            note = Trigonal agonist
source                      1..39
                            mol_type = protein
                            organism = synthetic construct
SEQUENCE: 44
HGQGTFTSDC SKQLDGQAAQ EFVAWLLAGG PSSGAPPPS                                   39

SEQ ID NO: 45               moltype = AA   length = 39
FEATURE                     Location/Qualifiers
REGION                      1..39
                            note = Trigonal agonist
source                      1..39
                            mol_type = protein
                            organism = synthetic construct
SEQUENCE: 45
HGQGTFTSDC SKYMDGQAAQ DFVAWLLAGG PSSGAPPPS                                   39

SEQ ID NO: 46               moltype = AA   length = 39
FEATURE                     Location/Qualifiers
REGION                      1..39
                            note = Trigonal agonist
source                      1..39
                            mol_type = protein
                            organism = synthetic construct
SEQUENCE: 46
HGQGTFTSDC SKYLDEQHAQ EFVAWLLAGG PSSGAPPPS                                   39

SEQ ID NO: 47               moltype = AA   length = 39
FEATURE                     Location/Qualifiers
REGION                      1..39
                            note = Trigonal agonist
source                      1..39
                            mol_type = protein
                            organism = synthetic construct
SEQUENCE: 47
HGQGTFTSDC SKYLDGQRAQ EFVAWLLAGG PSSGAPPPS                                   39

SEQ ID NO: 48               moltype = AA   length = 39
FEATURE                     Location/Qualifiers
REGION                      1..39
                            note = Trigonal agonist
source                      1..39
                            mol_type = protein
                            organism = synthetic construct
SEQUENCE: 48
HGQGTFTSDC SKYLDGQRAQ DFVNWLLAGG PSSGAPPPS                                   39

SEQ ID NO: 49               moltype = AA   length = 30
FEATURE                     Location/Qualifiers
REGION                      1..30
                            note = Trigonal agonist
SITE                        1
                            note = Xaa is 4-imidazoacetyl (CA)
MOD_RES                     2
                            note = Xaa is aminoisobutyric acid (Aib)
SITE                        16..20
                            note = amino acids at positions 16 and 20 form a ring
source                      1..30
                            mol_type = protein
                            organism = synthetic construct
SEQUENCE: 49
XXQGTFTSDY SICMDEIHQK DFVNWLLNTK                                             30
```

```
SEQ ID NO: 50            moltype = AA  length = 40
FEATURE                  Location/Qualifiers
REGION                   1..40
                         note = Trigonal agonist
MOD_RES                  2
                         note = Xaa is aminoisobutyric acid (Aib)
SITE                     16..20
                         note = amino acids at positions 16 and 20 form a ring
source                   1..40
                         mol_type = protein
                         organism = synthetic construct
SEQUENCE: 50
HXQGTFTSDY SKYLDEKRAK EFVQWLLDHH PSSGQPPPSC                                 40

SEQ ID NO: 51            moltype = AA  length = 30
FEATURE                  Location/Qualifiers
REGION                   1..30
                         note = Trigonal agonist
MOD_RES                  2
                         note = Xaa is aminoisobutyric acid (Aib)
SITE                     16..20
                         note = amino acids at positions 16 and 20 form a ring
source                   1..30
                         mol_type = protein
                         organism = synthetic construct
SEQUENCE: 51
HXQGTFTSDY SKYLDEKRQK EFVQWLLNTC                                            30

SEQ ID NO: 52            moltype = AA  length = 30
FEATURE                  Location/Qualifiers
REGION                   1..30
                         note = Trigonal agonist
MOD_RES                  2
                         note = Xaa is aminoisobutyric acid (Aib)
SITE                     16..20
                         note = amino acids at positions 16 and 20 form a ring
source                   1..30
                         mol_type = protein
                         organism = synthetic construct
SEQUENCE: 52
HXQGTFTSDY SKYLDEKRQK EFVQWLLDTC                                            30

SEQ ID NO: 53            moltype = AA  length = 30
FEATURE                  Location/Qualifiers
REGION                   1..30
                         note = Trigonal agonist
MOD_RES                  2
                         note = Xaa is aminoisobutyric acid (Aib)
SITE                     16..20
                         note = amino acids at positions 16 and 20 form a ring
source                   1..30
                         mol_type = protein
                         organism = synthetic construct
SEQUENCE: 53
HXEGTFTSDY SIAMDEIHQK DFVNWLLAQC                                            30

SEQ ID NO: 54            moltype = AA  length = 30
FEATURE                  Location/Qualifiers
REGION                   1..30
                         note = Trigonal agonist
MOD_RES                  2
                         note = Xaa is aminoisobutyric acid (Aib)
SITE                     16..20
                         note = amino acids at positions 16 and 20 form a ring
source                   1..30
                         mol_type = protein
                         organism = synthetic construct
SEQUENCE: 54
HXEGTFTSDY SIAMDEIHQK DFVDWLLAEC                                            30

SEQ ID NO: 55            moltype = AA  length = 30
FEATURE                  Location/Qualifiers
REGION                   1..30
                         note = Trigonal agonist
MOD_RES                  2
                         note = Xaa is aminoisobutyric acid (Aib)
SITE                     16..20
                         note = amino acids at positions 16 and 20 form a ring
```

```
                          -continued source                1..30
                      mol_type = protein
                      organism = synthetic construct
SEQUENCE: 55
HXQGTFTSDY SIAMDEIHQK DFVNWLLAQC                                        30

SEQ ID NO: 56         moltype = AA  length = 30
FEATURE               Location/Qualifiers
REGION                1..30
                      note = Trigonal agonist
MOD_RES               2
                      note = Xaa is aminoisobutyric acid (Aib)
SITE                  16..20
                      note = amino acids at positions 16 and 20 form a ring
source                1..30
                      mol_type = protein
                      organism = synthetic construct
SEQUENCE: 56
HXQGTFTSDY SKYLDEKRQK EFVNWLLAQC                                        30

SEQ ID NO: 57         moltype = AA  length = 30
FEATURE               Location/Qualifiers
REGION                1..30
                      note = Trigonal agonist
MOD_RES               2
                      note = Xaa is aminoisobutyric acid (Aib)
SITE                  16..20
                      note = amino acids at positions 16 and 20 form a ring
source                1..30
                      mol_type = protein
                      organism = synthetic construct
SEQUENCE: 57
HXQGTFTSDY SIAMDEIHQK DFVNWLLNTC                                        30

SEQ ID NO: 58         moltype = AA  length = 31
FEATURE               Location/Qualifiers
REGION                1..31
                      note = Trigonal agonist
MOD_RES               2
                      note = Xaa is aminoisobutyric acid (Aib)
SITE                  16..20
                      note = amino acids at positions 16 and 20 form a ring
source                1..31
                      mol_type = protein
                      organism = synthetic construct
SEQUENCE: 58
HXQGTFTSDY SKYLDEKRQK EFVQWLLNTK C                                      31

SEQ ID NO: 59         moltype = AA  length = 30
FEATURE               Location/Qualifiers
REGION                1..30
                      note = Trigonal agonist
SITE                  1
                      note = Xaa is 4-imidazoacetyl (CA)
MOD_RES               2
                      note = Xaa is aminoisobutyric acid (Aib)
SITE                  16..20
                      note = amino acids at positions 16 and 20 form a ring
source                1..30
                      mol_type = protein
                      organism = synthetic construct
SEQUENCE: 59
XXQGTFTSDY SICMDEKHQK DFVNWLLNTK                                        30

SEQ ID NO: 60         moltype = AA  length = 30
FEATURE               Location/Qualifiers
REGION                1..30
                      note = Trigonal agonist
SITE                  1
                      note = Xaa is 4-imidazoacetyl (CA)
MOD_RES               2
                      note = Xaa is aminoisobutyric acid (Aib)
SITE                  16..20
                      note = amino acids at positions 16 and 20 form a ring
source                1..30
                      mol_type = protein
                      organism = synthetic construct
SEQUENCE: 60
XXQGTFTSDY SIAMDEKHCK DFVNWLLNTK                                        30
```

```
SEQ ID NO: 61            moltype = AA  length = 30
FEATURE                  Location/Qualifiers
REGION                   1..30
                         note = Trigonal agonist
SITE                     1
                         note = Xaa is 4-imidazoacetyl (CA)
MOD_RES                  2
                         note = Xaa is aminoisobutyric acid (Aib)
SITE                     16..20
                         note = amino acids at positions 16 and 20 form a ring
source                   1..30
                         mol_type = protein
                         organism = synthetic construct
SEQUENCE: 61
XXQGTFTSDY SIAMDEIACK DFVNWLLNTK                                          30

SEQ ID NO: 62            moltype = AA  length = 39
FEATURE                  Location/Qualifiers
REGION                   1..39
                         note = Trigonal agonist
SITE                     1
                         note = Xaa is 4-imidazoacetyl (CA)
MOD_RES                  2
                         note = Xaa is aminoisobutyric acid (Aib)
source                   1..39
                         mol_type = protein
                         organism = synthetic construct
SEQUENCE: 62
XXQGTFTSDK SKYLDERAAQ DFVQWLLDGG PSSGAPPPS                                39

SEQ ID NO: 63            moltype = AA  length = 39
FEATURE                  Location/Qualifiers
REGION                   1..39
                         note = Trigonal agonist
SITE                     1
                         note = Xaa is 4-imidazoacetyl (CA)
MOD_RES                  2
                         note = Xaa is aminoisobutyric acid (Aib)
source                   1..39
                         mol_type = protein
                         organism = synthetic construct
SEQUENCE: 63
XXQGTFTSDC SKYLDERAAQ DFVQWLLDGG PSSGAPPPS                                39

SEQ ID NO: 64            moltype = AA  length = 39
FEATURE                  Location/Qualifiers
REGION                   1..39
                         note = Trigonal agonist
MOD_RES                  2
                         note = Xaa is aminoisobutyric acid (Aib)
SITE                     16..20
                         note = amino acids at positions 16 and 20 form a ring
source                   1..39
                         mol_type = protein
                         organism = synthetic construct
SEQUENCE: 64
YXQGTFTSDY SKYLDECAAK EFVQWLLDHH PSSGQPPPS                                39

SEQ ID NO: 65            moltype = AA  length = 39
FEATURE                  Location/Qualifiers
REGION                   1..39
                         note = Trigonal agonist
MOD_RES                  2
                         note = Xaa is aminoisobutyric acid (Aib)
SITE                     16..20
                         note = amino acids at positions 16 and 20 form a ring
source                   1..39
                         mol_type = protein
                         organism = synthetic construct
SEQUENCE: 65
HXQGTFTSDY SKCLDEKRAK EFVQWLLDHH PSSGQPPPS                                39

SEQ ID NO: 66            moltype = AA  length = 39
FEATURE                  Location/Qualifiers
REGION                   1..39
                         note = Trigonal agonist
MOD_RES                  2
                         note = Xaa is aminoisobutyric acid (Aib)
```

```
SITE                    16..20
                        note = amino acids at positions 16 and 20 form a ring
source                  1..39
                        mol_type = protein
                        organism = synthetic construct
SEQUENCE: 66
YXQGTFTSDY SKYLDECRAK DFVQWLLDHH PSSGQPPPS                               39

SEQ ID NO: 67           moltype = AA  length = 39
FEATURE                 Location/Qualifiers
REGION                  1..39
                        note = Trigonal agonist
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 67
YXQGTFTSDY SKYLDECAAK DFVQWLLDHH PSSGQPPPS                               39

SEQ ID NO: 68           moltype = AA  length = 39
FEATURE                 Location/Qualifiers
REGION                  1..39
                        note = Trigonal agonist
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 68
YXQGTFTSDY SKCLDEKAAK EFVQWLLDHH PSSGQPPPS                               39

SEQ ID NO: 69           moltype = AA  length = 39
FEATURE                 Location/Qualifiers
REGION                  1..39
                        note = Trigonal agonist
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 69
YXQGTFTSDY SKCLDERAAK EFVQWLLDHH PSSGQPPPS                               39

SEQ ID NO: 70           moltype = AA  length = 39
FEATURE                 Location/Qualifiers
REGION                  1..39
                        note = Trigonal agonist
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 70
YXQGTFTSDY SKCLDEKRAK DFVQWLLDHH PSSGQPPPS                               39

SEQ ID NO: 71           moltype = AA  length = 39
FEATURE                 Location/Qualifiers
REGION                  1..39
                        note = Trigonal agonist
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 71
YXQGTFTSDY SKYLDERACK DFVQWLLDHH PSSGQPPPS                               39

SEQ ID NO: 72           moltype = AA  length = 39
```

```
FEATURE                 Location/Qualifiers
REGION                  1..39
                        note = Trigonal agonist
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 72
YXQGTFTSDC SKYLDERAAK DFVQWLLDHH PSSGQPPPS                              39

SEQ ID NO: 73           moltype = AA  length = 39
FEATURE                 Location/Qualifiers
REGION                  1..39
                        note = Trigonal agonist
SITE                    1
                        note = Xaa is 4-imidazoacetyl (CA)
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 73
XXQGTFTSDY SKYLDECRAK EFVQWLLDHH PSSGQPPPS                              39

SEQ ID NO: 74           moltype = AA  length = 39
FEATURE                 Location/Qualifiers
REGION                  1..39
                        note = Trigonal agonist
SITE                    1
                        note = Xaa is 4-imidazoacetyl (CA)
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 74
XXQGTFTSDY SKCLDEKRAK EFVQWLLDHH PSSGQPPPS                              39

SEQ ID NO: 75           moltype = AA  length = 40
FEATURE                 Location/Qualifiers
REGION                  1..40
                        note = Trigonal agonist
MOD_RES                 2
                        note = Xaa is aminoisobutyric acid (Aib)
SITE                    16..20
                        note = amino acids at positions 16 and 20 form a ring
source                  1..40
                        mol_type = protein
                        organism = synthetic construct
SEQUENCE: 75
YXQGTFTSDY SKYLDEKAAK EFVQWLLDHH PSSGQPPPSC                             40

SEQ ID NO: 76           moltype = AA  length = 40
FEATURE                 Location/Qualifiers
REGION                  1..40
                        note = Trigonal agonist
MOD_RES                 2
                        note = Xaa is aminoisobutyric acid (Aib)
SITE                    16..20
                        note = amino acids at positions 16 and 20 form a ring
source                  1..40
                        mol_type = protein
                        organism = synthetic construct
SEQUENCE: 76
YXQGTFTSDY SKYLDEKRAK DFVQWLLDHH PSSGQPPPSC                             40

SEQ ID NO: 77           moltype = AA  length = 40
FEATURE                 Location/Qualifiers
REGION                  1..40
                        note = Trigonal agonist
MOD_RES                 2
                        note = Xaa is aminoisobutyric acid (Aib)
```

```
SITE                    16..20
                        note = amino acids at positions 16 and 20 form a ring
source                  1..40
                        mol_type = protein
                        organism = synthetic construct
SEQUENCE: 77
YXQGTFTSDY SKYLDEKAAK DFVQWLLDHH PSSGQPPPSC                              40

SEQ ID NO: 78           moltype = AA  length = 31
FEATURE                 Location/Qualifiers
REGION                  1..31
                        note = Trigonal agonist
MOD_RES                 2
                        note = Xaa is aminoisobutyric acid (Aib)
SITE                    16..20
                        note = amino acids at positions 16 and 20 form a ring
source                  1..31
                        mol_type = protein
                        organism = synthetic construct
SEQUENCE: 78
HXQGTFTSDY SKYLDEKRQK EFVQWLLDTK C                                       31

SEQ ID NO: 79           moltype = AA  length = 31
FEATURE                 Location/Qualifiers
REGION                  1..31
                        note = Trigonal agonist
MOD_RES                 2
                        note = Xaa is aminoisobutyric acid (Aib)
SITE                    16..20
                        note = amino acids at positions 16 and 20 form a ring
source                  1..31
                        mol_type = protein
                        organism = synthetic construct
SEQUENCE: 79
HXEGTFTSDY SIAMDEIHQK DFVNWLLAQK C                                       31

SEQ ID NO: 80           moltype = AA  length = 31
FEATURE                 Location/Qualifiers
REGION                  1..31
                        note = Trigonal agonist
MOD_RES                 2
                        note = Xaa is aminoisobutyric acid (Aib)
SITE                    16..20
                        note = amino acids at positions 16 and 20 form a ring
source                  1..31
                        mol_type = protein
                        organism = synthetic construct
SEQUENCE: 80
HXEGTFTSDY SIAMDEIHQK DFVDWLLAEK C                                       31

SEQ ID NO: 81           moltype = AA  length = 30
FEATURE                 Location/Qualifiers
REGION                  1..30
                        note = Trigonal agonist
SITE                    1
                        note = Xaa is 4-imidazoacetyl (CA)
MOD_RES                 2
                        note = Xaa is aminoisobutyric acid (Aib)
SITE                    16..20
                        note = amino acids at positions 16 and 20 form a ring
source                  1..30
                        mol_type = protein
                        organism = synthetic construct
SEQUENCE: 81
XXQGTFTSDY SKYLDEKRQK EFVQWLLNTC                                         30

SEQ ID NO: 82           moltype = AA  length = 30
FEATURE                 Location/Qualifiers
REGION                  1..30
                        note = Trigonal agonist
SITE                    1
                        note = Xaa is 4-imidazoacetyl (CA)
MOD_RES                 2
                        note = Xaa is aminoisobutyric acid (Aib)
SITE                    16..20
                        note = amino acids at positions 16 and 20 form a ring
source                  1..30
                        mol_type = protein
                        organism = synthetic construct
```

```
SEQUENCE: 82
XXQGTFTSDY SKYLDEKRQK EFVQWLLDTC                                           30

SEQ ID NO: 83              moltype = AA  length = 30
FEATURE                    Location/Qualifiers
REGION                     1..30
                           note = Trigonal agonist
SITE                       1
                           note = Xaa is 4-imidazoacetyl (CA)
MOD_RES                    2
                           note = Xaa is aminoisobutyric acid (Aib)
SITE                       16..20
                           note = amino acids at positions 16 and 20 form a ring
source                     1..30
                           mol_type = protein
                           organism = synthetic construct
SEQUENCE: 83
XXEGTFTSDY SIAMDEIHQK DFVNWLLAQC                                           30

SEQ ID NO: 84              moltype = AA  length = 30
FEATURE                    Location/Qualifiers
REGION                     1..30
                           note = Trigonal agonist
SITE                       1
                           note = Xaa is 4-imidazoacetyl (CA)
MOD_RES                    2
                           note = Xaa is aminoisobutyric acid (Aib)
SITE                       16..20
                           note = amino acids at positions 16 and 20 form a ring
source                     1..30
                           mol_type = protein
                           organism = synthetic construct
SEQUENCE: 84
XXEGTFTSDY SIAMDEIHQK DFVDWLLAEC                                           30

SEQ ID NO: 85              moltype = AA  length = 30
FEATURE                    Location/Qualifiers
REGION                     1..30
                           note = Trigonal agonist
SITE                       1
                           note = Xaa is 4-imidazoacetyl (CA)
MOD_RES                    2
                           note = Xaa is aminoisobutyric acid (Aib)
SITE                       16..20
                           note = amino acids at positions 16 and 20 form a ring
source                     1..30
                           mol_type = protein
                           organism = synthetic construct
SEQUENCE: 85
XXQGTFTSDY SIAMDEIHQK DFVNWLLAQC                                           30

SEQ ID NO: 86              moltype = AA  length = 30
FEATURE                    Location/Qualifiers
REGION                     1..30
                           note = Trigonal agonist
SITE                       1
                           note = Xaa is 4-imidazoacetyl (CA)
MOD_RES                    2
                           note = Xaa is aminoisobutyric acid (Aib)
SITE                       16..20
                           note = amino acids at positions 16 and 20 form a ring
source                     1..30
                           mol_type = protein
                           organism = synthetic construct
SEQUENCE: 86
XXQGTFTSDY SKYLDEKRQK EFVNWLLAQC                                           30

SEQ ID NO: 87              moltype = AA  length = 30
FEATURE                    Location/Qualifiers
REGION                     1..30
                           note = Trigonal agonist
SITE                       1
                           note = Xaa is 4-imidazoacetyl (CA)
MOD_RES                    2
                           note = Xaa is aminoisobutyric acid (Aib)
SITE                       16..20
                           note = amino acids at positions 16 and 20 form a ring
```

```
                        -continued source                  1..30
                        mol_type = protein
                        organism = synthetic construct
SEQUENCE: 87
XXQGTFTSDY SIAMDEIHQK DFVNWLLNTC                                         30

SEQ ID NO: 88           moltype = AA  length = 31
FEATURE                 Location/Qualifiers
REGION                  1..31
                        note = Trigonal agonist
SITE                    1
                        note = Xaa is 4-imidazoacetyl (CA)
MOD_RES                 2
                        note = Xaa is aminoisobutyric acid (Aib)
SITE                    16..20
                        note = amino acids at positions 16 and 20 form a ring
source                  1..31
                        mol_type = protein
                        organism = synthetic construct
SEQUENCE: 88
XXQGTFTSDY SKYLDEKRQK EFVQWLLNTK C                                       31

SEQ ID NO: 89           moltype = AA  length = 31
FEATURE                 Location/Qualifiers
REGION                  1..31
                        note = Trigonal agonist
SITE                    1
                        note = Xaa is 4-imidazoacetyl (CA)
MOD_RES                 2
                        note = Xaa is aminoisobutyric acid (Aib)
SITE                    16..20
                        note = amino acids at positions 16 and 20 form a ring
source                  1..31
                        mol_type = protein
                        organism = synthetic construct
SEQUENCE: 89
XXQGTFTSDY SKYLDEKRQK EFVQWLLDTK C                                       31

SEQ ID NO: 90           moltype = AA  length = 31
FEATURE                 Location/Qualifiers
REGION                  1..31
                        note = Trigonal agonist
SITE                    1
                        note = Xaa is 4-imidazoacetyl (CA)
MOD_RES                 2
                        note = Xaa is aminoisobutyric acid (Aib)
SITE                    16..20
                        note = amino acids at positions 16 and 20 form a ring
source                  1..31
                        mol_type = protein
                        organism = synthetic construct
SEQUENCE: 90
XXEGTFTSDY SIAMDEIHQK DFVNWLLAQK C                                       31

SEQ ID NO: 91           moltype = AA  length = 31
FEATURE                 Location/Qualifiers
REGION                  1..31
                        note = Trigonal agonist
SITE                    1
                        note = Xaa is 4-imidazoacetyl (CA)
MOD_RES                 2
                        note = Xaa is aminoisobutyric acid (Aib)
SITE                    16..20
                        note = amino acids at positions 16 and 20 form a ring
source                  1..31
                        mol_type = protein
                        organism = synthetic construct
SEQUENCE: 91
XXEGTFTSDY SIAMDEIHQK DFVDWLLAEK C                                       31

SEQ ID NO: 92           moltype = AA  length = 31
FEATURE                 Location/Qualifiers
REGION                  1..31
                        note = Trigonal agonist
SITE                    1
                        note = Xaa is 4-imidazoacetyl (CA)
MOD_RES                 2
                        note = Xaa is aminoisobutyric acid (Aib)
```

```
                        -continued

SITE                    16..20
                        note = amino acids at positions 16 and 20 form a ring
source                  1..31
                        mol_type = protein
                        organism = synthetic construct
SEQUENCE: 92
XXQGTFTSDY SIAMDEIHQK DFVNWLLAQK C                                              31

SEQ ID NO: 93           moltype = AA  length = 31
FEATURE                 Location/Qualifiers
REGION                  1..31
                        note = Trigonal agonist
SITE                    1
                        note = Xaa is 4-imidazoacetyl (CA)
MOD_RES                 2
                        note = Xaa is aminoisobutyric acid (Aib)
SITE                    16..20
                        note = amino acids at positions 16 and 20 form a ring
source                  1..31
                        mol_type = protein
                        organism = synthetic construct
SEQUENCE: 93
XXQGTFTSDY SKYLDEKRQK EFVNWLLAQK C                                              31

SEQ ID NO: 94           moltype = AA  length = 31
FEATURE                 Location/Qualifiers
REGION                  1..31
                        note = Trigonal agonist
SITE                    1
                        note = Xaa is 4-imidazoacetyl (CA)
MOD_RES                 2
                        note = Xaa is aminoisobutyric acid (Aib)
SITE                    16..20
                        note = amino acids at positions 16 and 20 form a ring
source                  1..31
                        mol_type = protein
                        organism = synthetic construct
SEQUENCE: 94
XXQGTFTSDY SIAMDEIHQK DFVNWLLNTK C                                              31

SEQ ID NO: 95           moltype = AA  length = 39
FEATURE                 Location/Qualifiers
REGION                  1..39
                        note = Trigonal agonist
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 95
YXQGTFTSDY SKYLDEKRAK EFVQWLLCHH PSSGQPPPS                                      39

SEQ ID NO: 96           moltype = AA  length = 39
FEATURE                 Location/Qualifiers
REGION                  1..39
                        note = Trigonal agonist
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
SEQUENCE: 96
YXQGTFTSDY SKYLDEKRAK EFVQWLLDHC PSSGQPPPS                                      39

SEQ ID NO: 97           moltype = AA  length = 39
FEATURE                 Location/Qualifiers
REGION                  1..39
                        note = Trigonal agonist
MOD_RES                 2
                        note = Xaa is aminoisobutyric acid (Aib)
SITE                    16..20
                        note = amino acids at positions 16 and 20 form a ring
source                  1..39
                        mol_type = protein
                        organism = synthetic construct
```

```
SEQUENCE: 97
YXQGTFTSDY SKYLDEKRAK EFVQWLLDCH PSSGQPPPS                              39

SEQ ID NO: 98              moltype = AA  length = 40
FEATURE                    Location/Qualifiers
REGION                     1..40
                           note = Trigonal agonist
MOD_RES                    2
                           note = Xaa is aminoisobutyric acid (Aib)
SITE                       16..20
                           note = amino acids at positions 16 and 20 form a ring
source                     1..40
                           mol_type = protein
                           organism = synthetic construct
SEQUENCE: 98
YXQGTFTSDY SKALDEKAAK EFVNWLLDHH PSSGQPPPSC                             40

SEQ ID NO: 99              moltype = AA  length = 40
FEATURE                    Location/Qualifiers
REGION                     1..40
                           note = Trigonal agonist
MOD_RES                    2
                           note = Xaa is aminoisobutyric acid (Aib)
SITE                       16..20
                           note = amino acids at positions 16 and 20 form a ring
source                     1..40
                           mol_type = protein
                           organism = synthetic construct
SEQUENCE: 99
YXQGTFTSDY SKALDEKAAK DFVNWLLDHH PSSGQPPPSC                             40

SEQ ID NO: 100             moltype = AA  length = 40
FEATURE                    Location/Qualifiers
REGION                     1..40
                           note = Trigonal agonist
MOD_RES                    2
                           note = Xaa is aminoisobutyric acid (Aib)
SITE                       16..20
                           note = amino acids at positions 16 and 20 form a ring
source                     1..40
                           mol_type = protein
                           organism = synthetic construct
SEQUENCE: 100
YXQGTFTSDY SKALDEKAAK EFVQWLLDQH PSSGQPPPSC                             40

SEQ ID NO: 101             moltype = AA  length = 40
FEATURE                    Location/Qualifiers
REGION                     1..40
                           note = Trigonal agonist
MOD_RES                    2
                           note = Xaa is aminoisobutyric acid (Aib)
SITE                       16..20
                           note = amino acids at positions 16 and 20 form a ring
source                     1..40
                           mol_type = protein
                           organism = synthetic construct
SEQUENCE: 101
YXQGTFTSDY SKALDEKAAK EFVNWLLDQH PSSGQPPPSC                             40

SEQ ID NO: 102             moltype = AA  length = 40
FEATURE                    Location/Qualifiers
REGION                     1..40
                           note = Trigonal agonist
MOD_RES                    2
                           note = Xaa is aminoisobutyric acid (Aib)
SITE                       16..20
                           note = amino acids at positions 16 and 20 form a ring
source                     1..40
                           mol_type = protein
                           organism = synthetic construct
SEQUENCE: 102
YXQGTFTSDY SKALDEKAAK DFVNWLLDQH PSSGQPPPSC                             40

SEQ ID NO: 103             moltype = AA  length = 30
FEATURE                    Location/Qualifiers
REGION                     1..30
                           note = General Formula 1
SITE                       1
                           note = Xaa is His (H), 4-imidazoacetyl (CA), or Tyr (Y)
```

```
VARIANT            2
                   note = Xaa is Gly (G), alpha-methyl-glutamic acid, or Aib
                    (aminoisobutyric acid)
VARIANT            3
                   note = Xaa is Glu (E) or Gln (Q)
VARIANT            7
                   note = Xaa is Thr (T) or Ile (I)
VARIANT            10
                   note = Xaa is Leu (L), Tyr (Y), Lys (K), Cys (C), or Val (V)
VARIANT            12
                   note = Xaa is Lys (K), Ser (S), or Ile (I)
VARIANT            13
                   note = Xaa is Gln (Q), Tyr (Y), Ala (A), or Cys (C)
VARIANT            14
                   note = Xaa is Leu (L), Met (M), or Tyr (Y)
VARIANT            15
                   note = Xaa is Cys (C), Asp (D), Glu (E), or Leu (L)
VARIANT            16
                   note = Xaa is Gly (G), Glu (E), or Ser (S)
VARIANT            17
                   note = Xaa is Gln (Q), Arg (R), Ile (I), Glu (E), Cys (C),
                    or Lys (K)
VARIANT            18
                   note = Xaa is Ala (A), Gln (Q), Arg (R), or His (H)
VARIANT            19
                   note = Xaa is Ala (A), Gln (Q), Cys (C), or Val (V)
VARIANT            20
                   note = Xaa is Lys (K), Gln (Q), or Arg (R)
VARIANT            21
                   note = Xaa is Glu (E), Gln (Q), Leu (L), Cys (C), or Asp (D)
VARIANT            23
                   note = Xaa is Ile (I) or Val (V)
VARIANT            24
                   note = Xaa is Ala (A), Gln (Q), Cys (C), Asn (N), Asp (D),
                    or Glu (E)
VARIANT            27
                   note = Xaa is Val (V), Leu (L), Lys (K), or Met (M)
VARIANT            28
                   note = Xaa is Cys (C), Lys (K), Ala (A), Asn (N), or Asp (D)
VARIANT            29
                   note = Xaa is Cys (C), Gly (G), Gln (Q), Thr (T), Glu (E),
                    or His (H)
VARIANT            30
                   note = Xaa is Cys, Gly, Lys or His, or absent; and Xaa can
                    be further linked to R1, wherein R1 is Cys, GKKNDWKHNIT,
                    m-SSGAPPPS-n, or m-SSGQPPPS-n, or absent; m is -Cys-,
                    -Pro-, or -Gly-Pro-; n is -Cys-, -Gly-, -Ser-, or
                    -His-Gly, or absent
source             1..30
                   mol_type = protein
                   organism = synthetic construct
SEQUENCE: 103
XXXGTFXSDX SXXXXXXXXX XFXXWLXXXX                                          30

SEQ ID NO: 104     moltype = AA  length = 11
FEATURE            Location/Qualifiers
REGION             1..11
                   note = R1
source             1..11
                   mol_type = protein
                   organism = synthetic construct
SEQUENCE: 104
GKKNDWKHNI T                                                              11

SEQ ID NO: 105     moltype = AA  length = 8
FEATURE            Location/Qualifiers
REGION             1..8
                   note = R1
source             1..8
                   mol_type = protein
                   organism = synthetic construct
SEQUENCE: 105
SSGAPPPS                                                                   8

SEQ ID NO: 106     moltype = AA  length = 8
FEATURE            Location/Qualifiers
REGION             1..8
                   note = R1
```

```
source              1..8
                    mol_type = protein
                    organism = synthetic construct
SEQUENCE: 106
SSGQPPPS                                                              8
```

The invention claimed is:

1. A polyethylene glycol compound represented by Formula 1 below, a stereoisomer thereof, or a pharmaceutically acceptable salt thereof:

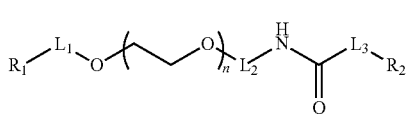

[Formula 1]

wherein, in Formula 1 above,
$R_1$ is aldehyde;
each of $L_1$ and $L_3$ is independently a linear or branched $C_{1-6}$ alkylene;
$L_2$ is a linear or branched $C_{3-6}$ alkylene;
$R_2$ is ortho-pyridyl disulfide (OPSS); and
n is an integer of 10 to 2400.

2. The polyethylene glycol compound, stereoisomer thereof, or pharmaceutically acceptable salt of claim 1, wherein the polyethylene glycol compound is represented by Formula 2 below:

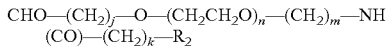

[Formula 2]

CHO—(CH$_2$)$_j$—O—(CH$_2$CH$_2$O)$_n$—(CH$_2$)$_m$—NH(CO)—(CH$_2$)$_k$—R$_2$ wherein, in Formula 2 above;
n is an integer of 10 to 2400;
each of j and k is independently an integer of 1 to 6;
m is an integer of 3 to 6; and
$R_2$ is OPSS.

3. The polyethylene glycol compound, stereoisomer thereof, or pharmaceutically acceptable salt of claim 1, wherein the polyethylene glycol compound is represented by Formula 9 below:

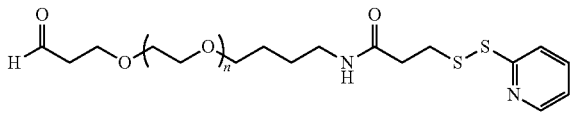

[Formula 9]

wherein, in Formula 9, n is an integer of 10 to 2400.

4. A method for preparing a physiologically active polypeptide to which a polyethylene glycol compound is attached, comprising reacting the polyethylene glycol compound according to claim 1 with a physiologically active polypeptide.

5. The method of claim 4, wherein OPSS as $R_2$ reacts with a thiol group of a cysteine residue of the physiologically active polypeptide.

6. The method of claim 4, further comprising purifying the physiologically active polypeptide to which a polyethylene glycol compound is attached.

7. The method of claim 4, wherein the physiologically active polypeptide is selected from the group consisting of hormones, cytokines, enzymes, antibodies, growth factors, transcription factors, blood factors, vaccines, insulinotropic peptides, neuropeptides, pituitary hormones, anti-obesity peptides, antiviral peptides, non-native peptide derivatives having a physiological activity, structural proteins, ligand proteins, and receptors.

8. The method of claim 4, wherein the physiologically active polypeptide is selected from the group consisting of glucagon; insulin; somatostatin; peptide YY (PYY); neuropeptide Y (NPY); glucagon-like peptides including glucagon-like peptide-1 (GLP-1) and glucagon-like peptide-2 (GLP-2); exendin-3; exendin-4; oxyntomodulin; peptides having an activity on glucagon receptors, GLP-1 receptors, and GIP receptors; fibroblast growth factor; ghrelin; angiotensin; bradykinin; calcitonin; corticotropin; eledoisin; gastrin; leptin; oxytocin; vasopressin; luteinizing hormone; luteotropin; follicle-stimulating hormone; parathyroid hormone; secretin; sermorelin; human growth hormone (hGH); growth hormone-releasing peptides; granulocyte-colony-stimulating factors (GCSF); interferons (IFNs); interleukins; prolactin-releasing peptides; orexin; thyroid-releasing peptides; cholecystokinin; gastrin inhibitory peptides; calmodulin; gastric-releasing peptides; motilin; vasoactive intestinal peptides; atrial natriuretic peptides (ANPs); B-type natriuretic peptides (BNPs); C-type natriuretic peptides (CNPs); neurokinin A; neuromedin; renin; endothelin; sarafotoxin peptide; carsomorphin peptide; dermorphin; dynorphin; endorphin; enkepalin; T cell factors; tumor necrosis factor; tumor necrosis factor receptors; urokinase receptors; tumor inhibitory factors; collagenase inhibitors; thymopoietin; thymulin; thymopentin; thymosin; thymic humoral factor; adrenomedullin; allatostatin; amyloid β-protein fragments; antibacterial peptides; antioxidant peptides; bombesin; osteocalcin; CART peptides; E-selectin; ICAM-1; VCAM-1; leucokine; kringle-5; laminin; inhibin; galanin; fibronectin; pancreastatin; fuzeon; interferon receptors; G protein-coupled receptors; interleukin receptors; enzymes; interleukin-binding proteins; cytokine-binding proteins; macrophage-activating factors; macrophage peptides; B cell factor; protein A; allergy inhibitors; cell necrosis glycoprotein; immunotoxin; lymphotoxin; tumor inhibitory factors; metastasis growth factors; α-1-antitrypsin; albumin; α-lactalbumin; apolipoprotein-E; erythropoietin; highly glycosylated erythropoietin; angiopoietins; hemoglobin; thrombin; thrombin receptor-activating peptides; thrombomodulin; blood factors VII, VIIa, VIII, IX, and XIII; plasminogen-activating factors; fibrin-binding peptides; urokinase; streptokinase; hirudin; protein C; C-reactive protein; renin inhibitors; superoxide dismutase; platelet-derived growth factors; epidermal growth factors; epithelial cell growth factors; angiostatin; angiotensin; osteogenic growth factors; osteogenesis-promoting proteins; atriopeptin; cartilage-inducing factors; elcatonin; connective tissue-activating factors; tissue factor pathway inhibitors; luteinizing hormone-releasing hormone; nerve growth factors; relaxin; somatomedin; insulin-like growth factor; adrenocortical hormone; pancreatic polypeptides; gastrin-releasing peptides; corticotropin-releasing factor; thyroid-stimulating hormone; autotoxin; lactoferrin; myostatin; cell surface antigens; virus-derived vaccine antigens; monoclonal antibody; polyclonal antibody; antibody fragments; erythropoietic growth factors; leukopoietin; amylin; and analogs thereof.

9. A method for preparing a conjugate in which a physiologically active polypeptide and a carrier protein are linked by a polyethylene glycol compound, comprising:
   (a) reacting the polyethylene glycol compound according to claim 1 with any one of a physiologically active polypeptide or carrier protein, thereby preparing a polyethylene glycol compound, wherein the physiologically active polypeptide or carrier protein is attached to one end of the polyethylene glycol compound and the other end of the polyethylene glycol compound has a reactive end group; and
   (b) reacting the polyethylene glycol compound prepared in step (a) above, wherein the physiologically active polypeptide or carrier protein is attached to one end of the polyethylene glycol compound and the other end of the polyethylene glycol compound has a reactive end group, with the other one between the physiologically active polypeptide or carrier protein, so as to link the carrier protein or physiologically active polypeptide to the reactive end group of the polyethylene glycol compound, thereby preparing a conjugate in which the physiologically active polypeptide and the carrier protein are linked by a polyethylene glycol compound.

10. The method of claim 9, wherein the physiologically active polypeptide is selected from the group consisting of hormones, cytokines, enzymes, antibodies, growth factors, transcription factors, blood factors, vaccines, insulinotropic peptides, neuropeptides, pituitary hormones, anti-obesity peptides, antiviral peptides, non-native peptide derivatives having a physiological activity, structural proteins, ligand proteins, and receptors.

11. The method of claim 9, wherein wherein step (a) is to react $R_2$ of the polyethylene glycol compound having the structure of Formula 1 below with a thiol group located at the cysteine residue of the physiologically active polypeptide;

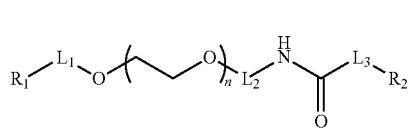

[Formula 1]

wherein, in Formula 1 above,
$R_1$ is an aldehyde group;
each of $L_1$ to $L_3$ is independently a linear or branched $C_{1-6}$ alkylene;
$L_2$ is a linear or branched $C_{3-6}$ alkylene;
$R_2$ is ortho-pyridyl disulfide (OPSS); and
n is an integer of 10 to 2400.

12. The method of claim 11, wherein step (b) is to react an aldehyde end group of the polyethylene glycol compound with an amine group of the carrier protein.

13. The method of claim 9, further comprising purifying the conjugate, wherein the physiologically active polypeptide and the carrier protein are linked by a polyethylene glycol compound.

14. The method of claim 9, wherein the carrier protein is albumin and a fragment thereof, a polymer of a repeating unit of a particular amino acid sequence, antibody, an antibody fragment, an FcRn-binding material, fibronectin, transferrin, saccharide, or elastin.

15. The method of claim 14, wherein the FcRn-binding material is an immunoglobulin Fc fragment.

16. A method for preparing the polyethylene glycol compound of claim 1, comprising:
   (a) reacting a compound of Formula 21 below with a compound of Formula 25 below to introduce the structure of —NH(CO)$L_3$-$R_2$ to one end of a polyethylene glycol:

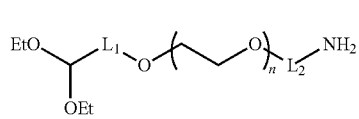

[Formula 21]

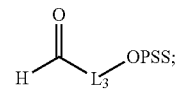

[Formula 25]

and
   (b) introducing $R_1$ to the other end of the polyethylene glycol by replacing the —C(OEt)$_2$ with $R_1$,
wherein $R_1$, $R_2$, $L_1$, $L_2$, $L_3$, and n have the same meanings as defined in claim 1.

* * * * *